United States Patent [19]

Kawai et al.

[11] Patent Number: 5,858,995

[45] Date of Patent: Jan. 12, 1999

[54] BENZOFURAN DERIVATIVES USEFUL AS INHIBITORS OF BONE RESORPTION

[75] Inventors: Yoshio Kawai, Kanagawa; Hitoshi Yamazaki, Ibaraki; Natsuko Kayakiri, Ibaraki; Kousei Yoshihara, Ibaraki; Takumi Yatabe, Ibaraki; Teruo Oku, Ibaraki, all of Japan

[73] Assignee: Fujisawa Pharmaceutical Co., Ltd., Osaka, Japan

[21] Appl. No.: 727,627

[22] PCT Filed: Apr. 21, 1995

[86] PCT No.: PCT/JP95/00787

§ 371 Date: Oct. 25, 1996

§ 102(e) Date: Oct. 25, 1996

[87] PCT Pub. No.: WO95/29907

PCT Pub. Date: Nov. 9, 1995

[30]       Foreign Application Priority Data

Apr. 29, 1994 [GB] United Kingdom .................... 9408577

[51] Int. Cl.$^6$ ......................... A61K 31/34; C07D 307/81; C07D 307/80; C07D 307/79
[52] U.S. Cl. ........................... 514/100; 514/468; 514/469; 549/220; 549/460; 549/467; 549/468
[58] Field of Search ..................................... 549/471, 460, 549/220, 467, 468; 514/100, 468, 469

[56]       References Cited

PUBLICATIONS

Erlenmeyer et al., Helv. Chim. Acta vol. 31, pp. 75–77, 1948.
Chemical Abstracts, vol. 112: 50495, 1990.
Palidowicz et al., J. Org. Chem., vol. 58, pp. 4802–4804, 1993.

*Primary Examiner*—Bernard Dentz
*Attorney, Agent, or Firm*—Oblon, Spivak, McClelland, Maier & Neustadt, P.C.

[57]       ABSTRACT

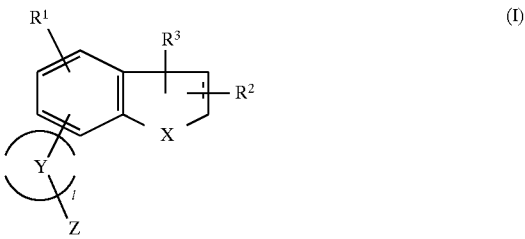

This invention relates to a novel heterocyclic compound represented by formula (I), wherein each symbol is as defined in the specification and a pharmaceutically acceptable salt thereof which are the inhibitors of bone resorption and bone metabolism, to processes for preparation thereof, to a pharmaceutical composition comprising the same and to a method for the treatment of diseases caused by abnormal bone metabolism in human being or an animal.

11 Claims, No Drawings

BENZOFURAN DERIVATIVES USEFUL AS INHIBITORS OF BONE RESORPTION

This application is a 371 of PCT/JP95/00787 filed Apr. 21, 1995.

TECHNICAL FIELD

The present invention relates to a novel heterocyclic compound and a pharmaceutically acceptable salt thereof which are useful as a medicament.

BACKGROUND ART

In Japanese Patent Application Laid-open No.60-48924, No. 60-54379, etc., there are disclosed thionaphten-2-carboxylic acid derivatives and 3-phenyl-4H-1-benzopyran-4-one derivatives inhibiting bone resorption.

DISCLOSURE OF INVENTION

The present invention relates to a novel heterocyclic compound and a pharmaceutically acceptable salt thereof which are the inhibitors of bone resorption, the inhibitors of bone metastases and useful for the prophylactic and/or therapeutic treatment of bone disease characterized by abnormal bone metabolism such as osteoporosis (especially, postmenopausal osteoporosis); hyper-calcemia; hyperparathyroidism; Paget's bone diseases; osteolysis; hypercalcemia of malignancy with or without bone metastases; rheumatoid arthritis; periodontitis; osteoarthritis; ostealgia; osteopenia; cancer cachexia; or the like in a human being or an animal.

And further, the present invention relates to processes for the preparation of the heterocyclic derivatives, to a pharmaceutical composition comprising the same and to a method for the prophylactic and/or therapeutic treatment of above-mentioned diseases in a human being or an animal, and to a use of the heterocyclic derivatives and pharmaceutically acceptable salts thereof for the prophylactic and/or therapeutic treatment of above-mentioned diseases in human therapeutic treatment of above-mentioned diseases in human being or an animal.

The heterocyclic derivatives of this invention are new and can be represented by the following general formula (I):

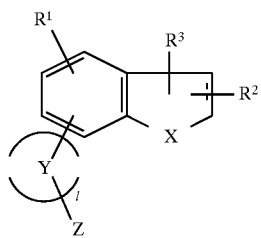

wherein
- $R^1$ is hydrogen, lower alkyl, an acyl group, amino, acylamino, nitro, halogen or hydroxy(lower)alkyl which may have one or more suitable substituent(s),
- $R^2$ is hydrogen, lower alkyl, an acyl group, lower alkoxy, acyl(lower)alkyl, aryl, cyano, mono-(or di- or tri-)-halo (lower)alkyl, lower alkylthio or hydroxy(lower)alkyl which may have one or more suitable substituent(s),
- $R^3$ is hydrogen, lower alkyl, lower alkenyl, cyclo(lower) alkyl(lower)alkyl, halogen, an acyl group, acyl(lower) alkyl, acylamino, acylamino(lower)alkyl, acyl(lower) alkenyl, acyloxy(lower)alkyl, acyl(lower)alkylthio (lower)alkyl, amino(lower)alkyl, mono-(or di-)lower alkylamino, lower alkylthio(lower)alkyl, hydroxyimino(lower)alkyl which may have one or more suitable substituent(s), hydroxy(lower)alkyl which may have one or more suitable substituent(s), hydroxy(lower)alkylthio(lower)alkyl, cyano(lower) alkyl, mono-(or di-)lower alkoxy(lower)alkyl which may have one or more suitable substituent(s), lower alkyl substituted with aryl which may have one or more suitable substituent(s), mono-(or di-)lower alkylamino (lower)alkyl, lower alkyl substituted with heterocyclic group which may have one or more suitable substituent (s), heterocyclic group which may have one or more suitable substituent(s), heterocyclicthio, heterocyclicthio(lower),alkyl, heterocyclicoxy, heterocyclicoxy(lower)alkyl, heterocyclicaminoimino-(lower)alkyl, aryl, amino or nitro, in which $R^2$ and R3 may be linked together to form
  (1) lower alkylene which may have one or more suitable substituent(s),
  (2) lower alkenylene which may have one or more suitable substituent(s), or
  (3) a group of the formula

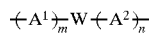

[wherein $A^1$ and $A^2$ are each lower alkylene which may have one or more suitable substituent(s) or lower alkenylene which may have one or more suitable substituent(s),
  W is

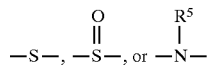

(wherein $R^5$ is hydrogen, lower alkyl or an acyl group) and
  m and n are each integer of 0 or 1.], X is O or S, Y is vinylene, or a group of the formula:

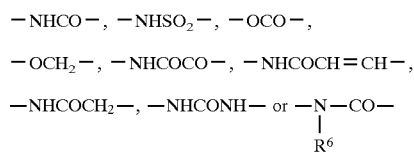

(wherein $R^6$ is lower alkyl),

Z is heterocyclic group which may have one or more suitable substituent(s), or aryl which may have one or more suitable substituent(s), l is an integer of 0 or 1, and --- is a single bond or a double bond, and a pharmaceutically acceptable salt thereof.

The object compound (I) or a salt thereof can be prepared by the processes as illustrated in the following reaction schemes.

Process 1

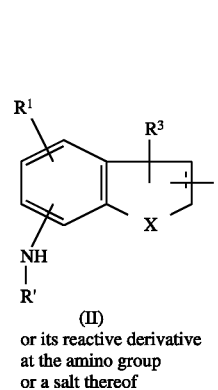
(II)
or its reactive derivative
at the amino group
or a salt thereof

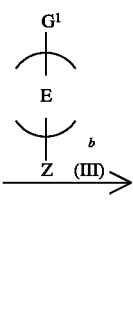
(III)

or its reactive
derivative at
the carboxy group or
sulfo group or a
salt thereof

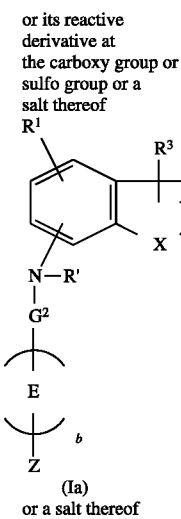
(Ia)
or a salt thereof

Process 2

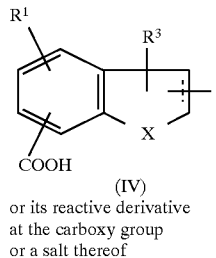
(IV)
or its reactive derivative
at the carboxy group
or a salt thereof $H_2N-Z$ (V)

or its reactive
derivative at
the amino group
or a salt thereof

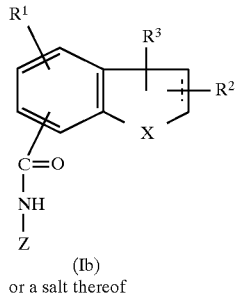
(Ib)
or a salt thereof

Process 3

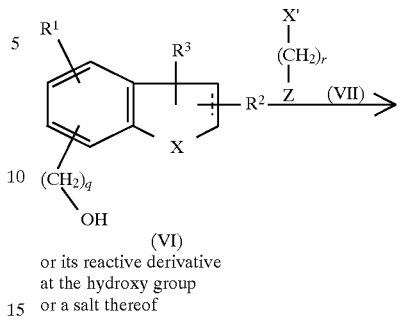
(VI)
or its reactive derivative
at the hydroxy group
or a salt thereof

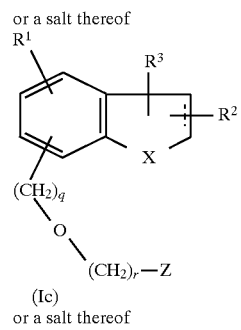
(Ic)
or a salt thereof

Process 4

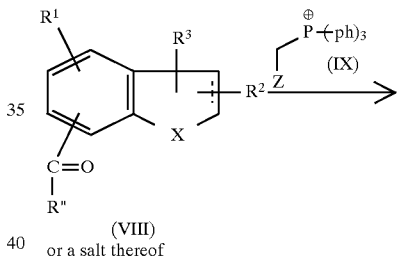
(VIII)
or a salt thereof

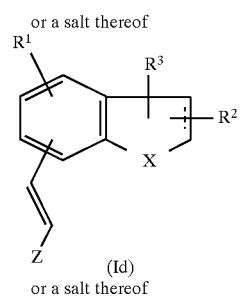
(Id)
or a salt thereof

Process 5

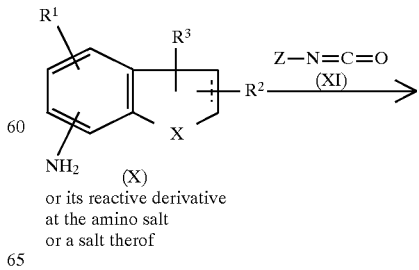
(X)
or its reactive derivative
at the amino salt
or a salt therof $Z-N=C=O$ (XI)

-continued

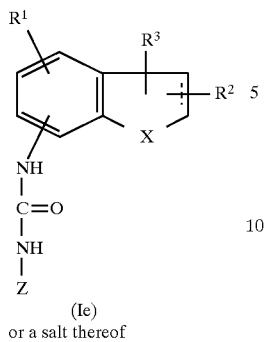

(Ie)
or a salt thereof

Process 6

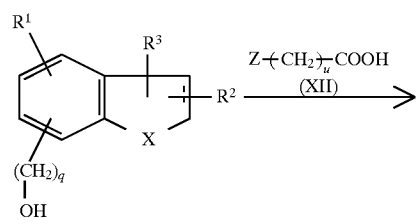 $\xrightarrow{Z\text{-}(CH_2)_u\text{-}COOH \quad (XII)}$ (VI)
or its reactive derivative
at the hydroxy group
or a salt thereof or its reactive
derivative at
the carboxy group
or a salt thereof

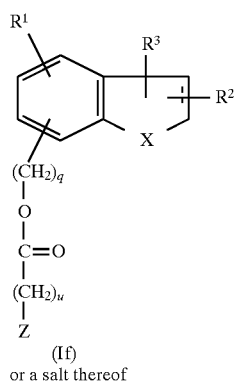

(If)
or a salt thereof

Process 7

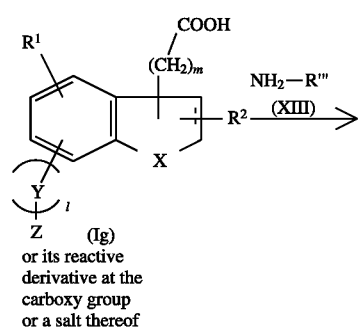 $\xrightarrow{NH_2\text{-}R''' \quad (XIII)}$ (Ig)
or its reactive
derivative at the
carboxy group
or a salt thereof -continued or its reactive
derivative at
the amino group
or a salt thereof

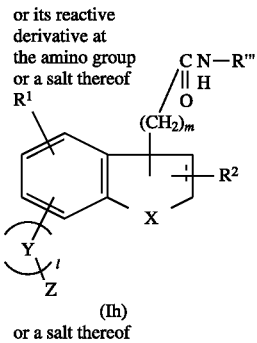

(Ih)
or a salt thereof

Process 8

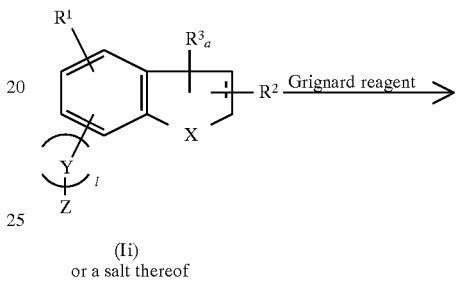 $\xrightarrow{\text{Grignard reagent}}$ (Ii)
or a salt thereof

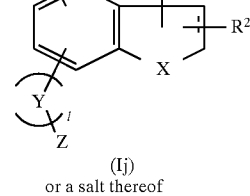

(Ij)
or a salt thereof

Process 9

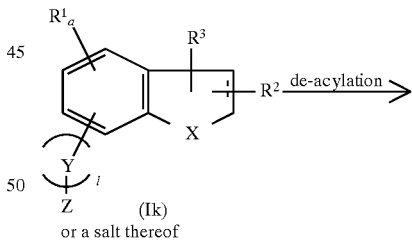 $\xrightarrow{\text{de-acylation}}$ (Ik)
or a salt thereof

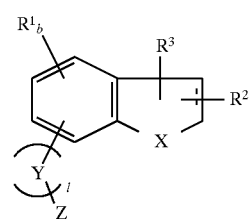

(Il)
or a salt thereof

Process 10

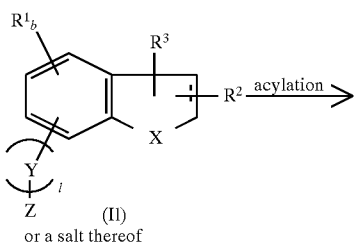
(II)
or a salt thereof

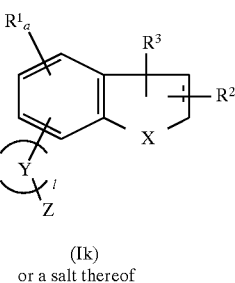
(Ik)
or a salt thereof

Process 11

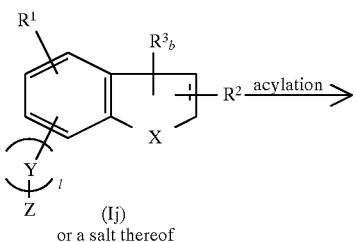
(Ij)
or a salt thereof

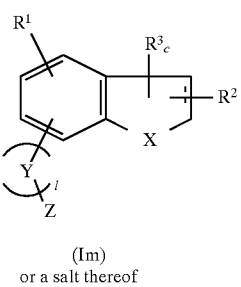
(Im)
or a salt thereof wherein
R$^1$, R$^2$, R$^3$, X, Y, Z,  and l are each as defined above,
R$_a^1$ is acylamino,
R$_b^1$ is amino,
R$_a^3$ is lower alkyl substituted with oxo,
R$_b^3$ is hydroxy(lower)alkyl,
R$_c^3$ is acyloxy(lower)alkyl,
E is lower alkylene, lower alkenylene or a group of the formula:

$$-\underset{\underset{O}{\|}}{C}-,$$

R' is hydrogen or lower alkyl,
R'' is leaving group,

R''' is lower alkyl, cyclo(lower)alkyl, lower alkyl substituted with heterocyclic group which may have one or more suitable substituent(s), lower alkoxy(lower)alkyl, hydroxy(lower)alkyl, amino, heterocyclic group, carboxy(lower)alkyl, protected carboxy(lower)alkyl, lower alkyl substituted with aryl which may have one or more suitable substituent(s) or arylsulfonyl, G$^1$ is —COOH or —SO$_3$H,
G$^2$ is —CO— or —SO$_2$—,
X' is halogen,
m is an integer of 0 to 6, and
b, r, q and u are each an integer of 0 or 1.

Suitable pharmaceutically acceptable salts of the object compound (I) are conventional non-toxic salts and may include a salt with a base or an acid addition salt such as a salt with an inorganic base, for example, an alkali metal salt (e.g., sodium salt, potassium salt, etc.), an alkaline earth metal salt (e.g., calcium salt, magnesium salt, etc.), an ammonium salt; a salt with an organic base, for example, an organic amine salt (e.g., triethylamine salt, pyridine salt, picoline salt, ethanolamine salt, triethanolamine salt, dicyclohexylamine salt, N,N'-dibenzylethylenediamine salt, etc.); an inorganic acid addition salt (e.g., hydrochloride, hydrobromide, sulfate, phosphate, etc.); an organic carboxylic or sulfonic acid addition salt (e.g., formate, acetate, trifluoroacetate, maleate, tartrate, fumarate, methanesulfonate, benzenesulfonate, toluenesulfonate, etc.); a salt with a basic or acidic amino acid (e.g., arginine, aspartic acid, glutamic acid, etc.).

In the above and subsequent descriptions of the present specification, suitable examples and illustration of the various definitions which the present invention intends to include within the scope thereof are explained in detail as follows.

The term "lower" is used to intend a group having 1 to 6 carbon atom(s), unless otherwise provided.

The term "higher" is used to intend a group having 7 to 20 carbon atoms, unless otherwise provided.

Suitable example of "one or more" may be the number of 1 to 6, in which the preferred one may be the number of 1 to 4.

Suitable "lower alkyl" and "lower alkyl moiety" may include straight or branched one having 1 to 6 carbon atom(s), such as methyl, ethyl, propyl, isopropyl, butyl, isobutyl, sec-butyl, tert-butyl, pentyl, 3-pentyl, isopentyl, tert-pentyl, neopentyl, hexyl, isohexyl, and the like, preferably one having 1 to 5 carbon atom(s).

Suitable "lower alkenyl" and "lower alkenyl moiety" may include vinyl, 1-(or 2-)propenyl, 1-(or 2- or 3-)butenyl, 1-(or 2- or 3- or 4-)pentenyl, 1-(or 2- or 3- or 4- or 5-)-hexenyl, methylvinyl, ethylvinyl, 1-(or 2- or 3-)methyl-1-(or 2-)propenyl, 1-(or 2- or 3-)ethyl-1-(or 2-)propenyl, 1-(or 2-or 3- or 4-)methyl-1-(or 2- or 3-)butenyl, and the like, in which more preferable example may be (C$_2$–C$_4$)alkenyl, and the most preferred one may be methylvinyl.

Suitable "lower alkoxy" may include methoxy, ethoxy, propoxy isopropoxy, butoxy, isobutoxy, t-butoxy, pentyloxy, t-pentyloxy, hexyloxy and the like.

Suitable "aryl" and "aryl moiety" may include phenyl, naphthyl, anthryl and the like.

Suitable "leaving group" may include acid residue and the like, and suitable examples of "acid residue" may be halogen (e.g., fluorine, chlorine, bromine, iodine.), acyloxy [e.g., sulfonyloxy (e.g., phenylsulfonyloxy, tosyloxy, mesyloxy, etc.), lower alkanoyloxy (e.g., acetyloxy, propionyloxy, etc.), etc.], lower alkyl (e.g., methyl, ethyl propyl, isopropyl, butyl, isobutyl, t-butyl, pentyl, neopentyl, t-pentyl, hexyl, etc.), aryl (e.g., phenyl, naphthyl, anthryl, etc.), ar(lower) alkyl such as phenyl(lower)alkyl (e.g., benzyl, phenethyl, phenylpropyl, etc.), di(lower)alkylamino (e.g., dimethylamino, diethylamino, diisopropylamino, ethylmethylamino, isopropylmethylamino, ethylmethylamino, ethylpropylamino, etc.), lower alkyl (lower)alkoxyamino(e.g., methylmethoxyamino, methylethylamino, ethylmethoxyamino, ethylethoxyamino, etc.) or the like.

Suitable "acid residue" may include halogen (e.g., fluorine chlorine, bromine, iodine, etc.), acyloxy [e.g., sulfonyloxy (e.g., phenylsulfonyloxy, tosyloxy, mesyloxy, etc.), lower alkanoyloxy (e.g., acetyloxy, propionyloxy, etc.), etc.] and the like.

Suitable "lower alkylene" may include straight or branched one such as methylene, ethylene, trimethylene, tetramethylene, pentamethylene, hexamethylene, methylmethylene, ethylethylene, ethylpropylene, and the like.

Suitable "lower alkenylene" may include straight or branched one having 2 to 6 carbon atoim(s) such as vinylene, propenylene, 1-(or 2-)butenylene, 1-(or 2- or 3-)pentenylene, 1-(or 2- or 3-)hexenylene, methylvinylene, ethylvinylene, 1-(or 2- or 3-)methylpropenylene, 1-(or 2- or 3-)-ethylpropenylene, 1-(or 2- or 3- or 4-)methyl-1-(or 2-)-butenylene, and the like.

Suitable "cyclo(lower)alkyl" may include cyclopropyl, cyclobutyl, cyclopentyl, cyclohexyl and the like, in which the preferred one may be cyclo($C_4$–$C_6$)alkyl.

Suitable "halogen" and "halo" moiety may include fluorine, bromine, chlorine, and iodine.

Suitable "an acyl group" and "acyl" moiety may include carbamoyl, aliphatic acyl group and acyl group containing an aromatic ring, which is referred to as aromatic acyl, or heterocyclic ring, which is referred to as heterocyclic acyl.

Suitable example of said acyl may be illustrated as follows :

carbamoyl; carboxy; aliphatic acyl such as lower or higher
  alkanoyl (e.g., formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl, etc.); cyclo (lower)alkylcarbonyl (e.g., cyclopropylcarbonyl, cyclobutylcarbonyl, cyclopentylcarbonyl, cyclohexylcarbonyl, etc.); protected carboxy such as commonly protected carboxy [e.g., esterified carboxy such as lower or higher alkoxycarbonyl (e.g., methoxycarbonyl, ethoxycarbonyl, propyloxycarbonyl, iso-propyloxycarbonyl, t-butoxycarbonyl, t-pentyloxycarbonyl, heptyloxycarbonyl, etc.), etc.], or the like; lower or higher alkylsulfonyl (e.g., methylsulfonyl, ethylsulfonyl, etc.); lower or higher alkoxysulfonyl (e.g., methcxysulfonyl, ethoxysulfonyl, etc.); di-(lower)alkoxyphosphoryl (e.g., dimethoxyphosphoryl, diethoxyphosphoryl, dipropoxyphosphoryl, dibutoxyphosphoryl, dipentyloxyphosphoryl, dihexyloxyphosphoryl, etc.), a group of the formulas:

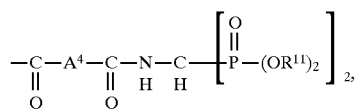

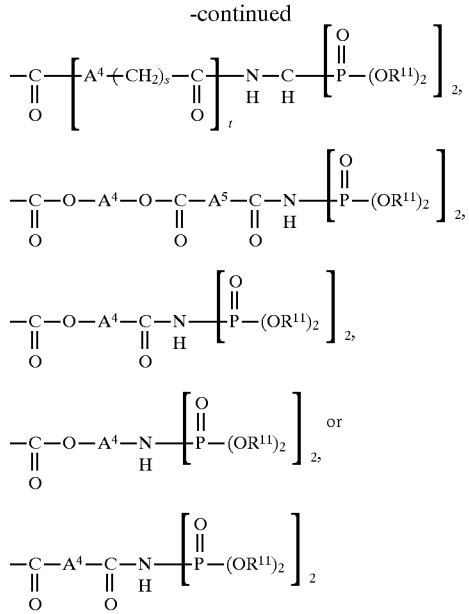

(wherein $A^4$ and $A^5$ are lower alkylene, amino(lower) alkylene or aminophenylene,
$R^{11}$ is lower alkyl or hydrogen and
S and t are each integer of 1 to 6, or the like);
aromatic acyl such as aroyl (e.g., benzoyl, toluoyl, naphthoyl, etc.); ar(lower)alkanoyl [e.g., phenyl(lower) alkanoyl (e.g., Phenylacetyl, phenylpropanoyl, phenylbutanoyl, phenylisobutanoyl, phenylpentanoyl, phenylhexanoyl, etc.), naphthyl(lower)alkanoyl (e.g., naphthylacetyl, naphthylpropanoyl, naphthylbutanoyl, etc.), etc.]; ar(lower)alkenoyl [e.g., phenyl(lower)alkenoyl (e.g., phenylpropenoyl, phenylbutenoyl, phenylmethacryloyl, phenylpentenoyl, phenylhexenoyl, etc.), naphthyl(lower) alkenoyl (e.g., naphthylpropenoyl, naphthylbutenoyl, etc.), etc.]; ar(lower)alkoxycarbonyl [e.g., phenyl(lower) alkoxycarbonyl (e.g. benzyloxycarbonyl, etc.), etc.]; aryloxycarbonyl (e.g., phenoxycarbonyl, naphthyloxycarbonyl, etc.); aryloxy(lower)alkanoyl (e.g., phenoxyacetyl, phenoxypropionyl, etc.); arylcarbamoyl (e.g., phenylcarbamoyl, etc.); arylthiocarbamoyl (e.g., phenylthiocarbamoyl, etc.); arylglyoxyloyi (e.g., phenylglyoxyloyl, naphthylglyoxyloyl, etc.); arylsulfonyl (e.g., phenylsulfonyl, p-tolylsulfonyl, etc.); or the like.
  heterocyclic acyl such as
  heterocycliccarbonyl; heterocyclic(lower)alkanoyl (e.g., heterocyclicacetyl, heterocyclicpropanoyl, heterocyclicbutanoyl, heterocyclicpentanoyl, heterocyclichexanoyl, etc.);
  heterocyclic(lower)alkenoyl (e.g., heterocyclicpropenoyl, heterocyclicbutenoyl, heterocyclicpentenoyl, heterocyclichexenoyl, etc.); heterocyclicglyoxyloyl; or the like; and the like.

Suitable "heterocyclic group" and "heterocyclic moiety" may include saturated or unsaturated monocyclic or polycyclic heterocyclic group containing at least one heteroatom such as an oxygen, sulfur, nitrogen atom and the like.

And, especially preferable one may be heterocyclic group such as
unsaturated 3 to 8-membered (more preferably 5 or 6-membered) heteromonocyclic group containing 1 to 4 nitrogen atom(s), for example, pyrrolyl, pyrrolinyl, imidazolyl, pyrazolyl, pyridyl, dihydropyridyl, pyrimidyl, pyrazinyl, pyridazinyl, triazolyl (e.g., 4H-1, 2,4-triazolyl, 1H-1,2,3-triazolyl, 2H-1,2,3-triazolyl, etc.), tetrazolyl (e.g., 1H-tetrazolyl, 2H-tetrazolyl, etc.), etc.;

saturated 3 to 8-membered (more preferably 5 or 6-membered heteromonocyclic group containing 1 to 4 nitrogen atom(s), for example, pyrrolidinyl, imidazolidinyl, piperidyl, piperazinyl, etc.;

unsaturated condensed heterocyclic group containing 1 to 4 nitrogen atom(s), for example, indolyl, isoindolyl, indolinyl, indolizinyl, benzimidazolyl, quinolyl, isoquinolyl, indazolyl, benzotriazolyl, phthalimidyl, etc.;

unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyl, etc.), etc.;

saturated 3 to 8-membered (more preferably 5 or 6-membered) heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered (more preferably 5 or 6-membered) heteromonocyclic group containing 1 to 2 sulfur atom(s) and 1 to 3 nitrogen atom(s), for example, thiazolyl, isothiazolyl, thiadiazolyl (e.g., 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 to 2 sulfur atom(s) and 1 to 3 nitrogen atom(s), for example, thiazolidinyl, etc.;

unsaturated 3 to 8-membered (more preferably 5 or 6-membered) heteromonocyclic group containing 1 to 2 sulfur atom(s), for example, thienyl, dihydrodithiinyl, dihydrodithionyl, etc.;

unsaturated condensed heterocyclic group containing 1 to 2 sulfur atom(s) and 1 to 3 nitrogen atom(s), for example, benzothiazolyl, benzothiadiazolyl, etc.;

unsaturated 3 to 8-membered (more preferably 5 or 6-membered) heteromonocyclic group containing an oxygen atom, for example, furyl, pyranyl, etc.;

saturated 3 to 8-membered (more preferably 5 or 6-membered) heteromonocyclic group containing 1 to 2 oxygen atom(s), for example, oxiranyl, oxolanyl, dioxolanyl, tetrahydrofuranyl, etc.;

unsaturated 3 to 8-membered (more preferably 5 or 6-membered) heteromonocyclic group containing an oxygen atom and 1 to 2 sulfur arom(s), for example, dihydrooxathiinyl, etc.;

unsaturated condensed heterocyclic group containing 1 to 4 oxygen atom(s), for example, methylenedioxyphenyl, benzodioxanyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example, benzoxathiinyl, etc.; and the like, and "heterocyclic group" and "heterocyclic moiety" as stated above may have one or more suitable substituent(s) such as oxo; halogen (e.g., fluorine, chlorine, bromine, iodine, etc.); lower alkanoyl (e.g., formyl, acetyl, propanoyl, butanoyl, 2-methylpropanoyl, pentanoyl, 2,2-dimethylpropanoyl, hexanoyl, etc.); aryl (e.g., phenyl, naphthyl, anthryl, etc.); lower alkyl (e.g., methyl, ethyl, propyl, isopropyl, butyl, isobutyl, sec-butyl, tert-butyl, pentyl, 3-pentyl, isopentyl, tert-pentyl, neopentyl, hexyl, isohexyl, etc.); and the like.

The acyl moiety as stated above may have one to ten, same or different, suitable substituent(s) such as lower alkyl (e.g., methyl, ethyl, propyl, etc.); lower alkoxy (e.g., methoxy, ethoxy, propoxy, etc.); lower alkylthio (e.g., methylthio, ethylthio, etc.); mono-(or di-)lower alkylamino (e.g., methylamino, ethylamino, propylamino, dimethylamino, diethylamino, dipropylamino, etc.); lower alkanoylamino (e.g., acetylamino, propionylamino, butyrylamino, pentanoylamino, hexanoylamino, etc.); cyclo(lower)alkylamino (e.g., cyclopropylamino, cyclobutylamino, cyclopentylamino, cyclohexylamino, etc.); mono-(or di-)lower alkoxy(lower)alkylamino (e.g., methoxymethylamino, methoxyethylamino, methoxypropylamino, ethoxymethylamino, ethoxyethylamino, ethoxypropylamino, etc.); hydroxy(lower)alkylamino (e.g., hydroxymethyl, hydroxyethyl, hydroxypropyl, hydroxypentyl, hydroxyhexyl, etc.); heterocyclic(lower)alkylamino, in which "heterocyclic moiety" is aforementioned "heterocyclic" moiety; heterocyclicamino which may have one or more suitable substituent(s), in which "heterocyclic" moiety is aforementioned "heterocyclic" moiety; lower alkanoyloxy (e.g., acetyloxy, propionyloxy, butyryloxy, pentanoyloxy, hexanoyloxy, etc.); heterocyclic group, in which "heterocyclic group" is aforementioned "heterocyclic group"; di-lower alkoxy(lower)alkyl (e.g., dimethoxymethyl, dimethoxyethyl, dimethoxypropyl, diethoxymethyl, diethoxyethyl, diethoxypropyl, etc.); arylamino which may have one or more suitable substituent(s) (e.g., phenylamino, dimethylaminophenylamino, trifluoromethylphenylamino, trifluoromethylnaphthylamino, trifluoromethylanthrylamino, etc.); cyano(lower)alkylamino (e.g., cyanomethylamino, cyanoethylamino, cyanopropylamino, cyanobutylamino, cyanopentylamino, cyanohexylamino, etc.); arylsulfonylamino (e.g., phenylsulfonylamino naphthylsulfonylamino, anthrylsulfonylamino, etc.); protected carboxy(lower)alkylamino (e.g., methoxycarbonylmethylamino, methoxycarbonylethylamino, ethoxycarbonylmethylamino, ethoxycarbonylethylamino, etc.); tri-halo(lower)alkylamino (e.g., 2,2,2-trifluoroethylamino, 1-(trifluoromethyl)ethylamino, 2-(trifluoromethyl)propylamino, etc.); cyclo(lower)alkyl (e.g., cyclopentyl, cyclohexyl, etc.); cyclo(lower)alkenyl (e.g., cyclohexenyl, cyclohexadienyl, etc.); halogen (e.g., fluorine, chlorine, bromine, iodine, etc.); amino, commonly protected amino as mentioned above; hydroxy; commonly protected hydroxy as mentioned below; cyano; nitro; carboxy; carboxy(lower)alkyl; commonly protected carboxy as mentioned below; sulfo; sulfamoyl; imino; oxo; hydrazino; amino(lower)alkyl (e.g., aminomethyl, aminoethyl, etc.); carbamoyloxy; hydroxy(lower)alkyl (e.g., hydroxymethyl, 1-(or 2-)hydroxyethyl, 1-(or 2- or 3-)hydroxypropyl, etc.), or the like.

Suitable "hydroxy protective group" in the term commonly "protected hydroxy" may include acyl as mentioned above, phenyl(lower)alkyl which may have one or more suitable substituent(s) (e.g., benzyl, 4-methoxybenzyl, trityl, etc.), trisubstituted silyl [e.g., tri(lower)alkylsilyl (e.g., trimethylsilyl, t-butyldimethylsilyl, etc.), etc.], tetrahydropyranyl and the like.

Suitable commonly "protected carboxy" may include esterified carboxy and the like. And suitable example of said ester may be the ones such as lower alkyl ester (e.g., methyl ester, ethyl ester, propyl ester, isopropyl ester, butyl ester, isobutyl ester, t-butyl ester, pentyl ester, t-pentyl ester, hexyl ester, etc.); lower alkenyl ester (e.g., vinyl ester, allyl ester, etc.); lower alkynyl ester (e.g., ethynyl ester, propynyl ester, etc.); lower alkoxy(lower)alkyl ester (e.g., methoxymethyl ester, ethoxymethyl ester, isopropoxy ester, 1-methoxyethyl ester, 1-ethoxyethyl ester, etc.); lower alkylthio(lower)alkyl ester (e.g., methylthiomethyl ester, ethylthiomethyl ester, ethylthioethyl ester, isopropoxythiomethyl ester, etc.); mono-(or di- or tri-)halo(lower)alkyl ester (e.g., 2-iodoethyl ester, 2,2,2-trichloroethyl ester, etc.); lower alkanoyloxy (lower)alkyl ester (e.g., acetoxymethyl ester, propionyloxymethyl ester, butyryloxymethyl ester, valeryloxymethyl ester, pivaloyloxymethyl ester, hexanoyloxymethyl ester, 1-acetoxyethyl ester, 2-acetoxyethyl ester, 2-propionyloxyethyl ester, etc.); lower alkoxycarbonyloxy (lower)alkyl ester (e.g., methoxycarbonyloxymethyl ester, ethoxycarbonyloxymethyl ester, propoxycarbonyloxymethyl ester, 1-(or 2-)[methoxycarbonyloxy]ethyl ester, 1-(or 2-)[Lethoxycarbonyloxy]ethyl ester, 1-(or 2-) [propoxycarbonyloxy]ethyl ester, 1-(or 2-) [isopropoxycarbonyloxy]ethyl ester, etc.); lower alkanesulfonyl(lower)alkyl ester (e.g., mesylmethyl ester, 2-mesyethyl ester, etc.); lower alkoxycarbonyloxy(lower) alkyl ester (e.g., methoxycarbonyloxymethyl ester, ethoxycarbonyloxymethyl ester, propoxycarbonyloxymethyl ester, t-butoxycarbonyloxymethyl ester, 1-(or 2-)methoxycarbonyloxyethyl ester, 1-(or 2-)ethoxycarbonyloxyethyl ester, 1-(or 2-)propoxycarbonyloxyethyl ester, 1-(or 2-)isopropoxycarbonyloxyethyl ester, etc.); phthalidylidene (lower)alkyl ester, or (5-lower alkyl-2-oxo-1,3-dioxol-4-yl) (lower)alkyl ester [e.g., (5-methyl-2-oxo-1,3-dioxol-4-yl) methyl ester, (5-ethyl-2-oxo-1,3-dioxol-4-yl)methyl ester, (5-propyl-2-oxo-1,3-dioxol-4-yl)ethyl ester, etc.]; ar(lower) alkyl ester, for example, phenyl(lower)alkyl ester which may have one or more suitable substituent(s) (e.g., benzyl ester, 4-methoxybenzyl ester, 4-nitrobenzyl ester, phenethyl ester, trityl ester, benzhydryl ester, bis(methoxyphenyl) methyl ester, 3,4-dimethoxybenzyl ester, 4-hydroxy-3,5-di-t-butylbenzyl ester, etc.); aryl ester which may have one or more suitable substituent(s) such as substituted or unsubstituted phenyl ester (e.g., phenyl ester, tolyl ester, t-butylphenyl ester, xylyl ester, mesityl ester, cumenyl ester, 4-chlorophenyl ester, 4-methoxyphenyl ester, etc.); tri (lower)alkyl silyl ester; lower alkylthioester (e.g., methylthioester, ethylthioester, etc.) and the like.

The preferred examples of "an acyl group" may be carboxy protected carboxy, carbamoyl, lower alkanoyl, lower alkylsulfonyl, aroyl, heterocyclic carbonyl which may have one or more suitable substituent(s), in which the more preferred one may be carboxy, $(C_1-C_4)$alkoxy carbonyl, carbamoyl, $(C_1-C_4)$alkanoyl, $(C_1-C_4)$alkylsulfonyl, benzoyl, carbonyl substituted with unsaturated 3 to 8-membered heteromonocyclic group containing 1 to 4 nitrogen atom(s), carbamoyl substituted with saturated 3 to 8-membered heteromonocyclic group containing 1 to 2 oxygen atom(s) and 1 to 3 nitrogen atom(s), carbonyl substituted with saturated 3 to 8-membered heteromonocyclic group containing 1 to 4 nitrogen atom(s) having $(C_1-C_4)$ alkyl, and the most preferred one may be carboxy, methoxycarbonyl, ethoxycarbonyl, isopropoxycarbonyl, carbamoyl, acetyl, methylsulfonyl, benzoyl, morpholinocarbonyl, N-methylpiperidylcarbonyl or pyridylcarbonyl.

Suitable "acyl" moiety in the term of "acylamino" can be referred to aforementioned "acyl" moiety.

The preferred examples of "acylamnino" may be ureido, lower alkanoylamino, lower alkoxycarbonylamino, heterocyclic carbonylamino, lower alkanoylamino(lower) alkanoylamino (e.g. acetylaminoacetylamino, acetylaminopropionylamino, propionylaminoacetylamino, propionylaminopropionylamino, etc.), mono-(or di-)lower alkylamino(lower)alkanoylamino (e.g., methylaminoacetylamino, dimethylaminoacetylamino, ethylaminoacetylamino, diethylaminoacetylamino, etc.), lower alkanoyloxy(lower)alkanoylamino [e.g., acetyloxyacetylamino, acetyloxypropionylamino, propionyloxyacetylamino, propionyloxypropionylamino, etc.), heterocyclic(lower)alkanoylamino (e.g., heterocyclic-carbonylamino, heterocyclic-acetylamino, heterocyclic-propionylamino, etc.), lower alkoxy(lower)alkanoylamino (e.g., methoxyacetylamino, ethoxyacetylamino, methoxypropionylamino, ethoxypropionylamino, etc.), hydroxy(lower)alkanoylamino (e.g., hydroxyacetylamino, hydroxypropionylamino, etc.), lower alkylsulfonylamino (e.g., methylsulfonylamino, ethylsulfonylamino, propylsulfonylamino, butylsulfonylamino, pentylsulfonylamino, hexylsulfonylamino, etc.), or mono-(or di-)lower alkoxy(lower)alkylamino(lower)-alkanoylamino (e.g., methoxymethylaminoacetylamino, bis (methoxymethyl)aminoacetylamino, methoxyethylaminoacetylamino, bis(methoxyethyl) aminoacetylamino, etc.), in which the more preferred one may be ureido, $(C_1-C_4)$alkanoylamino, $(C_1-C_4)$-alkoxycarbonylamino, carbonylamino substituted with saturated 3 to 8-membered heteromonocyclic group containing 1 to 2 oxygen atom(s) and 1 to 3 nitrogen atom(s), $(C_1-C_4)$-alkanoylamino $(C_1-C_4)$alkanoylamino, di$(C_1-C_4)$ alkylamino-$(C_1-C_4)$ alkanoylamino, $(C_1-C_4)$alkanoyloxy $(C_1-C_4)$alkanoylamino, $(C_1-C_4)$alkanoylamino substituted with saturated 3 to 8-membered heteromonocyclic group containing 1 to 2 oxygen atom(s) and 1 to 3 nitrogen atom(s), $(C_1-C_4)$alkoxy$(C_1-C_4)$-alkanoylamino, hydroxy $(C_1-C_4)$alkanoylamino, $(C_1-C_4)$-alkylsulfonylamino or bis [$(C_1-C_4)$alkoxy(Cl-$C_4$)alkyl]amino $(C_1-C_4)$alkanoylamino and the most preferred one may be ureido, acetylamino, t-butoxycarbonylamino, morpholinocarbonylamino, acetylaminoacetylamino, dimethylaminoacetylamino, acetyloxyacetylamino, morpholinoacetylamino, methoxyacetylamino, hydroxyacetylamino, methylsulfonylamino or dimethoxyethylaminoacetylamino.

Suitable "hydroxy(lower)alkyl" may be hydroxymethyl, 1-(or 2-)hydroxyethyl, 1-hydroxy-1-methylethyl, 2-hydroxypropyl, 1-hydroxy-1-ethylethyl, 1-hydroxy-1-ethylpropyl, 1-hydroxybutyl, 1-(or 2- or 3-)hydroxy-1-(or 2- or 3-)methylpropyl, 1-(or 2- or 3- or 4-)hydroxy-1-(or 2- or 3- or 4-)methylbutyl, 1-(or 2- or 3- or 4- or 5-)hydroxy-1-(or 2- or 3- or 4- or 5-)methylpentyl, 1-(or 2- or 3- or 4- or 5- or 6-)hydroxy-1-(or 2- or 3- or 4- or 5- or 6-)-methylhexyl, or the like.

The preferred examples of "hydroxy(lower)alkyl" may be hydroxy($C_1-C_5$)alkyl, and the most preferred one may be hydroxymethyl, 1-hydroxyethyl, 1-hydroxy-1-methylethyl, 1-hydroxy-1-ethylpropyl, 1-hydroxybutyl, 2-hydroxyethyl, 3-hydroxy-3-methylbutyl, 1-hydroxybutyl, 2-hydroxypropyl or 2-hydroxy-2-methylpropyl.

The preferred examples of "suitable substituent(s)" in the term of "hydroxy(lower)alkyl which may have one or more suitable substituent(s)" may be mono-(or di- or tri-)-halo (lower)alkyl, protected carboxy, hydroxy, aryl, cyclo(lower) alkyl or heterocyclic group, in which the preferred one may be tri-halo($C_1$–$C_4$)alkyl, ($C_1$–$C_4$)-alkoxycarbonyl, hydroxy, phenyl, cyclo($C_3$–$C_6$)alkyl, or unsaturated heteromonocyclic group consisting of 1 to 4 nitrogen atom(s), and the most preferred one may be trifluoromethyl, ethoxycarbonyl, hydroxy, phenyl, cyclohexyl or pyridyl.

Suitable "acyl" moiety in the term of "acyl(lower)alkyl" can be referred to aforementioned "acyl" moiety.

The preferred examples of "acyl(lower)alkyl" may be carboxy(lower)alkyl, protected carboy(lower)alkyl, carbamoyl(lower)alkyl, lower alkanoyl(lower)alkyl, aroyl (lower)alkyl, carbonyl(lower)alkyl substituted with heterocyclic group which may have one or more suitable substituent(s), lower alkyl having

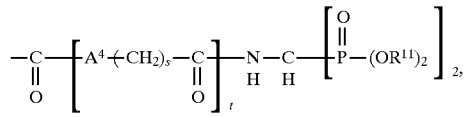

(wherein $A^4$ is lower alkylene, amino lower alkylene or aminophenylene, $R^{11}$ is lower alkyl or hydrogen, and s and t are each integer of 1 to 6), (mono- or di-)lower alkylamino)carbonyl(lower)alkyl which may have one or more suitable substituent(s) (e.g., methylaminocarbonylmethyl, dimethylaminocarbonylmethyl, methylaminocarbonylethyl, 2-dimethylaminocarbonylethyl, trifluoromethylaminocarbonylmethyl, trifluoroethylaminocarbonylmethyl, cyanomethylaminocarbonylmethyl, cyanoethylcarbonylmethyl, cyanomethylcarbonylethyl, etc.), cyclo(lower)alkylaminocarbonyl(lower)alkyl (e.g. cyclopropylaminocarbonylmethyl, cyclobutylaminocarbonylmethyl, cyclopentylaminocarbonylmethyl, cyclohexylaminocarbonylmethyl, etc.), lower alkoxy(lower)alkylaminocarbonyl(lower)alkyl (e.g., methoxymethylaminocarbonylmethyl, methoxyethylaminocarbonylmethyl, bis (methoxymethylamino)carbonylmethyl, bis (methoxyethylamino)carbonylmethyl, etc.), di-(lower) alkoxyphosphoryl (e.g., dimethoxyphosphoryl, diethoxyphosphoryl, dipropoxyphosphoryl, dibutoxyphosphoryl, dipentyloxyphosphoryl, dihexyloxyphosphoryl, etc.), mono-(or di-)hydroxy(lower) alkylaminocarbonyl(lower)alkyl (e.g., hydroxymethylaminocarbonylmethyl, hydroxyethylaminocarbonylmethyl, dihydroxymethylaminocarbonylmethyl, dihydroxyethylaminocarbonylmethyl, etc.), aminocarbonyl (lower)alkyl substituted with heterocyclic group which may have one or more suitable substituent(s) (e.g. thiazolylaminocarbonylmethyl, pyridylaminocarbonylmethyl, morpholinoaminomethyl, methyloxadiazolylaminocarbonylmethyl, trifluorothiadiazolylaminocarbonylmethyl, etc.), heterocyclic(lower)alkylaminocarbonyl(lower)alkyl (e.g., pyridylmethylaminocarbonylmethyl, tetrahydrofuranylmethylaminocarbonvlmethyl, etc.), hydrazinocarbonyl(lower)alkyl (e.g., hydrazinocarbonylmethyl, hydrazinocarbonylethyl, hydrazinocarbonylpropyl, etc.), aminocarbonyl(lower)alkyl substituted with aryl which may have one or more suitable substituent(s) (e.g., dimethylaminophenylaminocarbonylmethyl, trifluoromethylphenylaminocarbonylmethyl, etc.), cyano (lower)alkylaminocarbonyl(lower)alkyl (e.g., cyanomethylaminocarbonylmethyl, cyanoethylaminocarbonylmethyl, cyanomethylaminocarbonylethyl, cyanoethylaminocarbonylethyl, etc.), arylsulfonylaminocarbonyl(lower)alkyl (e.g., phenylsulfonylaminocarbonylmethyl, phenylsulfonylaminocarbonylethyl, phenylsulfonylaminocarbonylpropyl, etc.), protected carboxy(lower)alkylaminocarbonyl(lower)alkyl (e.g. methoxycarbonylmethylaminocarbonylmethyl, ethoxycarbonylmethylaminocarbonylmethyl, methoxycarbonylmethylaminocarbonylethyl, ethoxycarbonylmethylaminocarbonylethyl, etc.), in which the preferred one may be ($C_1$–$C_4$)alkoxycarbonyl-($C_1$–$C_4$) alkyl, ($C_1$–$C_4$)alkanoyl($C_1$–$C_4$)alkyl, carbamoyl-($C_1$–$C_4$) alkyl, carboxy($C_1$–$C_4$)alkyl, lower alkyl having

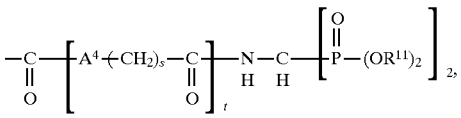

(wherein $A^4$ is ($C_1$–$C_6$)alkylene, amino($C_1$–$C_6$)alkylene or aminophenylene, $R^{11}$ is ($C_1$–$C_6$)alkyl or hydrogen, and s and t are each integer of 1 to 6), carbonyl($C_1$–$C_4$)alkyl substituted with heterocyclic group which may have 1 to 3 suitable substituent(s), mono-(or di-)($C_1$–$C_4$)alkylaminocarbonyl($C_1$–$C_4$)alkyl which may have 1 to 3 suitable substituent(s), cyclo($C_3$–$C_6$) alkylaminocarbonyl($C_1$–$C_4$)alkyl, ($C_1$–$C_4$)alkoxy($C_1$–$C_4$) alkylaminocarbonyl($C_1$–$C_4$)alkyl, di-($C_1$–$C_4$) alkoxyphosphoryl($C_1$–$C_4$)alkyl, mono-(or di-)hydroxy ($C_1$–$C_4$)alkylaminocarbonyl($C_1$–$C_4$)alkyl, aminocarbonyl ($C_1$–$C_4$)alkyl substituted with heterocyclic group which may have 1 to 3 suitable substituent(s), heterocyclic($C_1$–$C_4$) alkylaminocarbonyl($C_1$–$C_4$)alkyl, hydrazinocarbonyl ($C_1$–$C_4$)alkyl, aminocarbonyl($C_1$–$C_4$)alkyl substituted with phenyl which may have 1 to 3 suitable substituent(s), cyano($C_1$–$C_4$)alkylaminocarbonyl($C_1$–$C_4$)alkyl, phenylsulfonylaminocarbonyl($C_1$–$C_4$)alkyl, ($C_1$–$C_4$) alkoxycarbonyl($C_1$–$C_4$)alkylaminocarbonyl($C_1$–$C_4$)alkyl, and the most preferred one may be carboxymethyl, carboxyethyl, methoxycarbonylethyl, ethoxycarbonylmethyl, ethoxycarbonylethyl, benzoylmethyl, carbamoylmethyl, acetylmethyl, t-butoxycarbonylmethyl, morpholinocarbonylmethyl, pyridylcarbonylmethyl, chlorothienylcarbonylmethyl, pyrrolinylcarbonylmethyl, acetylpiperazinylcarbonylmethyl, phenylpiperazinylcarbonylmethyl, methylpiperazinylcarbonylmethyl, dimethylaminocarbonylmethyl, dimethylaminocarbonylethyl, trifluoromethylmethylaminocarbonylmethyl, cyanomethylaminocarbonylmethyl, cyclopentylaminocarbonylmethyl, methoxyethylaminocarbonylmethyl, dimethoxyethylaminocarbonylmethyl, dimethoxyphosphorylmethyl, diethoxyphosphorylmethyl, hydroxyethylaminocarbonylmethyl, dihydroxyethylaminocarbonylmethyl, trifluoromethylthiadiazolylaminocarbonylmethyl, thiazolylaminocarbonylmethyl, pyridylaminocarbonylmethyl, morpholinoaminocarbonylmethyl, pyridyl-N- methylaminocarbonylmethyl, methyloxadiazolylaminocarbonylmethyl, pyridylmethylaminocarbonylmethyl, tetrahydrofuranylmethylaminocarbonylmethyl, hydrazinocarbonylmethyl, dimethylaminophenylaminocarbonylmethyl, trifluoromethylphenylaminocarbonylmethyl, cyanomethylaminocarbonylmethyl, phenylsulfonylaminocarbonylmethyl or ethoxycarbonylmethylaminocarbonylmethyl.

The preferred examples of "mono-(or di- or tri-)-halo (lower)alkyl" may be fluoromethyl, difluoromethyl, trifluoromethyl, chloromethyl, dichloromethyl, trichloromethyl, bromomethyl, dibromomethyl, tribromomethyl, 1-(or 2-)fluoroethyl, 1-(or 2-)bromoethyl, 1-(or 2-)chloroethyl, 1,1-difluoroethyl, 2,2-difluoroethyl, or the like, in which the preferred one may be mono-(or di- or tri-)halo($C_1$–$C_4$)alkyl, and the most preferred one may be difluoromethyl or trifluoromethyl.

The preferred examples of "lower alkylthio" may be methylthio, ethylthio, propylthio, butylthio, pentylthio, hexylthio, or the like, in which the preferred one may be ($C_1$–$C_4$)alkylthio, and the most preferred one may be methylthio.

The preferred examples of "cyclo(lower)alkyl(lower)alkyl" may be cyclopropylmethyl, cyclobutylmethyl, cyclopentylmethyl, cyclohexylmethyl, cyclopropylethyl, cyclobutylethyl, cyclopentylethyl, cyclohexylethyl, or the like, in which the preferred one may be cyclo($C_3$–$C_6$)alkyl ($C_1$–$C_4$)alkyl, and the most preferred one may be cyclohexylmethyl.

Suitable "acylamino" moiety in the term of "acylamino-(lower) alkyl" can be referred to aforementioned "acylamino".

The preferred examples of "acylamino(lower)alkyl" may be lower alkoxycarbonylamino(lower)alkyl, lower alkanoylamino(lower)alkyl, heterocyclic-carbonylamino-(lower)alkyl,

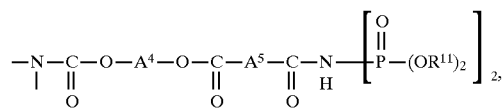

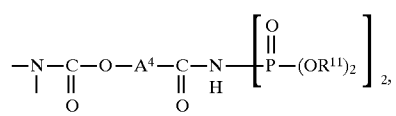

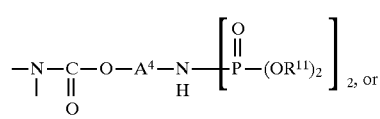

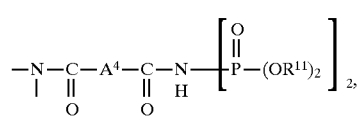

(wherein $A^4$ and $A^5$ are each lower alkylene, amino(lower) alkylene or aminophenylene, and $R^{11}$ is lower alkyl or hydrogen), in which the preferred one may be ($C_1$–$C_4$) alkoxycarbonylamino-($C_1$–$C_4$)alkyl, ($C_1$–$C_4$)alkanoylamino ($C_1$–$C_4$)alkyl, carbonylamino($C_1$–$C_4$)alkyl substituted with saturated 3 to 8-membered heteromonocyclic group containing 1 to 2 oxygen atom(s) and 1 to 3 nitrogen atom(s),

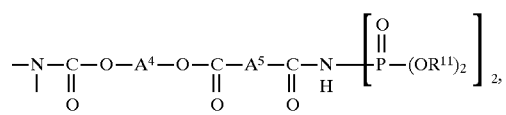

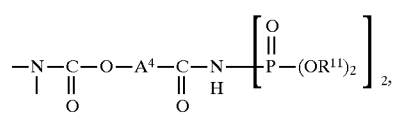

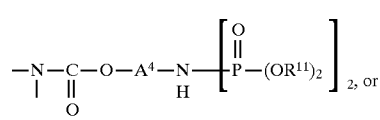

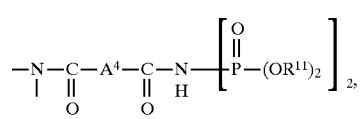

(wherein $A^4$ and $A^5$ are each ($C_1$–$C_6$)alkylene, amino ($C_1$–$C_6$)-alkylene or aminophenylene, and $R^{11}$ is ($C_1$–$C_6$)alkyl or hydrogen), and the most preferred one may be t-butoxycarbonyl aminomethyl, acetylaminomethyl or morpholinocarbonylaminomethyl.

Suitable "acyl" moiety in the terms of "acyl(lower)-alkenyl" can be referred to aforementioned "acyl" moiety.

Suitable "(lower)alkenyl" moiety in the term of "acyl (lower)alkenyl" can be referred to aforementioned "lower alkenyl".

The preferred examples of "acyl(lower)alkenyl" may be protected carboxy(lower)alkenyl, in which the preferred one may be ($C_1$–$C_4$)alkoxycarbonyl($C_1$–$C_4$)alkenyl, and the most preferred one may be ethoxycarbonylvinyl.

Suitable "acyl" moiety in the term of "acyloxy(lower) alkyl" can be referred to aforementioned "acyl" moiety.

The preferred examples of "acyloxy(lower)alkyl" may be lower alkanoyloxy(lower)alkyl, cyclo(lower) alkylcarbonyloxy(lower)alkyl, protected carboxyoxy(lower) alkyl, aroyloxy(lower)alkyl, or lower alkyl substituted with

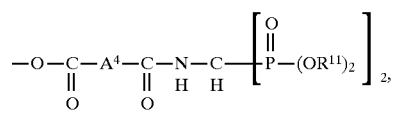

(wherein $A^4$ is lower alkylene, amino(lower)alkylene or aminophenylene, and $R^{11}$ is lower alkyl or hydrogen), in which the preferred one may be ($C_1$–$C_4$)-alkanoyloxy ($C_1$–$C_4$)alkyl, cyclo($C_3$–$C_6$)-alkylcarbamoyloxy ($C_1$–$C_4$) alkyl, ($C_1$–$C_4$)-alkoxycarbonyloxy ($C_1$–$C_4$)alkyl, benzoyloxy-($C_1$–$C_4$)alkyl, or lower alkyl substituted with

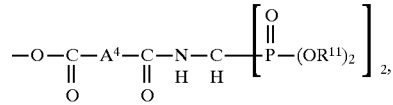

(wherein $A^4$ is ($C_1$–$C_6$)alkylene, amino($C_1$–$C_6$)alkylene or aminophenylene, and $R^{11}$ is ($C_1$–$C_6$)alkyl or hydrogen), and the most preferred one may be acetyloxymethyl, 1-acetyloxyethyl, cyclohexylcarbonyloxymethyl, ethoxycarbonyloxymethyl or benzoyloxymethyl.

Suitable "acyl" moiety in the term of "acyl(lower) alkylthio(lower)alkyl" can be referred to aforementioned "acyl" moiety.

The preferred examples of "acyl(lower)alkylthio(lower) alkyl" may be protected carboxy(lower)alkylthio(lower) alkyl, in which the preferred one may be ($C_1$–$C_4$) alkoxycarbonyl($C_1$–$C_4$)alkylthio($C_1$–$C_4$)alkyl, and the most preferred one may be ethoxycarbonylmethylthiomethyl.

The preferred examples of "amino(lower)alkyl" may be amino($C_1$–$C_4$)alkyl, in which the most preferred one may be aminomethyl.

The preferred examples of "mono-(or di-)lower alkylamino" may be methylamino, dimethylamino, ethylamino, diethylamino, propylamino, dipropylamino, butylamino, dibutylamino, pentylamino, dipentylamino, hexylamino, dihexylamino, or the like, in which the preferred one may be mono-(or di-)($C_1$–$C_4$)alkylamino, and the most preferred one may be methylamino, dimethylamino or diethylamino.

The preferred examples of "lower alkylthio(lower)alkyl" may be methylthiomethyl, methylthioethyl, methylthiopropyl, methylthiobutyl, ethylthiomethyl, ethylthioethyl, ethylthiopropyl, propylthiomethyl, propylthioethyl, propylthiopropyl, or the like, in which the preferred one may be ($C_1$–$C_4$)alkylthio($C_1$–$C_4$)alkyl, and the most preferred one may be methylthiomethyl.

The preferred examples of "hydroxyimino(lower)alkyl which may have one or more suitable substituent(s)" may be hydroxyiminomethyl, 1-hydroxyiminoethyl, hydroxyimino-1-methylethyl, hydroxyimino-1-methylpropyl, hydroxyimino-1-methylpropyl, hydroxyimino-1-aminomethyl, 2-hydroxyimino-2-amino-ethyl, hydroxyimino-1-aminopropyl, or the like, in which the preferred one may be hydroxyimino($C_1$–$C_4$)alkyl which may have amino, and the most preferred one may be 1-hydroxyiminoethyl or 2-hydroxyimino-2-aminoethyl.

The preferred examples of "hydroxy(lower)alkylthio (lower)alkyl" may be hydroxymethylthiomethyl, 2-hydroxymethylthioethyl, 2-hydroxymethylthiopropyl, 4-hydroxymethylthiobutyl, 5-hydroxymethylthiopentyl, hydroxymethylthiohexyl, (2-hydroxyethyl)thiomethyl, 2-(1-hydroxyethyl)thioethyl, (1- or 2-hydroxyethyl)thiopropyl, (1- or 2-hydroxyethyl)-thiobutyl, (1- or 2-hydroxyethyl) thiopentyl, (1- or 2-hydroxyethyl)thiohexyl, or the like, in which the preferred one may be hydroxy($C_1$–$C_4$)alkylthio ($C_1$–$C_4$)alkyl, and the most preferred one may be (2-hydroxyethyl)thiomethyl.

The preferred examples of "cyano(lower)alkyl" may be cyanomethyl, 1-(or 2-)cyanoethyl, 1-(or 2- or 3-)cyanopropyl, 1-(or 2- or 3- or 4-)cyanobutyl, 1-(or 2- or 3- or 4- or 5-)cyanopentyl, 1-(or 2- or 3- or 4- or 5- or 6-)cyanohexyl, or the like, in which the preferred one may be cyano($C_1$–$C_4$)-alkyl, and the most preferred one may be cyanomethyl or 2-cyanoethyl.

Suitable "mono-(or di-)lower alkoxy(lower)alkyl" may be methoxymethyl, methoxyethyl, dimethoxymethyl, dimethoxyethyl, ethoxymethyl, ethoxyethyl, diethoxymethyl, diethoxyethyl, propoxymethyl, propoxyethyl, propoxypropyl, dipropoxymethyl, dipropoxyethyl, dipropoxypropyl, or the like, in which the preferred one may be mono-(or di-)($C_1$–$C_4$)alkoxy($C_1$–$C_4$) alkyl, and the most preferred one may be methoxymethyl, 2-methoxyethyl or 3-diethoxypropyl.

The preferred examples of "mono-(or di-)lower alkoxy (lower)alkyl which may have one or more suitable substituent(s)" may be ($C_1$–$C_4$)alkoxy($C_1$–$C_4$)alkyl or trihalo($C_1$–$C_4$)alkyl($C_1$–$C_4$)alkoxy($C_1$–$C_4$)alkyl, and the most preferred one may be methoxymethyl, 2-methoxyethyl, 3-diethoxypropyl or trifluoromethylmethoxymethyl.

Suitable "lower alkyl substituted with aryl" may be benzyl, phenethyl, 2-phenylpropyl, naphthylmethyl, naphthylethyl, anthrylmethyl, 1-anthrylethyl, or the like, in which the more preferred one may be phenyl($C_1$–$C_4$)alkyl, naphthyl($C_1$–$C_4$)alkyl or anthryl($C_1$–$C_4$)alkyl, and the most preferred one may be benzyl.

The preferred examples of "lower alkyl substituted with aryl which may have one or more suitable substituent(s)" may be the one which may have 1 to 3 nitro or cyano, such as phenyl($C_1$–$C_4$)alkyl, nitrophenyl($C_1$–$C_4$)alkyl or cyanophenyl($C_1$–$C_4$)alkyl, in which the most preferred one may be benzyl, 4-nitrobenzyl or 3-cyanobenzyl.

The preferred examples of "mono-(or di-)lower alkylamino(lower)alkyl" may be mono-(or di-)($C_1$–$C_4$) alkylamino($C_1$–$C_4$)alkyl, in which the more preferred one may be dimethylaminomethyl.

Suitable "heterocyclic group" moiety in the term of "lower alkyl substituted with heterocyclic group which may have one or more suitable substituent(s)" can be referred to aforementioned "heterocyclic group".

The preferred examples of "lower alkyl substituted with heteocyclic group which may have one or more suitable substituent(s)" may be imidazolyl(lower)alkyl, pyridyl (lower)alkyl, morpholino(lower)alkyl, pyrrolidinyl(lower) alkyl, tetrazolyl(lower)alkyl, oxiranyl(lower)alkyl, lower alkyl substituted with methylenedioxyphenyl having halogen, lower alkyl substituted with piperazine having (lower)alkyl, lower alkyl substituted with oxadiazole having (lower)alkyl, in which the more preferred one may be imidazolyl($C_1$–$C_4$)alkyl, pyridyl($C_1$–$C_4$)-alkyl, morpholino ($C_1$–$C_4$)alkyl, pyrrolidinyl($C_1$–$C_4$)alkyl, tetrazolyl($C_1$–$C_4$) alkyl, oxiranyl($C_1$–$C_4$)alkyl, ($C_1$–$C_4$)alkyl substituted with methylenedioxyphenyl having halogen, ($C_1$–$C_4$)alkyl substituted with piperazine having ($C_1$–$C_4$)alkyl, ($C_1$–$C_4$)alkyl substituted with oxadiazole having ($C_1$–$C_6$)-alkyl, and the most preferred one may be imidazolylmethyl, pyridylmethyl, 3-pyridylpropyl, morpholinomethyl, 2-morpholinoethyl, 2-pyrrolidinylethyl, tetrazolylmethyl, oxiranylmethyl, chloromethylenedioxyphenylmethyl, N-methylpiperazinylpropyl, 5-methyloxadiazolylmethyl.

Suitable "heterocyclic group" moiety in the term of "heterocyclic group which may have one or more suitable substituent(s)" can be referred to aforementioned "heterocyclic group".

The preferred examples of "heterocyclic group which may have one or more suitable substituent(s)", may be pyridyl which may have 1 to 3 substituent(s) selected from the group consisting of halogen and lower alkyl, thiazolyl which may have 1 to 3 lower alkanoylamino, benzothienyl which may have 1 to 3 halogen, indolyl which may have 1 to 3 substituent(s) selected from the group consisting of halogen and lower alkyl, oxazolyl which may have 1 to 3 lower alkyl, pyranyl which may have 1 to 3 substituent(s) selected from the group consisting of lower alkyl and oxo, pyrrolyl which may have 1 to 3 lower alkyl, phthalimido which may have nitro, phthalimidine which may have nitro, piperidyl which may have 1 to 3 lower alkyl.

Suitable "heterocyclic" moiety in the term of "heterocyclicthio(lower)alkyl" can be referred to aforementioned to "heterocyclic group".

The preferred examples of "heterocyclicthio(lower)alkyl" may be imidazolylthio(lower)alkyl, pyridylthio(lower)alkyl or benzimidazolylthio(lower)alkyl, in which the preferred one may be imidazolylthio($C_1$–$C_4$)alkyl or benzimidazolyl ($C_1$–$C_4$)-alkyl, and the most preferred one may be imidazolylthiomethyl or benzimidazolylmethyl.

Suitable "heterocyclic" moiety in the term of "heterocyclicthio" can be referred to aforementioned "heterocyclic group".

The preferred examples of "heterocyclicthio" may be pyridylthio.

Suitable "heterocyclic" moiety in the term of "heterocyclic oxy" can be referred to aforementioned "heterocyclic group".

The preferred examples of "heterocyclic oxy" may be pyridyloxy.

Suitable "heterocyclic" moiety in the term of "heterocyclic oxy(lower)alkyl" can be referred to aforementioned "heterocyclic group".

The preferred examples of "heterocyclic oxy(lower)alkyl" may be pyridyloxy(lower)alkyl, in which the more preferred one may be pyridyloxy($C_1$–$C_4$)alkyl, and the most preferred one may be pyridyloxymethyl.

Suitable "heterocyclic" moiety in the term of "heterocyclic aminoimino(lower)alkyl" can be referred to aforementioned "heterocyclic group".

The preferred examples of "heterocyclic aminoimino (lower)alkyl" may be aminoimino(lower)alkyl substituted with unsaturated 3 to 8-membered heteromonocyclic group containing 1 to 4 nitrogen atom(s), in which the more preferred one may be pyridylaminoimino($C_1$–$C_4$)alkyl, and the most preferred one may be 2-pyridylaminoiminopropyl.

The preferred examples of "suitable substituent(s)" in the terms of "lower alkylene which may have one or more suitable substituent(s)" and "lower alkenylene which may have one or more suitable substituent(s)" may be lower alkyl, hydroxy, oxo, or the like, in which the preferred one may be ($C_1$–$C_4$)alkyl, hydroxy or oxo, and the most preferred one may be methyl, hydroxy or oxo.

The preferred examples of "suitable substituent(s)" in the terms of "aryl which may have one or more suitable substituent(s)" may be halogen, lower alkyl, nitro, lower alkoxy, an acyl group, cyclo(lower)alkyl, mono-(or di- or tri-)halo(lower)alkyl, acylamino, aryl, amino, mono-(or di-) lower alkylamino, aryloxy, acyl(lower)alkyl, hydroxy, hydroxy(lower)alkyl which may have one or more suitable substituent(s), heterocyclic group which may have one or more suitable substituent(s), mono-(or di-)lower alkylamino (lower)alkyl or acyl(lower)alkyl.

The preferred examples of "mono-(or di-)lower alkylamino(lower)alkyl" may be mono-(or di-)($C_1$–$C_4$) alkylamino($C_1$–$C_4$)alkyl, in which the preferred one may be di($C_1$–$C_4$)alkylamino($C_1$–$C_4$)alkyl, and the most preferred one may be dimethylaminomethyl.

Suitable "acyl" moiety in the term of "acyl(lower)alkoxy" can be referred to aforementioned "acyl" moiety.

The preferred examples of "acyl(lower)alkoxy" may be protected carboxy(lower)alkoxy, in which the more preferred one may be ($C_1$–$C_4$)alkoxycarbonyl($C_1$–$C_4$)alkoxy, and the most preferred one may be ethoxycarbonylmethoxy.

The preferred examples of "suitable substituent(s)" in the term of "naphthyl which may have one or more suitable substituent(s)" may be lower alkoxy, in which the more preferred one may be ($C_1$–$C_4$)alkoxy, and the most preferred one may be methoxy.

Suitable "acyl" moiety in the term of "acyl(lower) alkenyl" can be referred to aforementioned "acyl" moiety.

Suitable "(lower)alkenyl" moiety in the term of "acyl (lower)alkenyl" can be referred to aforementioned "lower alkenyl".

The preferred examples of "acyl(lower)alkenyl" may be protected carboxy($C_2$–$C_6$)alkenyl, in which the more preferred one may be lower alkoxycarbonyl($C_2$–$C_4$)alkenyl, and the most preferred one may be ethoxycarbonylvinyl.

The preferred examples of "aryloxy" may be phenoxy, naphthyloxy, anthryloxy, or the like, in which the most preferred one may be phenoxy.

The preferred examples of "aryl(lower)alkoxy" may be phenyl($C_1$–$C_6$)alkoxy, naphthyl($C_1$–$C_6$)alkoxy, anthryl ($C_1$–$C_6$)-alkoxy, or the like, in which the preferred one may be phenyl($C_1$–$C_4$)alkoxy, and the most preferred one may be phenylmethoxy.

The processes for preparing the object compound (I) of the present invention are explained in detail in the following.

Process 1

The compound (Ia) or a salt thereof can be prepared by reacting the compound (II) or its reactive derivative at the amino group or a salt thereof with the compound (III) or its reactive derivative at the carboxy group or sulfo group or a salt thereof.

Suitable reactive derivative at the amino group of the compound (II) may include Schiff's base type imino or its tautomeric enamine type isomer formed by the reaction of the compound (II) with a carbonyl compound such as aldehyde, ketone or the like; a silyl derivative formed by the reaction of the compound (II) with a silyl compound such as N,O-bis(trimethylsilyl)acetamide, N-trimethylsilylacetamide or the like; a derivative formed by the reaction of the compound (II) with phosphorus trichloride or phosgene, and the like.

Suitable reactive derivative of the compound (III) may include an acid halide, an acid anhydride, an activated ester, and the like. The suitable example may be an acid chloride; acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorus acid, sulfurous acid, thiosulfuric acid, alkanesulfuric acid (e.g., methanesulfonic acid, ethanesulfonic acid, etc.), sulfuric acid, alkylcarbonic acid, aliphatic carboxylic acid (e.g., pivalic acid, pentanoic acid, isopentanoic acid, 2-ethylbutyric acid, trichloroacetic acid, etc.); aromatic carboxylic acid (e.g., benzoic acid, etc.); a symmetrical acid anhydride; an activated amide with imidazole, 4-substituted imidazole, dimethylpyrazole, triazole or tetrazole; an activated ester (e.g. cyanomethyl ester, methoxymethyl ester, dimethyliminomethyl [$(CH_3)_2{}^+$ N=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenylthio ester, p-nitrophenyl thioester, p-cresyl thioester, carboxymethyl thioester, pyranyl ester, pyridyl ester, piperidyl ester, 8-quinolyl thioester, etc.); an ester with a N-hydroxy compound (e.g., N,N-dimethylhydroxylamine, 1-hydroxy-2-(1H)-pyridone, N-hydroxysuccinimide, N-hydroxybenzotriazole, N-hydroxyphthalimide, 1-hydroxy-6-chloro-lH-benzotriazole, etc.); and the like. These reactive derivatives can optionally be selected from them according to the kind of the compound (III) to be used.

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, dioxane, diethyl ether or any other solvents which do not adversely affect the reaction, or the mixture thereof.

The reaction temperature is not critical and the reaction is usually carried out under cooling to heating.

The reaction may be also carried out in the presence of an inorganic or an organic base such as an alkali metal (e.g., sodium, potassium, etc.), an alkali metal hydroxide (e.g., sodium hydroxide, potassium hydroxide, etc.), an alkali metal hydrogencarbonate (e.g., sodium hydrogencarbonate, potassium hydrogencarbonate, etc.), alkali metal carbonate (e.g., sodium carbonate, potassium carbonate, etc.), tri (lower)alkylamine (e.g., trimethylamine, triethylamine, diisopropylethylamine, etc.), alkali metal hydride (e.g., sodium hydride, etc.), alkali metal (lower)alkoxide (e.g., sodium methoxide, sodium ethoxide, etc.), pyridine, lutidine, picoline, dimethylaminopyridine, N-(lower) alkylmorpholine, N,N-di(lower)alkylbenzylamine, N,N-di (lower)alkylaniline or the like.

Process 2

The compound (Ib) or a salt thereof can be prepared by reacting the compound (IV) or its reactive derivative at the carboxy group or a salt thereof with the compound (V) or its reactive derivative at the amino group or a salt thereof.

This reaction can be carried out in a similar manner to that of the aforementioned Process 1, and therefore the reagents to be used and the reaction conditions (e.g., solvent, reaction temperature, etc.) can be referred to those of the Process 1.

Process 3

The compound (Ic) or a salt thereof can be prepared by reacting the compound (VI) or its reactive derivative at the hydroxy group or a salt thereof with the compound (VII) or a salt thereof.

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, dioxane, diethyl ether or any other solvents which do not adversely affect the reaction, or the mixture thereof.

The reaction temperature is not critical and the reaction is usually carried out under cooling to heating.

The reaction is usually carried out in the presence of an acid including Lewis acid.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, zinc halide (e.g., zinc chloride, zinc bromide, etc.), etc.] and the like.

The reaction may be also carried out in the presence of an inorganic or an organic base such as an alkali metal (e.g., sodium, potassium, etc.), an alkali metal hydroxide (e.g., sodium hydroxide, potassium hydroxide, etc.), an alkali metal hydrogencarbonate (e.g., sodium hydrogencarbonate, potassium hydrogencarbonate, etc.), alkali metal carbonate (e.g., sodium carbonate, potassium carbonate, etc.), tri (lower)alkylamine (e.g., trimethylamine, triethylamine, diisopropylethylamine, etc.), alkali metal hydride (e.g., sodium hydride, etc.), alkali metal (lower)alkoxide (e.g. sodium methoxide, sodium ethoxide, etc.), pyridine, lutidine, picoline, dimethylaminopyridine, N-(lower) alkylmorpholine, N,N-di(lower)alkylbenzylamine, N,N-di (lower)alkylaniline or the like.

When the base, the acid and/or the starting compound are in liquid, they can be used also as a solvent.

Process 4

The compound (Id) or a salt thereof can be prepared by reacting the compound (VIII) or a salt thereof with the compound (IX) or a salt thereof to Wittig Reaction.

This reaction is usually carried out in a solvent such as water, alcohol (e.g., methanol, ethanol, etc.), benzene, N,N-dimethylformamide, dimethylsulfoxide, nitromethane, tetrahydrofuran, toluene, methylene chloride, ethylene-dichloride, chloroform, dioxane, diethyl ether or any other solvents which do not adversely affect the reaction, or the mixture thereof.

The reaction temperature is not critical and the reaction is usually carried out under cooling to heating.

The reaction may be also carried out in the presence of an inorganic or an organic base such as an alkali metal (e.g., sodium, potassium, etc.), an alkali metal hydroxide (e.g., sodium hydroxide, potassium hydroxide, etc.), an alkali metal hydrogencarbonate (e.g., sodium hydrogencarbonate, potassium hydrogencarbonate, etc.), alkali metal carbonate (e.g., sodium carbonate, potassium carbonate, etc.), tri (lower)alkylamine (e.g., trimethylamine, triethylamine, diisopropylethylamine, etc.), alkali metal hydride (e.g., sodium hydride, etc.), alkali metal (lower)alkoxide (e.g. sodium methoxide, sodium ethoxide, potassium t-butoxide, etc.), pyridine, lutidine, picoline, dimethylaminopyridine, N-(lower)alkylmorpholine, N,N-di(lower) alkylbenzylamine, N,N-di(lower)alkylaniline, methyllitium, n-butyllitium, phenyllitium, 1,5-diazabicyclo[4.3.0]non-5-ene, or the like.

When the base, the acid and/or the starting compound are in liquid, they can be used also as a solvent.

Process 5

The compound (Ie) or a salt thereof can be prepared by reacting the compound (X) or its reactive derivative at the amino group or a salt thereof with the compound (XI) or a salt thereof.

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, dioxane, diethyl ether or any other solvents which do not adversely affect the reaction, or the mixture thereof.

The reaction temperature is not critical and the reaction is usually carried out under cooling to heating.

The reaction is usually carried out in the presence of an acid including Lewis acid.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, zinc halide (e.g., zinc chloride, zinc bromide, etc.), etc.] and the like.

The reaction may be also carried out in the presence of an inorganic or an organic base such as an alkali metal (e.g., sodium, potassium, etc.), an alkali metal hydroxide (e.g., sodium hydroxide, potassium hydroxide, etc.), an alkali metal hydrogencarbonate (e.g., sodium hydrogencarbonate, potassium hydrogencarbonate, etc.), alkali metal carbonate (e.g., sodium carbonate, potassium carbonate, etc.), tri (lower)alkylamine (e.g., trimethylamine, triethylamine, diisopropylethylamine, etc.), alkali metal hydride (e.g., sodium hydride, etc.), alkali metal (lower)alkoxide (e.g., sodium methoxide, sodium ethoxide, etc.), pyridine, lutidine, picoline, dimethylaminopyridine, N-(lower) alkylmorpholine, N,N-di(lower)alkylbenzylamine, N,N-di (lower)alkylaniline or the like.

When the base, the acid and/or the starting compound are in liquid, they can be used also as a solvent.

Process 6

The compound (If) or a salt thereof can be prepared by reacting the compound (VI) or its reactive derivative at the hydroxy group or a salt thereof with the compound (XII) or its reactive derivative at the carboxy group or a salt thereof.

Suitable reactive derivative at the hydroxy group of the compound (VI) may include halide, sulfonate, sulfate, diazo compound, and the like.

Suitable reactive derivative at the carboxy group of the compound (XII) may include an acid halide, an acid anhydride, an activated ester, and the like. The suitable example may be an acid chloride; acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorus acid, sulfurous acid, thiosulfuric acid, alkanesulfuric acid (e.g., methanesulfonic acid, ethanesulfonic acid, etc.), sulfuric acid, alkylcarbonic acid, aliphatic carboxylic acid (e.g., pivalic acid, pentanoic acid, isopentanoic acid, 2-ethylbutyric acid, trichloroacetic acid, etc.); aromatic carboxylic acid (e.g., benzoic acid, etc.); a symmetrical acid anhydride; an activated amide with imidazole, 4-substituted imidazole, dimethylpyrazole, triazole or tetrazole; an activated ester (e.g., cyanomethyl ester, methoxymethyl ester, dimethyliminomethyl [$(CH_3)_2{}^+N{=}CH{-}$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenylthio ester, p-nitrophenyl thioester, p-cresyl thioester, carboxymethyl thioester, pyranyl ester, pyridyl ester, piperidyl ester, 8-quinolyl thioester, etc.); an ester with a N-hydroxy compound (e.g., N,N-dimethylhydroxylamine, 1-hydroxy-2-(1H)-pyridone, N-hydroxysuccinimide, N-hydroxybenzotriazole, N-hydroxyphthalimide, 1-hydroxy-6-chloro-1H-benzotriazole, etc.); and the like. These reaction derivatives can optionally be selected from them according to the kind of the compound (XII) to be used.

This reaction is usually carried out in the presence of a base.

Suitable base may include, for example, an inorganic base such as alkali metal hydroxide (e.g., sodium hydroxide, potassium hydroxide, etc.), alkaline earth metal hydroxide (e.g., magnesium hydroxide, calcium hydroxide, etc.), alkali metal carbonate (e.g., sodium carbonate, potassium carbonate, cesium carbonate, etc.), alkaline earth metal carbonate (e.g., magnesium carbonate, calcium carbonate, etc.), alkali metal bicarbonate (e.g., sodium bicarbonate, potassium bicarbonate, etc.), alkali metal acetate (e.g., sodium acetate, potassium acetate, etc.), alkaline earth metal phosphate (e.g., magnesium phosphate, calcium phosphate, etc.), alkali metal hydrogen phosphate, (e.g., disodium hydrogen phosphate, dipotassium hydrogen phosphate, etc.) or the like, and an organic base such as trialkylamine (e.g., trimethylamine, triethylamine, etc.), pyridine, picoline, N-methylpyrrolidine, N-methylmorpholine, 1,5-diazabicyclo[4.3.0]non-5-ene, 1,4-diazabicyclo[2.2.2]-octane, 1,5-diazabicyclo[5.4.0]undecene-5 or the like.

This reaction is usually carried out in a solvent such as benzene, N,N-dimethylformamide, tetrahydrofuran, toluene, methylene chloride, ethylene dichloride, chloroform or any other solvents which do not adversely affect the reaction, or the mixture thereof.

The reaction temperature is not critical and the reaction is usually carried out under cooling to heating.

Process 7

The object compound (Ih) or a salt thereof can be prepared by reacting a compound (Ig) or its reactive derivative at the carboxy group or a salt thereof with a compound (XIII) or its reactive derivative at the amino group or a salt thereof.

Suitable reactive derivative at the carboxy group of the compound (Ig) may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g., methanesulfonic acid, etc.], aliphatic carboxylic acid [e.g., acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g., benzoic acid, etc.]; a symmetrical acid anhydride; an activated amide with imidazole, 4-substituted imidazole, dimethylpyrazole, triazole, tetrazole or 1-hydroxy-1H-benzotriazole; or an activated ester [e.g. cyanomethyl ester, methoxymethyl ester, dimethyliminomethyl [$(CH_3)_2{}^+N{=}CH{-}$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g., N,N-dimethylhydroxyamine, 1-hydroxy-2-(1H)-pyridone, N-hydroxysuccinimide, N-hydroxyphthalimide, 1-hydroxy-lH-benzotriazole, etc.], and the like. These reactive derivatives can optionally be selected from them according to the kind of the compound (Ig) to be used.

Suitable salts of the compound (Ig) and its reactive derivative can be referred to the ones as exemplified for the compound (I).

Suitable reactive derivative at the amino group of the compound (XIII) may include Schiff's base type imino or its tautomeric enamine type isomer formed by the reaction of the compound (XIII) with a carbonyl compound such as aldehyde, ketone or the like; a silyl derivative formed by the reaction of the compound (XIII) with a silyl compound such as bis(trimethylsilyl)acetamide, mono(trimethylsilyl)acetamide, bis(trimethylsilyl)urea or the like; a derivative formed by reaction of the compound (XIII) with phosphorus trichloride or phosgene, and the like.

Suitable salts of the compound (XIII) and its reactive derivative can be referred to the ones as exemplified for the compound (I).

The reaction is usually carried out in a conventional solvent such as water, alcohol [e.g., methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound (Ig) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonylbis-(2-methylimidazole); pentamethyleneketene-N-cyclohexylimine; diphenylketene-N-cyclohexylimine; ethoxyacetylene; 1-alkoxy-1-chloroethylene; trialkylphosphite; ethyl polyphosphate; isopropyl polyphosphate; phosphorous oxychloride (phosphoryl chloride); phosphorus trichloride; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-S-(m-sulfophenyl) isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, methanesulfonyl chloride, etc.; or the like.

The reaction may also be carried out in the presence of an inorganic or organic base such as an alkali metal carbonate, alkali metal bicarbonate, tri(lower)alkylamine, pyridine, N-(lower)alkylmorpholine, N,N-di(lower)alkylbenzylamine, or the like.

The reaction temperature is not critical, and the reaction is usually carried out under cooling to warming.

Process 8

The compound (Ij) or a salt thereof can be prepared by reacting the compound (Ii) or a salt thereof with Grignard Reagent.

Suitable Grignard reagent to be used in the present reaction may include the compound of the formula:

$$R^{12}\text{—MgX''} \qquad (XIV)$$

(wherein $R^{12}$ is lower alkyl, and X'' is halogen.)

This reaction is usually carried out in a solvent such as tetrahydrofuran, toluene, methylene chloride, ethylene dichloride, chloroform, dioxane, diethyl ether or any other solvent which do not adversely affect the reaction, or the mixture thereof.

The reaction temperature is not critical and the reaction is usually carried out under cooling to heating.

Process 9

The object compound (Il) or a salt thereof can be prepared by subjecting a compound (Ik) or a salt thereof to de-acylation reaction of acylamino group.

This reaction is carried out in accordance with a conventional method such as hydrolysis, reduction or the like.

The hydrolysis is preferably carried out in the presence of a base or an acid including Lewis acid. Suitable base may include an inorganic base and an organic base such as an alkali metal [e.g., sodium, potassium, etc.], an alkaline earth metal [e.g., magnesium, calcium, etc.],the hydroxide or carbonate or bicarbonate thereof, trialkylamine [e.g., trimethylamine, triethylamine, etc.], picoline, 1,5-diazabicyclo[4.3.0]non-5-ene, 1,4-diazabicyclo[2.2.2]-octane, 1,8-diazabicyclo[5.4.0]undec-7-ene, or the like.

Suitable acid may include an organic acid [e.g., formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, etc.].

The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

The reduction method applicable for the elimination reaction may include chemical reduction and catalytic reduction.

Suitable reducing agents to be used in chemical reduction are a combination of metal [e.g., tin, zing, iron, etc.] or metallic compound [e.g., chromium chloride, chromium acetate, etc.] and an organic or inorganic acid [e.g., formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g., spongy palladium, palladium black, palladium oxide, palladium on carbon, colloidal palladium, palladium on barium, sulfate, palladium on barium carbonate, etc.], nickel catalysts [e.g., reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.] and the like.

The reduction is usually carried out in a conventional solvent which does not adversely influence the reaction such as water, methanol, ethanol, propanol, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to warming.

Process 10

The compound (Ik) or a salt thereof can be prepared by subjecting the compound (Il) or its reactive derivative at the amino group, or a salt thereof to acylation reaction.

Suitable acylating agent to be used in the present acylation reaction may include the compound of the formula:

$$R^{13}\text{—OH} \qquad (XV)$$

(wherein $R^{13}$ is acyl) or its reactive derivative, or a salt thereof.

Suitable reactive derivative at the amino group of the compound (Il) may include Schiff's base type imino or its tautomeric enamine type isomer formed by the reaction of the compound (Il) with a carbonyl compound such as aldehyde, ketone or the like; a silyl derivative formed by the reaction of the compound (Il) with a silyl compound such as N,O-bis(trimethylsilyl)acetamide, N-trimethylsilylacetamide or the like; a derivative formed by the reaction of the compound (Il) with phosphorus trichloride or phosgene, and the like.

Suitable reactive derivative of the compound (XV) may include an acid halide, an acid anhydride, an activated ester, and the like. The suitable example may be an acid chloride; acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, alkanesulfonic acid (e.g., methanesulfonic acid, ethanesulfonic acid, etc.), sulfuric acid, alkylcarbonic acid, aliphatic carboxylic acid (e.g., pivalic acid, pentanoic acid, isopentanoic acid, 2-ethylbutyric acid, trichloroacetic acid, etc.); aromatic carboxylic acid (e.g., benzoic acid, etc.); a symmetrical acid anhydride; an activated amide with imidazole, 4-substituted imidazole, dimethylpyrazole, triazole or tetrazole; an activated ester (e.g., cyanomethyl, ester methoxymethyl ester, dimethyliminomethyl [$(CH_3)_2^+N\text{=}CH$—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenylthioester, p-nitrophenyl thioester, p-cresyl thioester, carboxymethyl thioester, pyranyl ester, pyridyl ester, piperidyl ester, 8-quinolyl thioester, etc.); an ester with a N-hydroxy compound (e.g., N,N-dimethylhydroxylamine, 1-hydroxy-2-(1H)-pyridone, N-hydroxysuccinimide, N-hydroxybenzotriazole, N-hydroxyphthalimide, 1-hydroxy-6-chloro-1H-benzotriazole, etc.); and the like. These reactive derivatives can optionally be selected from them according to the kind of the compound (XV) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvent which do not adversely affect the reaction, or the mixture thereof.

When the compound (XV) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide); N-cyclohexyl-N'-(4-diethylaminocyclohexyl)carbodiimide; N,N'-diisopropylcarbodiimide; N-ethyl-N'-(3-dimethylaminopropyl)carbodiimide; N,N-carbonyl-bis(2-methylimidazole); pentamethyleneketene-N-cyclohexylimine; diphenylketene-N-cyclohexylimine; ethoxyacetylene; 1-alkoxy-1-chloroethylene; trialkyl phosphite; isopropyl polyphosphate; phosphorous oxychloride (phosphoryl chloride); phosphorous trichloride; thionyl chloride; oxalyl chloride; triphenylphosphite; 2-ethyl-7-hydroxybenzisoxazolium salt; 2-ethyl-5-(m-sulfophenyl) isoxazolium hydroxide intra-molecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorous oxychloride, etc.; or the like.

The reaction may also be carried out in the presence of an organic or inorganic base such as an alkali metal bicarbonate, tri(lower)alkylamine, pyridine, N-(lower)alkylmorphorine, N,N-di(lower)alkylbenzylamine, or the like.

The reaction temperature is not critical, and the reaction is usually carried out under cooling to heating.

Process 11

The compound (Im) or a salt thereof can be prepared by subjecting the compound (Ij) or a salt thereof to acylation reaction. This reaction can be carried out in a similar manner to that of the afore-mentioned Process 10, and therefore the reagents to be used and the reaction conditions (e.g., solvent, reaction temperature, etc.) can be referred to those of the Process 10.

In the starting compound (II), the compound (IIa) can be prepared according to the following reaction scheme.

Process A

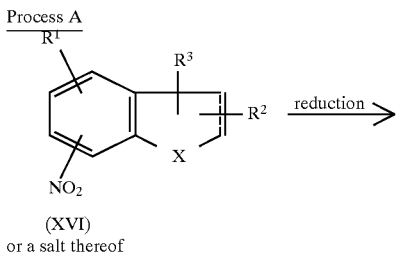

(XVI)
or a salt thereof

-continued

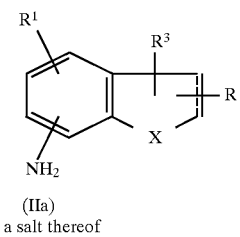

(IIa)
or a salt thereof wherein $R^1$, $R^2$, $R^3$, ---and X are each as defined above.

The reaction of this process can be carried out according to the method of Preparation 42 (1) mentioned below is or the similar manners thereto.

Among the starting compounds (II) to (XVI), some of them are novel compounds. They can be prepared by the similar manners to those disclosed in Preparations mentioned later in the present specification, or any process known in this field of the art for preparing structurally analogous compounds thereto.

The compounds obtained by the above Processes 1 to 11 can be isolated and purified by a conventional method such as pulverization, recrystallization, columnchlomatography, reprecipitation or the like.

It is to be noted that each of the object compound (I) may include one or more stereoisomer such as optical isomer(s) and geometrical isomer(s) due to asymmetric carbon atom(s) and double bond(s) and all such isomers and mixture thereof are included within the scope of this invention.

The pharmaceutical composition of the present invention can be used in the form of a pharmaceutical preparation, for example, in solid, semisolid or liquid form, which contains the object compound (I) or a pharmaceutically acceptable salt thereof, as an active ingredient in admixture with an organic or inorganic carrier or excipient which is suitable for rectal; pulmonary (nasal or buccal inhalation); ocular; external (topical); oral administration; parenteral (including subcutaneous, intravenous and intramuscular) administrations; insufflation (including aerosols from metered dose inhalator); nebulizer; or dry powder inhalator.

The active ingredient may be compounded, for example, with the usual non-toxic, pharmaceutically acceptable carriers in a solid form such as granules, tablets, dragees, pellets, troches, capsules, or suppositories; creams; ointments; aerosols; powders for insufflation; in a liquid form such as solutions, emulsions, or suspensions for injection; ingestion; eye drops; and any other form suitable for use. And, if necessary, there may be included in the above preparation auxiliary substance such as stabilizing, thickening, wetting, emulsifying and coloring agents; perfumes or buffer; or any other commonly may be used as additives.

The object compound (I) or a pharmaceutically acceptable salt thereof include solvated compound [e.g., enclosure compound (e.g., hydrate, etc.)].

The object compound (I) or a pharmaceutically acceptable salt thereof include both its crystal form and non-crystal form.

The object compound (I) or a pharmaceutically acceptable salt thereof is/are included in the pharmaceutical composition in an amount sufficient to produce the desired effect upon the process or condition of diseases.

The pharmaceutical composition of the present invention can be manufactured by the conventional method in this field of the art. If necessary, the technique generally used in this field of the art for improving the bioavailability of a drug can be applied to the pharmaceutical composition of the present invention.

While the dosage of therapeutically effective amount of the object compound (I) varies from and also depends upon the age and condition of each individual patient to be treated, in the case of intravenous administration, a daily dose of 0.001–100 mg of the object compound (I) per kg weight of a human being or an animal, in the case of intramuscular administration, a daily dose of 0.001–100 mg of the object compound (I) per kg weight of a human being of an animal, in case of oral administration, a daily dose of 0.001–200 mg of the object compound (I) per kg weight of a human being or an animal is generally given for the prevention and/or the treatment of aforesaid diseases 1 to 4 times a day in a human being or an animal.

In order to illustrate the usefulness of the object compound (I), the pharmacological test data of the representative compound of the compounds (I) is shown in the following.

Test Compound (1) 7-(2,6-Dichlorobenzoylamino)-2,3-dimethylbenzo[b]furan

Test (Bone organ culture)
Test Method

Calvariae from Wistar rats were excised and cultured in wells of 12-well culture plates containing 2 ml of Dulbecco's modified minimum essential medium supplemented with 10% fetal bovine serum and $10^{-8}$M human parathyroid hormone fragment (1–34) [PTH] in the presence of the test compound. In control dishes, PTH was not added. Control and PTH control were exposed to an equivalent concentration of the vehicle. Six days later, the concentration of calcium in the medium was measured by methylxylenol blue method and the percentage of inhibition of PTH-induced bone resorption was calculated according to following formula.

$$\text{Inhibition (\%)} \frac{[Ca] \text{ in } PTH \text{ control dishes} - [Ca] \text{ in the test compound dishes}}{[Ca] \text{ in } PTH \text{ control dishes} - [Ca] \text{ in control dishes}} \times 100$$

Test Result

| Compound dose = $1 \times 10^{-5}$ (M) | |
| --- | --- |
| Test Compound | Inhibition (%) |
| (1) | 100 |

The following Preparations and Examples are given for the purpose of illustrating the present invention in more detail.

Preparation 1 (1)

To a solution of pentan-3-one oxime (6.00 g) in dimethylformamide (30 ml) was added sodium hydride (60% oil suspension, 2.37 g) under ice cooling. After 15 minutes, to the above mixture was added dropwise 1-fluoro-2-nitrobenzene (5.98 g) in dimethylformamide (30 ml). The mixture was stirred for 3 hours at ambient temperature and poured into a mixture of ice and water. The separated oil was extracted with diethyl ether. The organic layer was washed with water, dried over sodium sulfate and evaporated in vacuo to give pentan-3-one O-(2-nitrophenyl)oxime (10.51 g) as a brown oil.

NMR (CDCl$_3$, δ): 1.12–1.30 (6H, m), 2.40 (2H, q, J=7 Hz), 2.58 (2H, q, J=7 Hz), 7.03 (1H, dt, J=1 and 8 Hz), 7.53 (1H, dt, J=1 and 8 Hz), 7.75 (1H, dd, J=1 and 8 Hz), 7.95 (1H, dd, J=1 and 8 Hz)

The following compounds [Preparations 1 (2) to (8)] were obtained according to a similar manner to that of Preparation 1 (1).

Preparation 1 (2)
Butan-2-one O-(4-carboxy-2-nitrophenyl)oxime
mp: 172°–178° C.

Preparation 1 (3)
Acetone O-(4-fluoro-2-nitrophenyl)oxime
mp: 76°–77° C. NMR (CDCl$_3$, δ): 2.05 (3H, s), 2.15 (3H, s), 7.27 (1H, m), 7.63–7.75 (2H, m)

Preparation 1 (4)
2,3,5,6-Tetrahydro-4H-thiopyran-4-one O-(2-nitrophenyl)oxime
mp: 71°–73° C. NMR (CDCl$_3$, δ): 2.68–2.75 (2H, m), 2.78–2.93 (4H, m), 3.07–3.17 (2H, m), 7.08 (1H, dt, J=1 and 8 Hz), 7.54 (1H, dt, J=1 and 8 Hz), 7.72 (1H, dd, J=1 and 8 Hz), 7.95 (1H, dd, J=1 and 8 Hz)

Preparation 1 (5)
Acetone O-(4-chloro-2-nitrophenyl)oxime
mp: 62°–65° C. NMR (CDCl$_3$, δ): 2.05 (3H, s), 2.15 (3H, s), 7.49 (1H, d, J=7 Hz), 7.71 (1H, d, J=7 Hz), 7.94 (1H, s)

Preparation 1 (6)
Ethyl 5-(2-nitrophenyl)oxyiminohexanoate oil

Preparation 1 (7)
Cycloheptanone O-(2-nitrophenyl)oxime
NMR (CDCl$_3$, δ): 1.55–1.68 (4H, m), 1.68–1.79 (4H, m), 2.52 (2H, t, J=6 Hz), 2.82 (2H, t, J=6 Hz), 7.02 (1H, t, J=8 Hz), 7.52 (1H, t, J=8 Hz), 7.73 (1H, d, J=8 Hz), 7.91 (1H, d, J=8 Hz)

Preparation 1 (8)
4-Ethoxycarbonylbutan-2-one O-(2-nitrophenyl)oxime
ESI Mass: 281 (M+H)$^+$, 303 (M+Na)$^+$ Preparation 2 (1)

A mixture of 2-bromophenol (5 g), potassium carbonate (5.99 g) and 2-chlorocyclohexanone (4.22 g) in N,N-dimethylformamide was stirred at 60° C. for 4 hours. The reaction mixture was poured into cold water and the separated oil was extracted with diethyl ether. The extract was washed with water, dried over sodium sulfate and concentrated in vacuo. The residue was crystallized from n-hexane to give 2-(2-bromophenoxy)cyclohexanone (4.36 g).

mp: 72°–73° C. NMR (CDCl$_3$, δ): 1.74 (1H, m), 1.85–2.05 (2H, m), 2.10–2.40 (4H, m), 2.70 (1H, m), 4.64 (1H, dd, J=5 and 7.5 Hz), 6.81 (1H, d, J=7.5 Hz), 6.85 (1H, t, J=7.5 Hz), 7.20 (1H, t, J=7.5 Hz), 7.54 (1H, d, J=7.5 Hz)

The following compounds [Preparations 2 (2) and (3)] were obtained according to a similar manner to that of Preparation 2 (1).

Preparation 2 (2)
3-(2-Acetylamino-4-nitrophenoxy)-2-butanone NMR (CDCl$_3$, δ): 1.70 (3H, d, J=6 Hz), 2.22 (3H, s), 2.30 (3H, s), 4.87 (1H, q, J=6 Hz), 6.78 (1H, d, J=8 Hz), 7.91 (1H, dd, J=2 and 8 Hz), 8.19 (1H, br s), 9.30 (1H, d, J=2 Hz)

Preparation 2 (3)
2',6'-Dichloro-5-methyl-2-(1-methyl-2-oxopropyl)-oxybenzophenone
mp: 111°–113° C. NMR (CDCl$_3$, δ): 0.97 (3H, d, J=7 Hz), 1.95 (3H, s), 2.35 (3H, s), 4.42 (1H, q, J=7 Hz), 6.53 (1H, d, J=8 Hz), 7.20–7.35 (4H, m), 7.93 (1H, s)

Preparation 3

2,6-Dichlorobenzoyl chloride (2.14 g) was added to a solution of p-cresol (1.08 g) and triethylamine (1.11 g) in dichloromethane (30 ml) dropwise at 4° C. The mixture was stirred at ambient temperature overnight. The reaction mixture was washed with aqueous saturated sodium bicarbonate and brine, dried over sodium sulfate and evaporated in vacuo to give 4-methylphenyl 2,6-dichlorobenzoate (2.73 g) as an oil. NMR (CDCl$_3$, δ): 2.38 (3H, s), 7.17 (2H, d, J=8 Hz), 7.25 (2H, d, J=7 Hz), 7.30–7.45 (3H, m)

Preparation 4

A mixture of 4-methylphenyl 2,6-dichlorobenzoate (2.53 g) and aluminum chloride (2.4 g) in 1,2-dichloroethane (30 ml) was refluxed for 3 hours. The reaction mixture was cooled and poured into a mixture of ice and 1N hydrochloric acid. The separated oil was extracted with dichloromethane. The extract was washed with brine, aqueous saturated sodium bicarbonate and brine, dried over sodium sulfate and evaporated in vacuo. The residue was purified by column chromatography on silica gel and the obtained oil was crystallized from diethyl ether to give 2',6'-dichloro-2-hydroxy-5-methylbenzophenone (1.72 g).

mp: 139°–141° C. NMR (CDCl$_3$, δ): 2.22 (3H, s), 6.90 (1H, s), 7.00 (1H, d, J=8 Hz), 7.30–7.45 (4H, m)

Preparation 5 (1)

To a suspension of butan-2-one O-(4-carboxy-2-nitrophenyl)oxime (4.5 g) in ethanol (45 ml) was added conc. sulfuric acid (6.8 ml) dropwise. The mixture was refluxed for 20 hours. The reaction mixture was cooled and poured into a mixture of ice and water. The separated oil was extracted with ethyl acetate. The extract was washed with brine, aqueous saturated sodium bicarbonate and brine, dried over sodium sulfate and evaporated in vacuo. The residue was purified by column chromatography on silica gel. The first fractions were evaporated in vacuo and the residue was crystallized from hexane to give 5-ethoxycarbonyl-2-ethyl-7-nitrobenzo[b]furan (0.82 g).

mp: 82°–83° C. NMR (CDCl$_3$, δ): 1.42 (3H, t, J=8 Hz), 1.46 (3H, t, J=8 Hz), 2.95 (2H, q, J=8 Hz), 4.46 (2H, q, J=8 Hz), 6.61 (1H, s), 8.50 (1H, s), 8.75 (1H, s)

The second fractions were evaporated in vacuo and the residue was crystallized from hexane to give 2,3-dimethyl-5-ethoxycarbonyl-7-nitrobenzo[b]furan (1.2 g).

mp: 123°–124° C. NMR (CDCl$_3$, δ): 1.45 (3H, t, J=8 Hz), 2.23 (3H, s), 2.52 (3H, s), 4.47 (2H, q, J=8 Hz), 8.40 (1H, s), 8.73 (1H, s)

The following compounds [Preparations 5 (2) to (7)] were obtained according to a similar manner to that of Preparation 5 (1).

Preparation 5 (2)

5-Fluoro-2-methyl-7-nitrobenzo[b]furan mp: 103°–104° C. NMR (CDCl$_3$, δ): 2.58 (3H, s), 6.52 (1H, s), 7.48 (1H, d, J=8 Hz), 7.78 (1H, d, J=8 Hz)

Preparation 5 (3)

7-Acetylamino-2,3-dimethyl-5-nitrobenzo[b]furan mp: 197°–198.5° C. NMR (CDCl$_3$, δ): 2.20 (3H, s), 2.31 (3H, s), 2.45 (3H, s), 7.63 (1H, br s), 8.09 (1H, d, J=2 Hz), 9.02 (1H, m)

Preparation 5 (4)

6-Nitro-3,4-dihydro-1H-thiopyrano[4,3-b]benzofuran mp: 114°–116° C. NMR (CDCl$_3$, δ): 3.03–3.12 (2H, m), 3.12–3.23 (2H, m), 3.77–3.80 (2H, m), 7.35 (1H, t, J=8 Hz), 7.72 (1H, dd, J=1 and 8 Hz), 8.10 (1H, dd, J=1 and 8 Hz)

Preparation 5 (5)

5-Chloro-2-methyl-7-nitrobenzo[b]furan mp: 153°–154° C. NMR (CDCl$_3$, δ): 2.58 (3H, s), 6.49 (1H, s), 7.73 (1H, s), 8.03 (1H, s)

Preparation 5 (6)

2-(3-Ethoxycarbonylpropyl)-7-nitrobenzo[b]furan NMR (CDCl$_3$, δ): 1.27 (3H, t, J=7 Hz), 2.13 (2H, quint., J=7 Hz), 2.44 (2H, t, J=7 Hz), 2.45 (2H, t, J=7 Hz), 4.14 (2H, q, J=7 Hz), 6.57 (1H, s), 7.30 (1H, t, J=8 Hz), 7.79 (1H, d, J=8 Hz), 8.07 (1H, d, J=8 Hz)

Preparation 5 (7)

1-Nitro-6,7,8,9-tetrahydro-5H-10-oxo-benzo[b]azulene mp: 74°–75° C. NMR (CDCl$_3$, δ): 1.77–1.92 (6H, m), 2.68–2.74 (2H, m), 3.00–3.08 (2H, m), 7.29 (1H, t, J=8 Hz), 7.69 (1H, d, J=8 Hz), 8.01 (1H, d, J=8 Hz)

Preparation 6

A mixture of 2,4-bis(benzoylamino)phenol (6.0 g), 3-chlorobutan-2-one (2.3 g) and potassium carbonate (5.0 g) in N,N-dimethylformamide (30 ml) was stirred at 70° C. for 3 hours. The reaction mixture was cooled and poured into water. The separated oil was extracted with ethyl acetate. The extract was washed with brine, dried over sodium sulfate and evaporated in vacuo. To the residue was added conc. sulfuric acid (30 ml) and the mixture was stirred at 40° C. for 7 hours. The reaction mixture was cooled and poured into a mixture of ice and water. The separated oil was extracted with ethyl acetate and the extract was washed with brine, dried over sodium sulfate and evaporated in vacuo. The residue was purified by column chromatography on silica gel and the obtained oil was crystallized from diethyl ether to give 5,7-bis(benzoylamino)-2,3-dimethylbenzo[b]furan (3.7 g).

mp: 185°–186° C. NMR (CDCl$_3$, δ): 2.16 (3H, s), 2.40 (3H, s), 7.40–7.65 (6H, m), 7.85–8.00 (4H, m), 8.09 (2H, s), 8.15 (1H, s), 8.32 (1H, s)

Preparation 7

A mixture of pentan-3-one O-(2-nitrophenyl)oxime (10.50 g) in 10% hydrogen chloride-methanol (105 ml) was refluxed for 4 hours. After concentration in vacuo, the residue was extracted with ethyl acetate and water. The obtained organic layer was washed with saturated aqueous sodium bicarbonate, brine and dried over, sodium sulfate. After evaporation in vacuo, the residue was purified by column chromatography on silica gel (eluate; ethyl acetate:n-hexane=1:6) to give a solid. The resulting solid was triturated with a mixture of ethanol and water (2:1) and the precipitate was collected to give 2-ethyl-3-methyl-7-nitrobenzo[b]furan (4.44 g).

mp: 58°–60° C. NMR (CDCl$_3$, δ): 1.36 (3H, t, J=7 Hz), 2.21 (3H, s), 2.87 (2H, q, J=7 Hz) 7.29 (1H, t, J=8 Hz), 7.70 (1H, d, J=8 Hz), 8.03 (1H, d, J=8 Hz)

Preparation 8

A solution of 4-ethoxycarbonylbutan-2-one O-(2-nitrophenyl)oxime (7.83 g) in 37% ethanolic hydrogen chloride (120 ml) was stirred at 80° C. for 6 hours. The insoluble matter was filtered off and the filtrate was evaporated in vacuo. The residue was purified by column chromatography on silica gel and the obtained oil was crystallized from a mixture of ethanol (20 ml) and water (4 ml) to give a mixture of 3-ethoxycarbonylmethyl-2-methyl-7-nitrobenzo[b]furan and 2-(2-ethoxycarbonylethyl)-7-nitrobenzo[b]furan (3.41 g).

To a solution of these mixture (2.0 g) in dichloromethane was added bromine (0.28 ml) in dichloromethane (1 ml) dropwise at 4° C. The mixture was stirred at 4° C. for 30 minutes and at ambient temperature for 1 hour. The reaction mixture was washed with 5% aqueous sodium thiosulfate and aqueous saturated sodium bicarbonate, dried over sodium sulfate and evaporated in vacuo. The residue was purified by column chromatography on silica gel. The less polar fraction was combined and evaporated in vacuo to give 3-bromo-2-(2-ethoxycarbonylethyl)-7-nitrobenzo[b]furan (582 mg).

mp: 71°–74° C. NMR (CDCl$_3$, δ): 1.28 (3H, t, J=7 Hz), 2.84 (2H, t, J=7 Hz), 3.27 (2H, t, J=7 Hz), 4.19 (2H, q, J=7 Hz), 7.41 (1H, t, J=8 Hz), 7.79 (1H, d, J=8 Hz), 8.17 (1H, d, J=8 Hz)

The more polar fraction was combined and evaporated in vacuo. The residue was crystallized from a mixture of ethanol and water to give 3-ethoxycarbonylmethyl-2-methyl-7-nitrobenzo[b]furan (832 mg).

mp: 64°–68° C. NMR (CDCl$_3$, δ): 1.25 (3H, t, J=7 Hz), 2.56 (3H, s), 3.63 (2H, s), 4.17 (2H, q, J=7 Hz), 7.32 (1H, t, J=8 Hz), 7.80 (1H, d, J=8 Hz), 8.07 (1H, d, J=8 Hz)

Preparation 9

A mixture of 2-methyl-7-nitrobenzo[b]furan (2.66 g), N-bromosuccinimide (3.21 g) and 2,2'-azobis-(2,4-dimethyl-4-methoxyvaleronitrile) (270 mg) in dichloromethane (30 ml) was refluxed for 1 hour. The reaction mixture was washed with aqueous saturated sodium bicarbonate and brine, dried over sodium sulfate and concentrated in vacuo. The residue was crystallized from diethyl ether to give 2-bromomethyl-7-nitrobenzo[b]furan (3.3 g).

mp: 146°–147° C. NMR (CDCl$_3$, δ): 4.66 (2H, s), 6.92 (1H, s), 7.38 (1H, t, J=8 Hz), 7.87 (1H, d, J=8 Hz), 8.18 (1H, d, J=8 Hz)

Preparation 10

A mixture of 2-bromomethyl-7-nitrobenzo[b]furan (512 mg), ethyl mercaptoacetate (0.24 ml) and potassium carbonate (552 mg) in N,N-dimethylformamide (4 ml) was stirred at ambient temperature for 2 hours. To the reaction mixture was added cold water and the separated solid was collected, washed with water and dried to give 2-ethoxycarbonylmethylthiomethyl-7-nitrobenzo[b]furan (546 mg).

mp: 84°–87° C. NMR (CDCl$_3$, δ): 1.30 (3H, t, J=8 Hz), 3.31 (2H, s), 4.08 (2H, s), 4.20 (2H, q, J=8 Hz), 6.79 (1H, s), 7.34 (1H, t, J=8 Hz), 7.82 (1H, d, J=8 Hz), 8.11 (1H, d, J=8 Hz)

Preparation 11 (1)

A solution of 2-(3-ethoxycarbonylpropyl)-7-nitrobenzo[b]furan (1.0 g) in a mixture of aqueous 1N-sodium hydroxide (7.2 ml) and ethanol (5 ml) was stirred at 50° C. for 1 hour. The reaction mixture was diluted with water and acidified with 4N-hydrochloric acid. The separated solid was collected, washed with water and dried to give 2-(3-carboxypropyl)-7-nitrobenzo[b]furan (752 mg).

mp: 180°–182° C. NMR (CDCl$_3$, δ): 2.11–2.21 (2H, m), 2.52 (2H, t, J=7 Hz), 2.98 (2H, t, J=7 Hz), 6.59 (1H, s), 7.30 (1H, t, J=8 Hz), 7.80 (1H, d, J=8 Hz), 8.07 (1H, d, J=8 Hz)

The following compound was obtained according to a similar manner to that of Preparation 11 (1).
Preparation 11 (2)

2-Carboxymethylthiomethyl-7-nitrobenzo[b]furan mp: 92°–93° C. NMR (DMSO-d$_6$, δ): 3.37 (2H, s), 4.11 (2H, s), 7.02 (1H, s), 7.47 (1H, t, J=8 Hz), 8.06 (1H, d, J=8 Hz), 8.11 (1H, d, J=8 Hz)

Preparation 12 (1)

A solution of 2-(3-carboxypropyl)-7-nitrobenzo[b]furan (500 mg) in thionyl chloride (5 ml) was refluxed for 1.5 hours. The reaction mixture was diluted with toluene and concentrated in vacuo. The residue was dissolved in dichloromethane (15 ml) and to the mixture was added aluminum chloride (435 mg) at 4° C. The mixture was stirred at ambient temperature for 2 hours and partitioned between 1N-hydrochloric acid and dichloromethane. The organic layer was separated, washed with brine, dried over sodium sulfate and concentrated in vacuo. The residue was purified by column chromatography on silica gel and the obtained oil was crystallized from a mixture of ethyl acetate and n-hexane to give 6-nitro-1-oxo-1,2,3,4-tetrahydrodibenzofuran (282 mg).

mp: 122°–123.5° C. NMR (CDCl$_3$, δ): 2.30–2.41 (2H, m), 2.68 (2H, t, J=7 Hz), 3.20 (2H, t, J=7 Hz), 7.49 (1H, t, J=8 Hz), 8.18 (1H, d, J=8 Hz), 8.40 (1H, d, J=8 Hz)

The following compound was obtained according to a similar manner to that of Preparation 12 (1).
Preparation 12 (2)

1,2-Dihydro-6-nitro-1-oxo-4H-thiopyrano[3,4-b]benzo[b]furan mp: 210°–211° C. NMR (CDCl$_3$, δ): 3.56 (2H, s), 4.13 (2H, s), 7.52 (1H, t, J=8 Hz), 8.20 (1H, d, J=8 Hz), 8.45 (1H, d, J=8 Hz)

Preparation 13

A mixture 1-hydroxyimino-6-nitro-1,2,3,4-tetrahydrodibenzofuran (425 mg) p-toluenesulfonyl chloride (394 mg) and triethylamine (521 mg) in dichloromethane was stirred at ambient temperature for 2 hours. The mixture was directly purified by column chromatography on silica gel and the obtained oil was crystallized from diisopropyl ether to give 6-nitro-1,2,3,4-tetrahydro-1-p-toluenesulfonyloxyiminodibenzofuran (609 mg).

mp: 175°–182° C. (dec.) NMR (CDCl$_3$, δ): 2.09–2.19 (2H, m), 2.46 (3H, s), 2.65 (4/5H, m), 2.90 (6/5H, t, J=6 Hz), 2.98–3.11 (2H, m), 7.32–7.42 (3H, m), 7.89–8.00 (2H, m), 8.07–8.19 (8/5H, m), 8.61 (2/5H, d, J=8 Hz)

Preparation 14

A mixture of 2-(2-boromophenoxy)cyclohexanone (4.306 g) and polyphosphoric acid (40 g) was stirred at 50° C. for 4 hours. The reaction mixture was poured into cold water and the separated oil was extracted with ethyl acetate. The extract was washed with water, aqueous saturated sodium bicarbonate and brine, dried over sodium sulfate and concentrated in vacuo. The residue was purified by column chromatography on silica gel. The appropriate fractions were combined and concentrated in vacuo to give 6-bromo-1,2,3,4-tetrahydrodibenzofuran (3.49 g) as an oil.

NMR (CDCl$_3$, δ): 1.85 (2H, m), 1.95 (2H, m), 2.61 (2H, m), 2.80 (2H, m), 7.06 (1H, t, J=7.5 Hz), 7.33 (1H, d, J=7.5 Hz), 7.35 (1H, d, J=7.5 Hz)

Preparation 15

To a suspension of magnesium (345 mg) in tetrahydrofuran (5 ml) was added 6-bromo-1,2,3,4-tetrahydrodibenzofuran (3.39 g) in tetrahydrofuran (15 ml) dropwise. The mixture was refluxed for 1 hour and cooled to 4° C. Dry ice (2.7 g) was added to the mixture and the mixture was stirred at ambient temperature for 30 minutes. To the mixture was added 3.6% hydrochloric acid and chloroform. The organic layer was separated, dried over sodium sulfate and concentrated in vacuo. The residue was crystallized from n-hexane to give 1,2,3,4-tetrahydrodibenzofuran-6-carboxylic acid (2.60 g).

mp: 197°–198° C. NMR (CDCl$_3$, δ): 1.88 (2H, m), 1.97 (2H, m), 2.64 (2H, m), 2.85 (2H, m), 7.28 (1H, t, J=7.5 Hz), 7.65 (1H, d, J=7.5 Hz), 7.95 (1H, d, J=7.5 Hz)

Preparation 16

A mixture of 7-carboxy-2,3-dimethylbenzo[b]furan (2 g) and N,N-dimethylformamide (1 drop) in thionyl chloride (10 ml) was refluxed for 2 hours. The reaction mixture was cooled and concentrated in vacuo. The crystalline residue was triturated with n-hexane to give 7-chlorocarbonyl-2,3-dimethylbenzo[b]furan (2.17 g).

mp: 75°–77° C. NMR (CDCl$_3$ δ): 2.19 (3H, s), 2.47 (3H, s), 7.32 (1H, t, J=7.5 Hz), 7.72 (1H, d, J=7.5 Hz), 8.03 (1H, d, J=7.5 Hz)

Preparation 17

Sodium borohydride (38 mg) was added to a solution of 6-nitro-1-oxo-1,2,3,4-tetrahydrodibenzofuran (231 mg) in a mixture of ethanol (1.5 ml) and N,N-dimethylformamide (1.5 ml). The mixture was stirred at ambient temperature for 20 minutes, diluted with water and acidified with 3.6% hydrochloric acid. The separated oil was extracted with ethyl acetate and the extract was washed with aqueous saturated sodium bicarbonate and brine, dried over sodium sulfate and concentrated in vacuo. The residue was crystallized from diisopropyl ether to give 1-hydroxy-6-nitro-1,2,3,4-tetrahydrodibenzofuran (175 mg).

mp: 127°–129° C. NMR (CDCl$_3$, δ): 1.90–2.05 (2H, m), 2.05–2.20 (2H, m), 2.88 (2H, m), 5.08 (1H, m), 7.35 (1H, t, J=7.5 Hz), 7.97 (1H, d, J=7.5 Hz), 8.08 (1H, d, J=7.5 Hz)

Preparation 18 (1)

To a mixture of 2-methyl-7-nitrobenzo[b]furan (177 mg) and aluminum chloride (200 mg) in dichloromethane (5 ml) was added dropwise propionyl chloride (0.18 ml). The mixture was stirred at ambient temperature for 3 hours and poured into a mixture of ice and 1N-hydrochloric acid. The separated oil was extracted with dichloromethane and the extract was washed with brine, dried over sodium sulfate and evaporated in vacuo. The residue was crystallized from diethyl ether to give 2-methyl-7-nitro-3-propionylbenzo[b]furan (215 mg).

mp: 128°–129° C. NMR (CDCl$_3$, δ): 1.29 (3H, t, J=7 Hz), 2.92 (3H, s), 2.99 (2H, q, J=7 Hz), 7.35 (1H, t, J=7 Hz), 8.13 (1H, d, J=7 Hz), 8.42 (1H, d, J=7 Hz)

The following compounds [Preparations 18 (2) to (8)] were obtained according to a similar manner to that of Preparation 18 (1).

Preparation 18 (2)

3-Acetyl-5-fluoro-2-methyl-7-nitrobenzo[b]furan mp: 144°–146° C. NMR (CDCl$_3$, δ): 2.64 (3H, s), 2.93 (3H, s), 7.88 (1H, d, J=8 Hz), 8.20 (1H, d, J=8 Hz)

Preparation 18 (3)

3-Acetyl-5-chloro-2-methyl-7-nitrobenzo[b]furan mp: 171°–172° C. NMR (CDCl$_3$, δ): 2.65 (3H, s), 2.92 (3H, s), 8.12 (1H, s), 8.46 (1H, s)

Preparation 18 (4)

3-Ethoxalyl-2-methyl-7-nitrobenzo[b]furan mp: 88°–89° C. NMR (CDCl$_3$, δ): 1.45 (3H, t, J=8 Hz), 2.82 (3H, s), 4.49 (2H, q, J=8 Hz), 7.48 (1H, t, J=8 Hz), 8.19 (1H, d, J=8 Hz), 8.39 (1H, d, J=8 Hz)

Preparation 18 (5)

3-Benzoyl-2-methyl-7-nitrobenzo[b]furan mp: 92°–93° C. NMR (CDCl$_3$, δ): 2.60 (3H, s), 7.38 (1H, t, J=8 Hz), 7.53 (2H, t, J=8 Hz), 7.65 (1H, t, J=8 Hz), 7.80 (2H, d, J=8 Hz), 7.89 (1H, d, J=8 Hz), 8.13 (1H, d, J=8 Hz)

Preparation 18 (6)

3-Butyryl-2-methyl-7-nitrobenzo[b]furan mp: 121.5°–123° C. NMR (CDCl$_3$, δ): 1.03 (3H, t, J=7 Hz), 1.80 (2H, sex, J=7 Hz), 2.84–2.91 (5H, m), 7.42 (1H, t, J=8 Hz), 8.11 (1H, d, J=8 Hz), 8.39 (1H, d, J=8 Hz)

Preparation 18 (7)

3-Cyclohexylcarbonyl-2-methyl-7-nitrobenzo[b]furan mp: 164°–166° C. NMR (CDCl$_3$, δ): 1.25–2.00 (10H, m), 2.89 (3H, s), 3.01 (1H, m), 7.45 (1H, t, J=8 Hz), 8.13 (1H, d, J=8 Hz), 8.32 (1H, d, J=8 Hz)

Preparation 18 (8)

3-Chloroacetyl-2-methyl-7-nitrobenzo[b]furan mp: 167°–168° C. NMR (CDCl$_3$, δ): 2.96 (3H, s), 4.60 (2H, s), 7.50 (1H, t, J=7 Hz), 8.18 (1H, d, J=7 Hz), 8.38 (1H, d, J=7 Hz)

Preparation 19

To a mixture of 2-methyl-7-nitrobenzo[b]furan (1.77 g) and aluminum chloride (2.66 g) in dichloromethane (40 ml) was added dropwise a solution of dichloromethyl methyl ether (3.6 ml) in dichloromethane (10 ml). The mixture was stirred at ambient temperature for 30 minutes and the reaction mixture was poured into a mixture of ice and 1N-hydrochloric acid. The separated oil was extracted with dichloromethane and the extract was washed with brine, aqueous saturated sodium bicarbonate and brine. Then, the solution was dried over sodium sulfate and evaporated in vacuo. The obtained oil was crystallized from diethyl ether to give 3-formyl-2-methyl-7-nitrobenzo[b]furan (1.83 g).

mp: 166°–167° C. NMR (CDCl$_3$, δ): 2.91 (3H, s), 7.50 (1H, t, J=7 Hz), 8.18 (1H, d, J=7 Hz), 8.50 (1H, d, J=7 Hz), 10.28 (1H, s)

Preparation 20

Into a mixture of 2-methyl-7-nitrobenzo[b]furan (200 mg) and aluminum chloride (301 mg) in dichloromethane was passed hexafluoroacetone gas which was made from hexafluoroacetone trihydrate (4.7 ml) and conc. sulfuric acid (15 ml). The mixture was stirred at ambient temperature for 4 hours and then, cooled to 4° C. To the mixture was added 1N-hydrochloric acid dropwise. The organic layer was separated, washed with brine, dried over sodium sulfate and concentrated in vacuo. The residue was purified by column chromatography on silica gel and the obtained oil was crystallized from n-hexane to give 3-(1-hydroxy-2,2,2-trifluoro-1-trifluoromethylethyl)-2-methyl-7-nitrobenzo[b]furan (265 mg).

mp: 79.5°–80.5° C. NMR (CDCl$_3$, δ): 2.76 (3H, s), 3.79 (1H, s), 7.37 (1H, t, J=7.5 Hz), 8.10 (1H, m), 8.13 (1H, d, J=7.5 Hz) FAB-Mass: (m/z)=344 (M$^+$+1)

Preparation 21

A mixture of 3-chloroacetyl-2-methyl-7-nitrobenzo[b]furan (431 mg) and thiourea (194 mg) in ethanol (10 ml) was refluxed for 1.5 hours. The separated solid was collected, washed with ethanol and dried to give 3-(2-aminothiazol-4-yl)-2-methyl-7-nitrobenzo[b]furan hydrochloride (485 mg).

mp: 222°–223° C. NMR (DMSO-d$_6$,δ): 2.72 (3H, s), 7.07 (1H, s), 7.54 (1H, t, J=7 Hz), 8.18 (1H, d, J=7 Hz), 8.23 (1H, d, J=7 Hz)

Preparation 22

A mixture of 3-(2-aminothiazol-4-yl)-2-methyl-7-nitrobenzo[b]furan hydrochloride (468 mg), acetic anhydride (306 mg) and triethylamine (455 mg) in 1,2-dichloroethane (20 ml) was refluxed for 1 day. To the reaction mixture was added methanol and the mixture was evaporated in vacuo. The residue was purified by column chromatography on silica gel and the obtained oil was crystallized from diethyl ether to give 3-(2-acetylaminothiazol-4-yl)-2-methyl-7-nitrobenzo[b]furan (305 mg).

mp: 260°–261° C. NMR (DMSO-$d_6$, δ): 2.20 (3H, s), 2.81 (3H, s), 7.53 (1H, s), 7.53 (1H, t, J=7 Hz), 8.17 (1H, d, J=7 Hz), 8.46 (1H, d, J=7 Hz)

Preparation 23 (1)

A mixture of 3-formyl-2-methyl-7-nitrobenzo[b]furan (1.83 g) and sodium borohydride (200 mg) in methanol (40 ml) was stirred at ambient temperature for 2 hours. The reaction mixture was poured into cold water. The separated oil was extracted with dichloromethane. The extract was washed with brine, dried and evaporated in vacuo. The residue was purified by column chromatography on silica gel to give 3-hydroxymethyl-2-methyl-7-nitrobenzo[b]furan (1.38 g) as a solid.

mp: 129°–131° C. NMR (CDCl$_3$, δ): 1.62 (1H, t, J=6 Hz), 2.59 (3H, s), 4.83 (2H, d, J=6 Hz), 7.34 (1H, t, J=7 Hz), 7.95 (1H, d, J=7 Hz), 8.08 (1H, d, J=7 Hz)

The following compound was obtained according to a similar manner to that of Preparation 23 (1).
Preparation 23 (2)
3-(1-Ethoxycarbonyl)hydroxymethyl-2-methyl-7-nitrobenzo[b]furan mp: 73°–78° C. NMR (CDCl$_3$, δ): 1.20 (3H, t, J=8 Hz), 2.62 (3H, s), 3.46 (1H, d, J=4 Hz), 4.22 (2H, m), 5.35 (1H, d, J=4 Hz), 7.31 (1H, t, J=8 Hz), 7.85 (1H, d, J=8 Hz), 8.07 (1H, d, J=8 Hz)

Preparation 24

A mixture of 3-chloromethyl-2-methyl-7-nitrobenzo[b]furan (200 mg) and sodium thiomethoxide (68 mg) in N,N-dimethylformamide (2 ml) was stirred at ambient temperature for 2 hours. The reaction mixture was poured into cold water and the separated oil was extracted with ethyl acetate. The extract was washed with brine, dried over sodium sulfate and concentrated in vacuo. The residue was purified by column chromatography on silica gel to give 2-methyl-3-methylthiomethyl-7-nitrobenzo[b]furan (144 mg).

NMR (CDCl$_3$, δ): 2.03 (3H, s), 2.57 (3H, s), 3.78 (2H, s), 7.34 (1H, t, J=7.5 Hz), 7.92 (1H, d, J=7.5 Hz), 8.08 (1H, d, J=7.5 Hz)

Preparation 25

Sodium hydride (60%, 54 mg) was added to a solution of 3-acetylamino-2-methyl-7-nitrobenzo[b]furan (280 mg) in N,N-dimethylformamide (3 ml) at 4° C. The mixture was stirred for 30 minutes and to the mixture was added iodoethane (240 mg). The mixture was stirred at ambient temperature for 2 hours. The reaction mixture was poured into cold water and the separated oil was extracted with ethyl acetate. The extract was washed with brine, dried over sodium sulfate and concentrated in vacuo. The residue was purified by column chromatography on silica gel to give 3-(N-acetyl-N-ethylamino)-2-methyl-7-nitrobenzo[b]furan as a crystalline solid (310 mg).

mp: 114°–116° C. NMR (CDCl$_3$, δ): 1.14 (3H, t, J=7.5 Hz), 1.88 (3H, s), 2.54 (3H, s), 3.65 (1H, qd, J=7.5 and 13.5 Hz), 3.87 (1H, qd, J=7.5 and 13.5 Hz), 7.41 (1H, t, J=8 Hz), 7.69 (1H, d, J=8 Hz), 8.15 (1H, d, J=8 Hz)

Preparation 26

A solution of 3-(N-acetyl-N-ethylamino)-2-methyl-7-nitrobenzo[b]furan (310 mg) and borane-methyl sulfide complex (0.13 ml, 1.42 mmol) in tetrahydrofuran (6 ml) was stirred at 4° C. for 30 minutes, at ambient temperature for 1 hour and at 50° C. for 15 minutes. Then, the mixture was cooled to 4° C. and to the mixture was added 1N-hydrochloric acid. The mixture was stirred at ambient temperature for 1 hour and neutralized with aqueous saturated sodium bicarbonate. The separated oil was extracted with ethyl acetate. The extract was washed with brine, dried over sodium sulfate and concentrated in vacuo. The residue was is purified by column chromatography on silica gel to give 3-diethylamnino-2-methyl-7-nitrobenzo[b]furan as an oil (249 mg).

NMR (CDCl$_3$, δ): 0.99 (6H, t, J=7.5 Hz), 2.50 (3H, s), 3.23 (4H, q, J=7.5 Hz), 7.25 (1H, t, J=7.5 Hz), 7.84 (1H, d, J=7.5 Hz), 8.02 (1H, d, J=7.5 Hz)

Preparation 27 (1)

To a solution of 3-acetyl-7-amino-2-methylbenzo[b]furan (2.4 g) in dichloromethane (30 ml) was added acetic anhydride (1.6 g) dropwise. The solution was stirred at ambient temperature for 1 hour and evaporated in vacuo. Toluene was added to the residue and the solution was evaporated in vacuo. The residue was crystallized from diethyl ether to give 3-acetyl-7-acetylamino-2-methylbenzo[b]furan (2.92 g).

mp: 180°–181° C. NMR (CDCl$_3$, δ): 2.29 (3H, s), 2.63 (3H, s), 2.79 (3H, s), 7.29 (1H, t, J=7 Hz), 7.55–7.65 (2H, m), 8.13 (1H, d, J=7 Hz)

The following compound was obtained according to a similar manner to that of Preparation 27 (1).
Preparation 27(2)
6-Acetyl-1-nitro-6,7,8,9-tetrahydro-5H-10-oxo-6-aza-benzo[b]azulene mp: 106°–109° C. NMR (CDCl$_3$, δ): 2.07–2.20 (5H, m), 3.12–3.24 (2H, m), 3.79–3.92 (2H, m), 4.62 (2/3H, s), 4.81 (4/3H, s), 7.38 (1H, m), 7.75 (1/3H, d, J=8 Hz), 7.88 (2/3H, d, J=8 Hz), 8.11 (1H, m)

Preparation 28 (1)

A mixture of 7-carboxy-2,3-dimethylbenzo[b]furan (400 mg) and borane-dimethyl sulfide complex (0.4 ml) in tetrahydrofuran (6 ml) was stirred at ambient temperature for 40 hours. The mixture was quenched with 1N-hydrochloric acid and extracted with dichloromethane. The extract was washed with brine, dried over sodium sulfate and evaporated in vacuo. The residue was purified by column chromatography on silica gel and the obtained oil was crystallized from n-hexane to give 2,3-dimethyl-7-hydroxymethylbenzo[b]furan (322 mg).

mp: 64°–65° C. NMR (CDCl$_3$, δ): 1.93 (1H, t, J=7 Hz), 2.15 (3H, s), 2.40 (3H, s), 4.98 (2H, d, J=8 Hz), 7.14–7.21 (2H, m), 7.36 (1H, dd, J=1.5 and 8 Hz)

The following compound was obtained according to a similar manner to that of Preparation 28 (1).
Preparation 28 (2)
1-Nitro-6,7,8,9-tetrahydro-5H-10-oxo-6-aza-benzo[b]azulene mp: 79°–81° C. NMR (CDCl$_3$, δ): 1.90–2.00 (2H, m), 3.11–3.24 (4H, m), 4.02 (2H, s), 7.30 (1H, t, J=8 Hz), 7.68 (1H, d, J=8 Hz), 8.05 (1H, d, J=8 Hz)

Preparation 29

To a solution of 3-acetyl-7-acetylamino-2-methylbenzo[b]furan (2.92 g) in tetrahydrofuran (60 ml) was added a 3M solution of methylmagnesium bromide in diethyl ether (12.7 ml) dropwise with ice cooling. The solution was stirred at ambient temperature for 5 hours and to the solution was added aqueous saturated ammonium chloride. Then, the mixture was poured into water and the separated oil was extracted with ethyl acetate. The extract was washed with brine, dried over sodium sulfate and evaporated in vacuo. The residue was purified by column chromatography on silica gel and the obtained oil was crystallized from methanol to give 7-acetylamino-3-(1-hydroxy-1-methylethyl)-2-methylbenzo[b]furan (1.82 g).

mp: 141°–143° C. NMR (CDCl$_3$, δ): 1.20 (6H, s), 1.33 (1H, s), 2.28 (3H, s), 2.60 (3H, s), 7.14 (1H, t, J=7 Hz), 7.39 (1H, d, J=7 Hz), 7.58 (1H, br), 8.05 (1H, d, J=7 Hz)

Preparation 30

A solution of 3-formyl-2-methyl-7-nitrobenzo[b]furan (200 mg) and (carboethoxymethylene)triphenylphosphorane (434 mg) in dioxane (3 ml) was stirred at ambient temperature for 1 hour. The reaction mixture was concentrated in vacuo and the residue was purified by column chromatography on silica gel. The obtained oil was crystallized from diisopropyl ether to give 3-(2-ethoxycarbonylethenyl)-2-methyl-7-nitrobenzo[b]furan (226 mg).

mp: 148°–150° C. NMR (CDCl$_3$, δ): 1.37 (3H, t, J=7.5 Hz), 2.70 (3H, s), 4.30 (2H, q, J=7.5 Hz), 6.50 (1H, d, J=14 Hz), 7.43 (1H, t, J=8 Hz), 7.78 (1H, d, J=14 Hz), 8.09 (1H, d, J=8 Hz), 8.14 (1H, d, J=8 Hz)

Preparation 31

10%-Palladium on carbon (30 mg) was added to a solution of 3-(2-ethoxycarbonylethenyl)-2-methyl-7-nitrobenzo[b]furan (210 mg) in a mixture of dioxane (3 ml) and ethanol (1 ml). The mixture was hydrogenated at 3 atoms for 3 hours and the catalyst was filtered off. The filtrate was concentrated in vacuo to give 7-amino-3-(2-ethoxycarbonylethyl)-2-methylbenzo[b]furan (195 mg).

NMR (CDCl$_3$, δ): 1.23 (3H, t, J=7.5 Hz), 2.40 (3H, s), 2.62 (2H, t, J=7.5 Hz), 2.91 (2H, t, J=7.5 Hz), 3.89 (2H, br s), 4.12 (2H, q, J=7.5 Hz), 6.58 (1H, d, J=8 Hz), 6.87 (1H, d, J=8 Hz), 7.00 (1H, t, J=8 Hz)

Preparation 32

A solution of 3-(2-ethoxycarbonyl-3-oxobutyl)-2-methyl-7-nitrobenzo[b]furan (170 mg) in a mixture of ethanol (5 ml) and aqueous 1N-sodium hydroxide (5 ml) was refluxed for 1 hour. The reaction mixture was cooled and the separated solid was collected, washed with water and dried to give 2-methyl-7-nitro-3-(3-oxobutyl)benzo[b]furan (105 mg).

mp: 99°–100° C. NMR (CDCl$_3$, δ): 2.12 (3H, s), 2.52 (3H, s), 2.77 (2H, t, J=6 Hz), 2.92 (2H, t, J=6 Hz), 7.31 (1H, t, J=7 Hz), 7.74 (1H, d, J=7 Hz), 8.05 (1H, d, J=7 Hz)

Preparation 33

3-Hydroxymethyl-2-methyl-7-nitrobenzo[b]furan (1.0 g) was added to thionyl chloride (1.8 ml) with ice cooling. The mixture was stirred at ambient temperature for 30 minutes and concentrated in vacuo. To the residue was added toluene and the mixture was concentrated again. The residue was crystallized from a mixture of diethyl ether and n-hexane to give 3-chloromethyl-2-methyl-7-nitrobenzo[b]furan (1.01 g).

mp: 132°–133° C. NMR (CDCl$_3$, δ): 2.61 (3H, s), 4.73 (2H, s), 7.40 (1H, t, J=7 Hz), 7.91 (1H, d, J=7 Hz), 8.12 (1H, d, J=7 Hz)

Preparation 34

A mixture of 3-chloromethyl-2-methyl-7-nitrobenzo[b]furan (410 mg) and potassium phthalimide (506 mg) in N,N-dimethylformamide (10 ml) was stirred at ambient temperature for 3 hours. Then, the mixture was poured into cold water and the separated solid was collected, washed with water and dried to give 2-methyl-7-nitro-3-phthalimidomethylbenzo[b]furan (585 mg).

mp: 231°–233° C. NMR (CDCl$_3$, δ): 2.80 (3H, s), 4.92 (2H, s), 7.33 (1H, t, J=7 Hz), 7.65–7.78 (2H, m), 7.78–7.90 (2H, m), 8.04 (1H, d, J=7 Hz), 8.18 (1H, d, J=7 Hz)

Preparation 35

A mixture of 3-chloromethyl-2-methyl-7-nitrobenzo[b]furan (226 mg) and triethyl phosphite (0.52 ml) was stirred at 100° C. for 6 hours. The reaction mixture was cooled and concentrated in vacuo and to the residue was added toluene. The mixture was concentrated in vacuo and the residue was purified by column chromatography on silica gel. The obtained oil was crystallized from diisopropyl ether to give 3-(diethoxyphosphorylmethyl)-2-methyl-7-nitrobenzo[b]furan (93 mg).

mp: 102°–103° C. NMR (CDCl$_3$, δ): 1.25 (6H, t, J=7 Hz), 2.57 (3H, d, J=4 Hz), 3.15 (2H, d, J=20 Hz), 4.05 (4H, quint., J=7 Hz), 7.33 (1H, t, J=7 Hz), 7.88 (1H, d, J=7 Hz), 8.08 (1H, d, J=7 Hz)

Preparation 36

To a solution of sodium (52 mg) in ethanol (5 ml) was added ethyl acetoacetate (293 mg) and 3-chloromethyl-2-methyl-7-nitrobenzo[b]furan (339 mg). The mixture was stirred at 60° C. for 3 hours, cooled and poured into cold water. The pH of the aqueous solution was adjusted to 3 with 1N-hydrochloric acid and the separated oil was extracted with dichloromethane. The extract was washed with brine, dried over sodium sulfate and concentrated in vacuo. The residue was purified by column chromatography on silica gel and the obtained oil was crystallized from n-hexane to give 3-(2-ethoxycarbonyl-3-oxobutyl)-2-methyl-7-nitrobenzo[b]furan (205 mg).

mp: 97°–99° C. NMR (CDCl$_3$, δ): 1.21 (3H, t, J=7 Hz), 2.22 (3H, s), 2.52 (3H, s), 3.21 (3H, m), 3.79 (1H, t, J=7 Hz), 4.16 (2H, q, J=7 Hz), 7.32 (1H, t, J=7 Hz), 7.77 (1H, d, J=7 Hz), 8.07 (1H, d, J=7 Hz)

Preparation 37

A mixture of 2-methyl-7-nitro-3-phthalimidomethylbenzo[b]furan (575 mg) and hydrazine monohydrate (172 mg) in ethanol (10 ml) was refluxed for 5 hours. The reaction mixture was cooled, acidified with 1N-hydrochloric acid and filtered. The filtrate was neutralized with aqueous saturated sodium bicarbonate and the ethanol in the mixture was evaporated in vacuo. The separated solid was collected, washed with water and dried to give 3-aminomethyl-2-methyl-7-nitrobenzo[b]furan (290 mg).

mp: 134°–138° C. NMR (CDCl$_3$:CD$_3$OD=9:1, δ): 2.58 (3H, s), 3.95 (2H, s), 7.38 (1H, t, J=7 Hz), 7.91 (1H, d, J=7 Hz), 8.09 (1H, d, J=7 Hz)

Preparation 38 (1)

A solution of 5,7-diamino-2,3-dimethylbenzo[b]furan (970 mg), di-tert-butyl dicarbonate (2.0 g) and triethylamine (668 mg) in dichloromethane was stirred at ambient temperature for 8 hours. The reaction mixture was evaporated in vacuo and the residue was purified by column chromatography on silica gel. The obtained oil was crystallized from a mixture of diethyl ether and n-hexane to give 7-amino-5-(tert-butoxycarbonylamino)-2,3-dimethylbenzo[b]furan (1.10 g).

mp: 177°–178° C. NMR (CDCl$_3$, δ): 1.51 (9H, s), 2.09 (3H, s), 2.32 (3H, s), 3.85 (2H, br s), 6.39 (1H, s), 6.60 (1H, s), 6.84 (1H, s)

Preparation 38 (2)

A mixture of 3-aminomethyl-2-methyl-7-nitrobenzo[b]furan (278 mg) and di-tert-butyl dicarbonate (353 mg) in dichloromethane (5 ml) was stirred at ambient temperature for overnight. The reaction mixture was concentrated in vacuo and the residue was purified by column chromatography on silica gel. The obtained oil was crystallized from a mixture of diisopropyl ether and n-hexane to give 3-tert-butoxycarbonylaminomethyl-2-methyl-7-nitrobenzo[b]furan (313 mg).

mp: 120°–122° C. NMR (CDCl$_3$, δ): 1.46 (9H, s), 2.58 (3H, s), 4.41 (2H, d, J=6 Hz), 4.72 (1H, br s), 7.33 (1H, t, J=7 Hz), 7.90 (1H, d, J=7 Hz), 8.08 (1H, d, J=7 Hz)

Preparation 39 (1)

A mixture of 3-acetyl-2-methyl-7-nitrobenzo[b]furan (413 mg), hydroxylamine hydrochloride (393 mg) and sodium bicarbonate (792 mg) in ethanol (10 ml) was refluxed for 30 minutes. The reaction mixture was cooled and water was added to the solution. The separated solid was collected, washed with water and dried to give 3-(1-hydroxyiminoethyl)-2-methyl-7-nitrobenzo[b]furan (320 mg).

mp: 158°–162° C.

The following compound was obtained according to a similar manner to that of Preparation 39 (1).

Preparation 39 (2)

1-Hydroxyimino-6-nitro-1,2,3,4-tetrahydrodibenzofuran mp: 174° C. (dec.) NMR (CDCl$_3$, δ): 2.07–2.20 (2H, m), 2.86 (2H, t, J=6 Hz), 3.01 (2H, t, J=6 Hz), 7.38 (1H, t, J=8 Hz), 8.11 (1H, d, J=8 Hz), 8.29 (1H, d, J=8 Hz)

Preparation 40 (1)

A solution of 3-(1-hydroxyiminoethyl)-2-methyl-7-nitrobenzo[b]furan (200 mg) in trifluoroacetic acid (3 ml) was refluxed for 1.5 hours. The reaction mixture was concentrated in vacuo and the residue was crystallized from a mixture of methanol and water to give 3-acetylamino-2-methyl-7-nitrobenzo[b]furan (185 mg).

mp: >250° C. NMR (CDCl$_3$:CD$_3$OD=1:1, δ): 2.23 (3H, s), 2.50 (3H, s), 7.33 (1H, t, J=7 Hz), 7.75 (1H, d, J=7 Hz), 8.70 (1H, d, J=7 Hz)

Preparation 40 (2)

A solution of 6-nitro-1,2,3,4-tetrahydro-1-p-toluenesulfonyloxyiminodibenzofuran (1.1 g) in trifluoroacetic acid (22 ml) was refluxed for 3 hours. The mixture was evaporated in vacuo and poured into a mixture of ice and water. The separated oil was extracted with chloroform. The extract was washed with aqueous saturated sodium bicarbonate, dried over sodium sulfate and evaporated in vacuo. The residue was purified by column chromatography on silica gel and the obtained crude solid was triturated with a hot mixture of ethyl acetate and n-hexane (1:1) to give 1-nitro-6,7,8,9-tetrahydro-5H-10-oxo-6-aza-benzo[b]azulen-5-one (550 mg).

mp: 230°–233° C. NMR (CDCl$_3$, δ): 2.21–2.31 (2H, m), 3.33 (2H, t, J=6 Hz), 3.50 (2H, q, J=5 Hz), 6.33 (1H, m), 7.42 (1H, t, J=8 Hz), 8.13 (1H, d, J=8 Hz), 8.63 (1H, d, J=8 Hz)

Preparation 41

A mixture of 6-nitro-1-oxo-1,2,3,4-tetrahydrodibenzofuran (300 mg) and sodium azide (102 mg) in trifluoroacetic acid (3 ml) was stirred at 60° C. for 5 hours. The reaction mixture was concentrated in vacuo and the residue was purified by column chromatography on silica gel. The obtained oil was crystallized from diisopropyl ether to give 1-nitro-6,7,8,9-tetrahydro-5H-10-oxo-5-aza-benzo[b]azulen-6-one (70 mg).

mp: >250° C. NMR (CDCl$_3$, δ): 2.14 (2H, m), 2.68–2.78 (2H, m), 3.20 (2H, t, J=6 Hz), 7.40 (1H, t, J=8 Hz), 7.99 (1H, d, J=8 Hz), 8.12 1 (1H, d, J=8 Hz)

Preparation 42 (1)

To a solution of 3-bromo-2-methyl-7-nitrobenzo[b]furan (300 mg) and acetic acid (776 mg) in a mixture of ethanol (6 ml) and dioxane (1.5 ml) was added iron (722 mg) at 50° C. The mixture was refluxed for 1.5 hours and the insoluble material was filtered off. The filtratate was evaporated in vacuo with toluene. The residue was extracted with a mixture of ethyl acetate and saturated aqueous sodium bicarbonate. The organic layer was separated and it was extracted with ethyl acetate from aqueous layer. The organic layer was combined and washed with saturated aqueous sodium bicarbonate, brine, dried over sodium sulfate, and evaporated in vacuo to give 7-amino-3-bromo-2-methylbenzo[b]furan (262 mg) as a white solid.

mp: 70°–71° C. NMR (CDCl$_3$, δ): 2.48 (3H, s), 3.82 (2H, br s), 6.63 (1H, dd, J=1 and 8 Hz), 6.86 (1H, dd, J=1 and 8 Hz), 7.09 (1H, t, J=8 Hz)

The following compounds [Preparations 42 (2) to (14)] were obtained according to a similar manner to that of Preparation 42 (1).

Preparation 42 (2)

3-Acetyl-7-amino-2-methylbenzo[b]furan mp:112°–113° C. NMR (CDCl$_3$, δ): 2.63 (3H, s), 2.73 (3H, s), 3.95 (2H, br s), 6.66 (1H, d, J=7 Hz), 7.12 (1H, t, J=7 Hz), 7.29 (1H, d, J=7 Hz)

Preparation 42 (3)

7-Amino-3-hydroxymethyl-2-methylbenzo[b]furan mp: 117°–121° C. NMR (CDCl$_3$, δ): 1.51 (1H, t, J=5 Hz), 2.45 (3H, s), 3.90 (2H, br s), 4.72 (2H, d, J=5 Hz), 6.60 (1H, d, J=7 Hz), 6.95–7.10 (2H, m)

Preparation 42 (4)

3-Acetyl-7-amino-5-fluoro-2-methylbenzo[b]furan mp: 133°–134° C. NMR (CDCl$_3$, δ): 2.59 (3H, s), 2.76 (3H, s), 4.05 (2H, br s), 6.39 (1H, d, J=8 Hz), 6.97 (1H, d, J=8 Hz)

Prefoaration 42 (5)

6-Amino-3,4-dihydro-1H-thiopyrano[4,3-b]benzo[b]furan

NMR (CDCl$_3$, δ): 3.02 (4H, s), 3.75 (2H, s), 3.90 (2H, br s), 6.62 (1H, dd, J=1 and 8 Hz), 6.83 (1H, dd, J=1 and 8 Hz), 7.02 (1H, t, J=8 Hz)

Preparation 42 (6)

6-Amino-1,2-dihydro-1-oxo-4H-thiopyrano[3,4-b]benzo[b]furan mp: 161°–163° C. NMR (CDCl$_3$, δ): 3.49 (2H, s), 3.92 (2H, br s), 3.99 (2H, s), 6.70 (1H, d, J=8 Hz), 7.15 (1H, t, J=8 Hz), 7.48 (1H, d, J=8 Hz)

Preparation 42 (7)

7-Amino-2-methyl-3-methylthiomethylbenzo[b]furan

NMR (CDCl$_3$, δ): 2.00 (3H, s), 2.43 (3H, s), 3.71 (2H, s), 3.80–3.97 (2H, m), 6.60 (1H, d, J=7 Hz), 6.97–7.04 (2H, m)

Preparation 42 (8)

3-Acetyl-7-amino-5-chloro-2-methylbenzo[b]furan mp: 162°–163° C. NMR (CDCl$_3$, δ): 2.60 (3H, s), 2.76 (3H, s), 4.02 (2H, br s), 6.65 (1H, s), 7.28 (1H, s)

Preparation 42 (9)

7-Amino-3-butyryl-2-methylbenzo[b]furan mp: 109°–111° C. NMR (CDCl$_3$, δ): 1.04 (3H, t, J=7 Hz), 1.80 (2H, sex, J=7 Hz), 2.77 (3H, s), 2.91 (2H, t, J=7 Hz), 3.46 (2H, br s), 6.77 (1H, d, J=8 Hz), 7.12 (1H, t, J=8 Hz), 7.27 (1H, m)

Preparation 42 (10)

7-Amino-3-(1-ethoxycarbonyl)hydroxymethyl-2-methylbenzo[b]furan mp: 103°–105° C. NMR (CDCl$_3$, δ): 1.19 (3H, t, J=8 Hz), 2.49 (3H, s), 3.37 (1H, br s), 3.88 (2H, br s), 4.21 (2H, m), 5.28 (1H, s), 6.58 (1H, d, J=8 Hz), 6.90 (1H, d, J=8 Hz), 6.98 (1H, t, J=8 Hz)

Preparation 42 (11)

7-Amino-3-(2-ethoxycarbonylethenyl)-2-methylbenzo[b]furan mp: 103°–105° C. NMR (CDCl$_3$, δ): 1.35 (3H, t, J=7.5 Hz), 2.57 (3H, s), 3.94 (2H, br s), 4.29 (2H, q, J=7.5 Hz), 6.48 (1H, d, J=14 Hz), 6.66 (1H, d, J=8 Hz), 7.10 (1H, t, J=8 Hz), 7.19 (1H, d, J=8 Hz), 7.77 (1H, d, J=14 Hz)

Preparation 42 (12)

6-Amino-1-oxo-1,2,3,4-tetrahydrodibenzofuran mp: 118°–119.5° C. NMR (CDCl$_3$, δ): 2.28 (2H, quint., J=7 Hz), 2.60 (2H, t, J=7 Hz), 3.03 (2H, t, J=7 Hz), 3.95 (2H, m), 6.68 (1H, d, J=8 Hz), 7.12 (1H, d, J=8 Hz), 7.45 (1H, d, J=7 Hz)

Preparation 42 (13)

7-Amino-3-ethoxycarbonylmethyl-2-methylbenzo[b]furan

NMR (CDCl$_3$, δ): 1.23 (3H, t, J=7 Hz), 2.42 (3H, s), 3.57 (2H, s), 3.88 (2H, br s), 4.14 (2H, q, J=7 Hz), 6.58 (1H, d, J=8 Hz), 6.90 (1H, d, J=8 Hz), 7.00 (1H, t, J=8 Hz)

Preparation 42 (14)

7-Amino-3-bromo-2-(2-ethoxycarbonylethyl)-benzo[b]furan NMR (CDCl$_3$, δ): 1.26 (3H, t, J=7 Hz), 2.76 (2H, t, J=7 Hz), 3.17 (2H, t, J=7 Hz), 3.91 (2H, br s), 4.17 (2H, q, J=7 Hz), 6.64 (1H, d, J=8 Hz), 6.88 (1H, d, J=8 Hz), 7.09 (1H, t, J=8 Hz)

Preparation 43 (1)

To a solution of 2-ethyl-3-methyl-7-nitrobenzo[b]furan (1.00 g) in a mixture of methanol (15 ml) and dioxane (10 ml) was added 10% palladium carbon (100 mg) and the above mixture was hydrogenated at 3 atom for 1 hour. The catalyst was filtered off and the filtrate was evaporated in vacuo to give 7-amino-2-ethyl-3-methylbenzo[b]furan (858 mg) as an oil.

NMR (CDCl$_3$, δ): 1.30 (3H, t, J=8 Hz), 2.14 (3H, s), 2.74 (2H, q, J=8 Hz), 3.88 (2H, br s), 6.59 (1H, d, J=6 Hz), 6.86 (1H, d, J=6 Hz), 7.01 (1H, t, J=6 Hz)

The following compounds [Preparations 43 (2) to (17)] were obtained according to a similar manner to that of Preparation 43 (1).

Preparation 43 (2)

7-Amino-2-methyl-3-propionylbenzo[b]furan mp: 126°–127° C. NMR (CDCl$_3$, δ): 1.25 (3H, t, J=7 Hz), 2.78 (3H, s), 2.98 (2H, q, J=7 Hz), 3.97 (2H, br s), 6.66 (1H, t, J=7 Hz), 7.12 (1H, d, J=7 Hz), 7.28 (1H, d, J=7 Hz)

Preparation 43 (3)

7-Amino-2,3-dimethyl-5-ethoxycarbonylbenzo[b]furan mp: 137°–140° C. NMR (CDCl$_3$, δ): 1.42 (3H, t, J=8 Hz), 2.15 (3H, s), 2.39 (3H, s), 3.95 (2H, br s), 4.38 (2H, q, J=8 Hz), 7.30 (1H, s), 7.60 (1H, s)

Preparation 43 (4)

7-Amino-3-(diethoxyphosphorylmethyl)-2-methylbenzo[b]furan mp: 105°–109° C. NMR (CDCl$_3$, δ): 1.22 (6H, t, J=7 Hz), 2.46 (3H, d, J=4 Hz), 3.10 (2H, d, J=20 Hz), 3.89 (2H, br s), 4.01 (4H, quint., J=7 Hz), 6.59 (1H, d, J=7 Hz), 6.93 (1H, d, J=7 Hz), 7.01 (1H, t, J=7 Hz)

Preparation 43 (5)

3-Acetylamino-7-amino-2-methylbenzo[b]furan mp: 183°–184° C. NMR (CDCl$_3$:CD$_3$OD=9:1, δ): 2.20 (3H, s), 2.37 (3H, s), 6.60 (1H, d, J=7 Hz), 6.80 (1H, d, J=7 Hz), 7.00 (1H, t, J=7 Hz)

Preparation 43 (6)

7-Amino-3-tert-butoxycarbonylaminomethyl-2-methylbenzo[b]furan mp: 110°–111° C. NMR (CDCl$_3$, δ): 1.46 (9H, s), 2.45 (3H, s), 3.90 (2H, br s), 4.33 (2H, d, J=6 Hz), 4.65 (1H, br), 6.60 (1H, d, J=7 Hz), 6.92 (1H, d, J=7 Hz), 7.03 (1H, t, J=7 Hz)

Preparation 43 (7)

7-Amino-2-methyl-3-(3-oxobutyl)benzo[b]furan mp: 75°–76° C. NMR (CDCl$_3$, δ): 2.12 (3H, s), 2.40 (3H, s), 2.77 (2H, m), 2.85 (2H, m), 3.89 (2H, br s), 6.58 (1H, d, J=7 Hz), 6.83 (1H, d, J=7 Hz), 7.00 (1H, t, J=7 Hz)

Preparation 43 (8)

7-Amino-3-diethylamino-2-methylbenzo[b]furan NMR (CDCl$_3$, δ): 0.96 (6H, t, J=7.5 Hz), 2.38 (3H, s), 3.10 (4H, q, J=7.5 Hz), 3.89 (2H, br s), 6.55 (1H, d, J=7.5 Hz), 6.29 (1H, d, J=7.5 Hz), 6.98 (1H, t, J=7.5 Hz)

Preparation 43 (9)

7-Amino-3-(1-hydroxy-2,2,2-trifluoro-1-trifluoromethylethyl)-2-methylbenzo[b]furan mp: 167.5°–168.5° NMR (CDCl$_3$, δ): 2.00 (3H, br s), 2.63 (3H, s), 6.53 (1H, d, J=7.5 Hz), 7.02 (1H, t, J=7.5 Hz), 7.16 (1H, d, J=7.5 Hz) FAB-Mass: (m/z)=314 (M$^+$+1)

Preparation 43 (10)

7-Amino-3-benzoyl-2-methylbenzo[b]furan mp: 150°–151° C. NMR (CDCl$_3$, δ): 2.57 (3H, s), 3.97 (2H, br s), 6.63 (1H, d, J=8 Hz), 6.73 (1H, d, J=8 Hz), 6.99 (1H, t, J=8 Hz), 7.48 (2H, t, J=8 Hz), 7.59 (1H, t, J=8 Hz), 7.80 (2H, d, J=8 Hz)

Preparation 43 (11)

7-Amino-3-cyclohexylcarbonyl-2-methylbenzo[b]furan mp: 125°–126° C. NMR (CDCl$_3$, δ): 1.20–1.55 (5H, m), 1.60–2.05 (5H, m), 2.87 (3H, s), 3.06 (1H, m), 3.97 (2H, br s), 6.65 (1H, d, J=8 Hz), 7.11 (1H, t, J=8 Hz), 7.18 (1H, d, J=8 Hz)

Preparation 43 (12)

6-Amino-1,2,3,4-tetrahydrodibenzofuran NMR (CDCl$_3$, δ): 1.77–2.00 (4H, m), 2.54–2.79 (4H, m), 3.86 (2H, m), 6.58 (1H, d, J=8 Hz), 6.84 (1H, d, J=8 Hz), 7.00 (1H, t, J=8 Hz)

Preparation 43 (13)

1-Amino-6,7,8,9-tetrahydro-5H-10-oxo-benzo[b]azulene mp: 89°–94° C. NMR (CDCl$_3$, δ): 1.73–1.89 (6H, m), 2.65 (2H, t, J=5 Hz), 2.91 (2H, t, J=5 Hz), 3.86 (2H, br s), 6.55 (1H, d, J=8 Hz), 6.83 (1H, d, J=8 Hz), 7.00 (1H, t, J=8 Hz)

Preparation 43 (14)

1-Amino-6,7,8,9-tetrahydro-5H-10-oxo-5-aza-benzo[b]azulen-6-one mp: 220°–223° C. NMR (CDCl$_3$, δ): 2.11–2.20 (2H, m), 2.71 (2H, t, J=6 Hz), 3.06 (2H, t, J=6 Hz), 3.82 (2H, br s), 6.63 (1H, d, J=8 Hz), 6.83 (1H, d, J=8 Hz), 7.05 (1H, t, J=8 Hz), 7.43 (1H, br s)

Preparation 43 (15)

6-Amino-1-hydroxy-1,2,3,4-tetrahydrodibenzofuran mp: 127°–128° C. NMR (CDCl$_3$, δ): 1.8–2.2 (4H, m), 2.6–2.9 (2H, m), 3.90 (2H, br s), 5.02 (1H, m), 6.62 (1H, t, J=4 Hz), 7.05 (2H, d, J=4 Hz)

Preparation 43 (16)

3-(2-Acetylaminothiazol-4-yl)-7-amino-2-methylbenzo[b]furan mp: 203°–204° C. NMR (CDCl$_3$:CD$_3$OD=9:1, δ): 2.22 (3H, s), 2.65 (3H, s), 6.68 (1H, d, J=7 Hz), 7.01 (1H, s), 7.07 (1H, t, J=7 Hz), 7.19 (1H, d, J=7 Hz)

Preparation 43 (17)

6-Acetyl-1-amino-6,7,8,9-tetrahydro-5H-10-oxo-6-azabenzo[b]azulene mp: 137°–140° C. NMR (CDCl$_3$, δ): 1.98–2.17 (5H, m), 2.97–3.08 (2H, m), 3.70–4.00 (4H, m), 4.51 (4/3H, s), 4.75 (2/3H, s), 6.60 (1H, t, J=8 Hz), 6.81–7.08 (2H, m)

Preparation 44

To a suspension of 5,7-bis(benzoylamino)-dimethylbenzo[b]furan (2.5 g) in ethanol (18 ml) was added conc. hydrochloric acid (9 ml) and the mixture was refluxed for 36 hours. The reaction mixture was cooled and evaporated in vacuo. The residue was dissolved in water and the solution was washed with ethyl acetate. The aqueous layer was neutralized with aqueous saturated sodium bicarbonate and the separated oil was extracted with ethyl acetate. The extract was washed with brine, dried over sodium sulfate and evaporated in vacuo to give 5,7-diamino-2,3-dimethylbenzo[b]furan.

mp: 151°–152° C. NMR (CDCl$_3$, δ): 2.03 (3H, s), 2.31 (3H, s), 6.00 (1H, s), 6.15 (1H, s)

Preparation 45 (1)

A suspension of 7-acetylamino-3-(1-hydroxy-1-methylethyl)-2-methylbenzo[b]furan (1.82 g) in a mixture of ethanol (15 ml) and 3N-aqueous sodium hydroxide (10 ml) was refluxed for 20 hours. The reaction mixture was cooled, diluted with water (20 ml) and evaporated in vacuo until the ethanol of the solution was removed. The separated solid was collected, washed with water and dried to give 7-amino-3-(1-hydroxy-1-methylethyl)-2-methylbenzo[b]furan (1.42 g).

mp: 127°–128° C. NMR (CDCl$_3$, δ): 1.70 (6H, s), 1.84 (1H, s), 2.59 (3H, s), 3.90 (2H, br s), 6.58 (1H, d, J=7 Hz), 6.99 (1H, t, J=7 Hz), 7.09 (1H, d, J=7 Hz)

The following compound was obtained according to a similar manner to that of Preparation 45 (1).

Preparation 45 (2)

7-Amino-2,3-dimethyl-5-nitrobenzo[b]furan mp: 156°–157° C. NMR (CDCl$_3$, δ): 2.17 (3H, s), 2.41 (3H, s), 4.12 (2H, br s), 7.48 (1H, d, J=2 Hz), 7.29 (1H, d, J=2 Hz)

Example 1 (1)

A mixture of 7-amino-2-ethyl-3-methylbenzo[b]furan (858 mg), 2,6-dichlorobenzoyl chloride (1.23 g) and triethylamine (1.23 g) in 1,2-dichloroethane (17 ml) was stirred for 3 hours at 70° C. The mixture was diluted with dichloromethane, washed with diluted hydrochloric acid and brine, dried over sodium sulfate, and evaporated in vacuo to give a solid. The residue solid was crystallized from a mixture of ethanol (20 ml) and water (2 ml) to give 7-(2,6-dichlorobenzoylamino)-2-ethyl-3-methylbenzo[b]furan (610 mg).

mp: 169°–170° C. NMR (CDCl$_3$, δ): 1.27 (3H, t, J=7 Hz), 2.18 (3H, s), 2.74 (2H, q, J=7 Hz), 7.23 (2H, m), 7.29–7.44 (3H, m), 7.81 (1H, br s), 8.28 (1H, m)

The following compounds [Examples 1 (2) to (76)] were obtained according to a similar manner to that of Example 1 (1)

Example 1 (2)

7-(2,6-Dichlorobenzoylamino)-2-methylbenzo[b]furan mp: 169°–171° C. NMR (CDCl$_3$, δ): 2.46 (3H, s), 6.40 (1H, m), 7.18–7.29 (2H, m), 7.32–7.44 (3H, m), 7.82 (1H, br s), 8.29 (1H, dd, J=1 and 8 Hz)

Example 1 (3)

7-(2,6-Dichlorobenzoylamino)-2,3-dimethylbenzo[b]furan mp: 195°–196° C. NMR (CDCl$_3$, δ): 2.16 (3H, s), 2.38 (3H, s), 7.23 (2H, m), 7.33–7.44 (3H, m), 7.81 (1H, br s), 8.28 (1H, m)

Example 4 (4)

3-Bromo-7-(2,6-dichlorobenzoylamino)-2-methylbenzo[b]furan mp: 218°–219° C. NMR (CDCl$_3$, δ): 2.49 (3H, s), 7.21–7.30 (2H, m), 7.30–7.45 (3H, m), 7.80 (1H, br s), 8.35 (1H, dd, J=1 and 8 Hz)

Example 1 (5)

7-(2,6-Dichlorobenzoylamino)-2,3-dimethylbenzo-[b]thiophene mp: 235°–236° C. NMR (CDCl$_3$, δ): 2.32 (3H, s), 2.50 (3H, s), 7.30–7.53 (6H, m), 7.90 (1H, dd, J=1 and 8 Hz)

Example 1 (6)

7-(2,6-Dichlorobenzoylamino)-2,3-dimethyl-5-ethoxycarbonylbenzo[b]furan mp: 192°–193° C. NMR (CDCl$_3$, δ): 1.43 (3H, t, J=8 Hz), 2.20 (3H, s), 2.40 (3H, s), 4.44 (2H, q, J=8 Hz), 7.25–7.45 (3H, m), 7.82 (1H, br s), 8.02 (1H, s), 8.94 (1H, s)

Example 1 (7)

5-(tert-Butoxycarbonylamino)-7-(2,6-dichlorobenzoylamino)-2,3-dimethylbenzo[b]furan mp: 192°–194° C. NMR (CDCl$_3$, δ): 1.53 (9H, s), 2.12 (3H, s), 2.35 (3H, s), 6.60 (1H, s), 7.30–7.45 (3H, s), 7.68 (1H, s), 7.80 (1H, s), 7.98 (1H, s)

Example 1 (8)

3-Acetyl-7-(2,6-dichlorobenzoylamino)-2-methylbenzo[b]furan mp: 216°–217° C. NMR (CDCl$_3$, δ): 2.67 (3H, s), 2.79 (3H, s), 7.30–7.50 (4H, m), 7.72 (1H, d, J=7 Hz), 7.83 (1H, br s), 8.35 (1H, d, J=7 Hz)

Example 1 (9)

7-(2,6-Dichlorobenzoylamino)-3-hydroxymethyl-2-methylbenzo[b]furan mp: 183°–184° C. NMR (CDCl$_3$:CD$_3$OD=9:1, δ): 2.46 (3H, s), 4.72 (2H, s), 7.25 (1H, t, J=7 Hz), 7.30–7.50 (4H, m), 8.16 (1H, d, J=7 Hz)

Example 1 (10)

7-(2,6-Dichlorobenzoylamino)-2-methyl-3-propionylbenzo[b]furan mp: 216°–217° C. NMR (CDCl$_3$, δ): 1.28 (3H, t, J=7 Hz), 2.79 (3H, s), 2.99 (2H, q, J=7 Hz), 7.30–7.45 (4H, m), 7.70 (1H, d, J=7 Hz), 7.83 (1H, br s), 8.36 (1H, d, J=7 Hz)

Example 1 (11)

7-(2,6-Dichloro-3-methoxybenzoylamino)-3-(1-hydroxy-1-methylethyl)-2-methylbenzo[b]furan mp: 167°–168° C. NMR (CDCl$_3$, δ): 1.71 (6H, s), 1.80 (1H, s), 2.58 (3H, s), 3.94 (3H, s), 6.96 (1H, d, J=8 Hz), 7.22 (1H, t, J=8 Hz), 7.35 (1H, d, J=8 Hz), 7.46 (1H, d, J=8 Hz), 7.79 (1H, br s), 8.29 (1H, d, J=8 Hz)

Example 1 (12)

3-Acetyl-7-(2,6-dichlorobenzoylamino)-5-fluoro-2-methylbenzo[b]furan mp: 223°–229° C. NMR (CDCl$_3$, δ): 2.62 (3H, s), 2.77 (3H, s), 7.30–7.45 (4H, m), 7.84 (1H, br s), 8.22 (1H, d, J=9 Hz)

Example 1 (13)

3-Acetyl-7-(2-chloro-6-methylbenzoylamino)-2-methylbenzo[b]furan mp: 181°–182° C. NMR (CDCl₃, δ): 2.48 (3H, s), 2.66 (3H, s), 2.78 (3H, s), 7.21 (1H, m), 7.32 (2H, d, J=6 Hz), 7.38 (1H, t, J=8 Hz), 7.70 (1H, d, J=8 Hz), 7.80 (1H, br s), 8.35 (1H, d, J=8 Hz)

Example 1 (14)

7-(2,6-Dichlorobenzoylamino)-3-(diethoxyphosphorylmethyl)-2-methylbenzo[b]furan mp: 172°–174° C. NMR (CDCl₃, δ): 1.25 (6H, t, J=7 Hz), 2.45 (3H, d, J=4 Hz), 3.12 (2H, d, J=20 Hz), 4.03 (4H, quint., J=7 Hz), 7.20–7.45 (5H, m), 7.82 (1H, br s), 8.30 (1H, d, J=7 Hz)

Example 1 (15)

6-(2,6-Dichloro-3-nitrobenzoylamino-1,2,3,4-tetrahydrodibenzofuran mp: 244°–245° C. NMR (CDCl₃, δ): 1.81–2.00 (4H, m), 2.60–2.69 (2H, m), 2.69–2.77 (2H, m), 7.24–7.29 (2H, m), 7.56 (1H, dd, J=4 and 8 Hz), 7.86–7.93 (2H, m), 8.23 (1H, m)

Example 1 (16)

6-(2,6-Dichlorobenzoylamino)-1,2,3,4-tetrahydrodibenzofuran mp: 195°–196° C. NMR (CDCl₃, δ): 1.78–2.01 (4H, m), 2.59–2.77 (4H, m), 7.20–7.30 (2H, m), 7.32–7.43 (3H, m), 7.85 (1H, br s), 8.30 (1H, m)

Example 1 (17)

6-(2,6-Dichlorobenzoylamino)-3,4-dihydro-1H-thiopyrano[4,3-b]benzofuran mp: 215°–216° C. NMR (CDCl₃, δ): 3.00–3.06 (4H, m), 3.78 (2H, br s), 7.20–7.31 (3H, m), 7.32–7.46 (2H, m), 7.82 (1H, br s), 8.43 (1H, dd, J=1 and 6 Hz)

Example 1 (18)

6-(3,5-Dichloroisonicotinoylamino)-1,2,3,4-tetrahydrodibenzofuran mp: 201°–203° C. NMR (CDCl₃, δ): 1.82–2.00 (4H, m), 2.60–2.68 (2H, m), 2.68–2.77 (2H, m), 7.25 (2H, m), 7.88 (1H, br s), 8.22 (1H, dd, J=1 and 7 Hz), 8.60 (2H, s)

Example 1 (19)

6-(2,6-Dichlorobenzoylamino)-1,2-dihydro-1-oxo-4H-thiopyrano[3,4-b]enzo[b]furan mp: >250° C. NMR (CDCl₃, δ): 3.52 (2H, s), 4.00 (2H, s), 7.30–7.45 (4H, m), 7.77 (1H, br s), 7.90 (1H, d, J=8 Hz), 8.33 (1H, d, J=8 Hz)

Example 1 (20)

6-(2-Chloro-6-methylbenzoylamino)-1-hydroxy-1,2,3,4-tetrahydrodibenzo furan mp: 179°–180° C. NMR (CDCl₃, δ): 1.71 (1H, d, J=7.5 Hz), 1.85–2.20 (4H, m), 2.46 (3H, s), 2.72 (2H, m), 5.05 (1H, m), 7.18 (1H, d, J=7.5 Hz), 7.2–7.35 (3H, m), 7.42 (1H, d, J=7.5 Hz), 7.80 (1H, br s), 8.30 (1H, d, J=7.5 Hz)

Example 1 (21)

6-(2-Bromo-6-methylbenzoylamino)-1-hydroxy-1,2,3,4-tetrahydrodibenzofuran mp: 186°–187° C. NMR (CDCl₃, δ): 1.71 (1H, d, J=7.5 Hz), 1.8–2.2 (4H, m), 2.47 (3H, s), 2.73 (2H, m), 5.05 (1H, br s), 7.15–7.25 (2H, m), 7.30 (1H, d, J=7.5 Hz), 7.43 (1H, d, J=7.5 Hz), 7.45 (1H, t, J=7.5 Hz), 7.77 (1H, br s), 8.30 (1H, d, J=7.5 Hz)

Example 1 (22)

1-(2,6-Dichlorobenzoylamino)-6,7,8,9-tetrahydro-5H-10-oxobenzo[b]azulene mp: 191°–192° C. NMR (CDCl₃, δ): 1.72–1.90 (6H, m), 2.63–2.73 (2H, m), 2.87–2.95 (2H, m), 7.19–7.28 (2H, m), 7.30–7.42 (3H, m), 7.80 (1H, br s), 8.27 (1H, d, J=8 Hz)

Example 1 (23)

1-(2,6-Dichlorobenzoylamino)-6,7,8,9-tetrahydro-5H-10-oxo-5-azabenzo[b]azulen-6-one mp: >250° C. NMR (CDCl₃, δ): 2.12–2.21 (2H, m), 2.70 (2H, t, J=6 Hz), 3.07 (2H, t, J=6 Hz), 7.30 (1H, t, J=8 Hz), 7.34–7.45 (4H, m), 8.19 (1H, d, J=8 Hz)

Example 1 (24)

6-(2,6-Dichlorobenzoylamino)-1-oxo-1,2,3,4-tetrahydrodibenzofuran mp: >250° C. NMR (CDCl₃, δ): 2.29 (2H, quint., J=7 Hz), 2.29 (2H, t, J=7 Hz), 3.04 (2H, t, J=7 Hz), 7.34–7.44 (4H, m), 7.80 (1H, br s), 7.87 (1H, d, J=8 Hz), 8.32 (1H, d, J=8 Hz)

Example 1 (25)

7-(2,6-Dichlorobenzoylamino)-2,3-dimethyl-5-nitrobenzo[b]furan mp: >250° C. NMR (CDCl₃, δ): 2.21 (3H, s), 2.43 (3H, s), 7.35–7.47 (3H, m), 7.89 (1H, br s), 8.19 (1H, d, J=2 Hz), 9.24 (1H, d, J=2 Hz)

Example 1 (26)

3-Acetylamino-7-(2,6-dichlorobenzoylamino)-2-methylbenzo[b]furan mp: >250° C. NMR (DMSO-d₆, δ): 2.09 (3H, s), 2.33 (3H, s), 7.15–7.30 (2H, m), 7.40–7.65 (3H, m), 7.78 (1H, d, J=7 Hz), 9.58 (1H, s)

Example 1 (27)

3-tert-Butoxycarbonylaminomethyl-7-(2,6-dichlorobenzoylamino)-2-methylbenzo[b]furan mp: 188°–189° C. NMR (CDCl₃, δ): 1.46 (9H, s), 2.45 (3H, s), 4.38 (2H, d, J=6 Hz), 4.70 (1H, br s), 7.20–7.45 (5H, m), 7.82 (1H, br s), 8.31 (1H, d, J=7 Hz)

Example 1 (28)

7-(2,6-Dichlorobenzoylamino)-3-diethylamino-2-methylbenzo[b]furan mp: 134°–135° C. NMR (CDCl₃, δ): 0.97 (6H, t, J=7.5 Hz), 2.38 (3H, s), 3.12 (4H, q, J=7.5 Hz), 7.19 (1H, t, J=7.5 Hz), 7.13–7.43 (4H, m), 7.84 (1H, br s), 8.28 (1H, d, J=7.5 Hz)

Example 1 (29)

7-(2,6-Dichlorobenzoylamino)-2-methyl-3-(3-oxobutyl)benzo[b]furan mp: 209°–210° C. NMR (CDCl₃, δ): 2.12 (3H, s), 2.41 (3H, s), 2.80 (2H, t, J=6 Hz), 2.88 (2H, t, J=6 Hz), 7.20–7.30 (2H, m), 7.30–7.40 (3H, m), 7.81 (1H, br s), 8.30 (1H, d, J=7 Hz)

Example 1 (30)

3-Acetyl-5-chloro-7-(2,6-dichlorobenzoylamino)-2-methylbenzo[b]furan mp: 241°–242° C. NMR (CDCl₃, δ): 2.63 (3H, s), 2.78 (3H, s), 7.30–7.45 (3H, m), 7.73 (1H, s), 7.80 (1H, br s), 8.43 (1H, s)

Example 1 (31)

7-(2,6-Dichlorobenzoylamino)-3-(2-ethoxycarbonylethyl)-2-methylbenzo[b]furan mp: 132°–134° C. NMR (CDCl₃, δ): 1.23 (3H, t, J=6.5 Hz), 2.42 (3H, s), 2.64 (2H, t, J=6.5 Hz), 2.95 (2H, t, J=6.5 Hz), 4.13 (2H, q, J=6.5 Hz), 7.25 (2H, d, J=6 Hz), 7.31–7.43 (3H, m), 7.82 (1H, br s), 8.29 (1H, dd, J=4.5 and 6 Hz)

Example 1 (32)

7-(2,6-Dichlorobenzoylamino)-2-methyl-3-methylthiomethylbenzo[b]furan mp: 207°–208.5° C. NMR (CDCl₃, δ): 2.04 (3H, s), 2.44 (3H, s), 3.75 (2H, s), 7.24–7.28 (1H, m), 7.33–7.44 (4H, m), 7.80 (1H, br s), 8.30 (1H, d, J=7.5 Hz)

Example 1 (33)

7-(2,6-Dichlorobenzoylamino)-3-(2-ethoxycarbonylethenyl)-2-inethylbenzo[b]furan mp: 207°–208° C. NMR (CDCl₃, δ): 1.36 (3H, t, J=7.5 Hz), 2.59 (3H, s), 4.28 (2H, q, J=7.5 Hz), 6.52 (1H, d, J=15 Hz), 7.31–7.43 (4H, m), 7.58 (1H, d, J=8 Hz), 7.75 (1H, d, J=15 Hz), 7.83 (1H, br s), 8.37 (1H, d, J=8 Hz)

Example 1 (34)

7-(2,6-Dichlorobenzoylamino)-3-(1-hydroxy-2,2,2-trifluoro-1-trifluoromethylethyl)-2-methylbenzo[b]furan mp: 208°–209° C. NMR (CDCl₃, δ): 2.65 (3H, s), 3.57 (1H, s), 7.25–7.45 (4H, m), 7.50 (1H, m), 7.80 (1H, br s), 8.33 (1H, d, J=7.5 Hz) FABB-Mass: (e/z)=486 (M⁺+1)

Example 1 (35)

3-Butyryl-7-(2,6-dichlorobenzoylamino)-2-methylbenzo[b]furan mp: 187°–188.5° C. NMR (CDCl₃, δ): 1.06 (3H, t, J=7 Hz), 1.81 (2H, sex, J=7 Hz), 2.78 (3H, s), 2.93 (2H, t, J=7 Hz), 7.32–7.45 (4H, m), 7.69 (1H, d, J=8 Hz), 7.82 (1H, br s), 8.35 (1H, d, J=8 Hz)

Example 1 (36)

3-Benzoyl-7-(2,6-dichlorobenzoylamino)-2-methylbenzo[b]furan mp: 213°–215° C. NMR (CDCl₃, δ): 2.57 (3H, s), 7.15 (1H, d, J=8 Hz), 7.25 (1H, t, J=8 Hz), 7.30–7.45 (3H, m)), 7.50 (2H, t, J=8 Hz), 7.61 (1H, t, J=8 Hz), 7.80–7.90 (3H, m), 8.31 (1H, d, J=8 Hz)

Example 1 (37)

7-(2,6-Dichlorobenzoylamino)-3-(1-ethoxycarbonyl)hydroxymethyl-2-methylbenzo[b]furan mp: 169°–171° C. NMR (CDCl₃, δ): 1.22 (3H, t, J=8 Hz), 2.50 (3H, s), 3.41 (1H, d, J=4 Hz), 4.23 (2H, m), 5.30 (1H, d, J=4 Hz), 7.20–7.45 (5H, m), 7.80 (1H, s), 8.28 (1H, d, J=8 Hz)

Example 1 (38)

3-Cyclohexylcarbonyl-7-(2,6-dichlorobenzoylamino)-2-methylbenzo[b]furan mp: 210°–211° C. NMR (CDCl₃, δ): 1.20–1.60 (5H, m), 1.60–2.05 (5H, m), 2.78 (3H, s), 3.09 (1H, m), 7.30–7.50 (4H, m), 7.60 (1H, d, J=8 Hz), 7.85 (1H, br s), 8.36 (1H, d, J=8 Hz)

Example 1 (39)

7-(2,6-Dichlorobenzoylamino)-2,3-dihydro-2-methylbenzo[b]furan mp: 119°–120° C. NMR (CDCl₃, δ): 1.47 (3H, d, J=7 Hz), 2.88 (1H, dd, J=8 and 15 Hz), 3.66 (1H, dd, J=8 and 15 Hz), 4.99 (1H, m), 6.90 (1H, t, J=8 Hz), 6.97 (1H, d, J=8 Hz), 7.25–7.40 (3H, m), 7.48 (1H, br s), 8.25 (1H, d, J=8 Hz)

Example 1 (40) 7-(2-Chloro-6-fluorobenzoylamino)-2,3-dimethylbenzo[b]furan mp: 161°–162° C. NMR (CDCl₃, δ): 2.15 (3H, s), 2.37 (3H, s), 7.12 (1H, t, J=8 Hz), 7.20–7.30 (3H, m), 7.39 (1H, m), 7.88 (1H, br s), 8.27 (1H, m)

Example 1 (41)

3-Acetyl-7-(2-bromo-6-methylbenzoylamino)-2-methylbenzo[b]furan mp: 198° C. NMR (CDCl₃, δ): 2.49 (3H, s), 2.67 (3H, s), 2.78 (3H, s), 7.2–7.3 (2H, m), 7.38 (1H, t, J=7.5 Hz), 7.48 (1H, dd, J=2 and 7.5 Hz), 7.71 (1H, d, J=7.5 Hz), 7.77 (1H, br s), 8.35 (1H, d, J=7.5 Hz)

Example 1 (42)

7-(2-Chloro-6-methoxybenzoylamino)-3-(1-hydroxy-1-methylethyl)-2-methylbenzo[b]furan mp: 148.5°–150° C. NMR (CDCl₃, δ): 1.70 (6H, s), 1.78 (1H, s), 2.57 (3H, s), 3.84 (3H, s), 6.90 (1H, d, J=8 Hz), 7.06 (1H, d, J=8 Hz), 7.20 (1H, t, J=8 Hz), 7.32 (1H, t, J=8 Hz), 7.42 (1H, d, J=8 Hz), 7.87 (1H, br s), 8.32 (1H, d, J=8 Hz)

Example 1 (43)

3-(1-Hydroxy-1-methyiethyl)-2-methyl-7-(6-methyl-2-nitrobenzoylamino)benzo[b]furan mp: 180°–182.5° C. NMR (CDCl₃, δ): 1.71 (6H, s), 1.80 (1H, s), 2.56 (6H, s), 7.23 (1H, t, J=8 Hz), 7.48 (1H, d, J=8 Hz), 7.52 (1H, t, J=8 Hz), 7.61 (1H, d, J=8 Hz), 7.74 (1H, br s), 8.09 (1H, d, J=8 Hz), 8.22 (1H, d, J=8 Hz)

Example 1 (44)

7-(2-Chloro-6-phenylbenzoylamino)-2,3-dimethylbenzo[b]furan mp: 118°–120° C. NMR (CDCl₃, δ): 2.09 (3H, s), 2.29 (3H, s), 7.10–7.14 (2H, m), 7.22–7.40 (4H, m), 7.40–7.47 (2H, m), 7.47–7.55 (3H, m), 7.99 (1H, m)

Example 1 (45)

3-Acetyl-7-(2,6-dichloro-3-nitrobenzoylamino)-2-methylbenzo[b]furan mp: >250° C. NMR (DMSO-d₆, δ): 2.62 (3H, m), 2.80 (3H, m), 7.37 (1H, t, J=8 Hz), 7.85 (1H, d, J=8 Hz), 7.89 (1H, d, J=8 Hz), 7.94 (1H, d, J=8 Hz), 8.22 (1H, d, J=8 Hz)

Example 1 (46)

7-(2,6-Dichloro-3-nitrobenzoylamino)-2,3-dimethylbenzo[b]furan mp: 225°–226° C. NMR (CDCl₃, δ): 2.17 (3H, s), 2.38 (3H, s), 7.21–7.28 (2H, m), 7.57 (1H, d, J=8 Hz), 7.85 (1H, br s), 7.90 (1H, br s), 8.22 (1H, m)

Example 1 (47)

2,3-Dimethyl-7-(2,4,6-trichlorobenzoylamino)benzo-[b]furan mp: 215°–217° C. NMR (CDCl₃, δ): 2.16 (3H, s), 2.38 (3H, s), 7.20–7.27 (2H, m), 7.41 (2H, s), 7.79 (1H, br s), 8.23 (1H, m)

Example 1 (48)

7-(2,6-Dichloro-3-methylbenzoylamino)-2,3-dimethylbenzo[b]furan mp: 188°–190° C. NMR (CDCl₃, δ): 2.14 (3H, s), 2.35 (3H, s), 2.40 (3H, s), 7.20–7.30 (4H, m), 7.80 (1H, br s), 8.30 (1H, d, J=8 Hz)

Example 1 (49)

7-(2,6-Dichloro-3-triisopropylsilyloxybenzoyl-amino)-2,3-dimethylbenzo[b]furan NMR (CDCl₃, δ): 1.12 (18H, d, J=7 Hz), 1.26–1.39 (3H, m), 2.14 (3H, s), 2.37 (3H, s), 6.90 (1H, d, J=8 Hz), 7.19–7.27 (3H, m), 7.77 (1H, br s), 8.29 (1H, d, J=8 Hz)

Example 1 (50)

2,3-Dimetyl-7-(2,4,6-triisopropylbenzoylamino)-benzo[b]furan mp: 136°–137° C. NMR (CDCl₃, δ): 1.28 (18H, d, J=7.5 Hz), 2.14 (3H, s), 2.33 (3H, s), 2.94 (1H, m), 3.14 (2H, m), 7.10 (2H, s), 7.20 (1H, t, J=7.5 Hz), 7.23 (1H, d, J=7.5 Hz), 7.84 (1H, br s), 8.31 (1H, d, J=7.5 Hz)

Example 1 (51)

7-(2,6-Dichloro-3-dimethylaminomethylbenzoyl-amino)-2,3-dimethylbenzo[b]furan hydrochloride mp: >250° C. NMR (CDCl₃:CD₃OD=9:1, δ): 2.15 (3H, s), 2.38 (9H, s), 4.42 (2H, s), 7.23 (2H, m), 7.54 (1H, d, J=8 Hz), 8.03 (1H, d, J=8 Hz), 8.12 (1H, m)

Example 1 (52)

2,3-Dimethyl-7-(2,4,6-trimethylbenzoylamino)-benzo[b]furan mp: 151°–152° C. NMR (CDCl₃, δ): 2.15 (3H, s), 2.33 (3H, s), 2.34 (3H, s), 2.39 (6H, s), 6.93 (2H, s), 7.1–7.3 (2H, m), 7.75 (1H, br s), 8.29 (1H, d, J=7.5 Hz)

Example 1 (53)

7-[2,6-Dichloro-3-(2-methoxyethyl)oxymethoxymeethylbenzoylamino]-2,3-dimethylbenzo[b]furan NMR (CDCl₃, δ): 2.15 (3H, s), 2.37 (3H, s), 3.40 (3H, s), 3.55–3.60 (2H, m), 3.72–3.78 (2H, m), 4.72 (2H, s), 4.87 (2H, s), 7.20–7.28 (2H, m), 7.40 (1H, d, J=8 Hz), 7.54 (1H, d, J=8 Hz), 7.89 (1H, br s), 8.29 (1H, d, J=8 Hz)

Example 1 (54)

2,3-Dimethyl-7-(2-iodobenzoylamino)benzo[b]furan mp: 171°–172.5° C. NMR (CDCl₃, δ): 2.16 (3H, s), 2.37 (3H, s), 7.13–7.27 (3H, m), 7.46 (1H, t, J=8 Hz), 7.59 (1H, d, J=8 Hz), 7.89 (1H, br s), 7.95 (1H, d, J=8 Hz), 8.25 (1H, d, J=8 Hz) FAB-Mass: (m/z)=392 (M⁺+1)

Example 1 (55)

7-(2-Cyclohexylbenzoylamino)-2,3-dimethylbenzo[b]furan mp: 137°–138° C. NMR (CDCl₃, δ): 1.2–1.6 (5H, m), 1.65–1.85 (3H, m), 1.90–2.00 (2H, m), 2.15 (3H, s), 2.35 (3H, s), 3.07 (1H, m), 7.1–7.4 (3H, m), 7.4–7.5 (2H, m), 7.53 (1H, d, J=7.5 Hz), 7.87 (1H, br s), 8.25 (1H, d, J=7.5 Hz)

Example 1 (56)

2,3-Dimethyl-7-(2,3,5,6-tetramethylbenzoylamino)-benzo[b]furan mp: 195° C. NMR (CDCl₃, δ): 2.15 (3H, s), 2.26 (6H, s), 2.29 (6H, s), 2.39 (3H, s), 7.04 (1H, s), 7.1–7.3 (2H, m), 7.78 (1H, br s), 8.33 (1H, d, J=7.5 Hz)

Example 1 (57)

2,3-Dimethyl-7-(2-methoxy-1-naphthoylamino)-benzo[b]furan mp: 165°–167° C. NMR (CDCl₃, δ): 2.15 (3H, s), 2.32 (3H, s), 4.01 (3H, s), 7.20 (1H, d, J=8 Hz), 7.28 (1H, t, J=8 Hz), 7.33 (2H, d, J=8 Hz), 7.40 (1H, t, J=8 Hz), 7.82 (1H, d, J=8 Hz), 7.96 (1H, d, J=8 Hz), 8.12 (1H, d, J=8 Hz), 8.24 (1H, br s), 8.43 (1H, d, J=8 Hz)

Example 1 (58)

7-(3,5-Dichloroisonicotinoylamino)-3-(1-hydroxy-1-methylethyl)-2-methylbenzo[b]lfuran mp: 170°–171.5° C. NMR (CDCl₃, δ): 1.72 (6H, s), 1.85 (1H, s), 2.60 (3H, s), 7.23 (1H, t, J=8 Hz), 7.52 (1H, d, J=8 Hz), 7.86 (1H, br s), 8.21 (1H, d, J=8 Hz), 8.62 (2H, s)

Example 1 (59)

4-(2,6-Dichlorobenzoylamino)-2,3-dimethylbenzo-[b]furan mp: 252°–253° C. NMR (DMSO-d₆, δ): 2.31 (3H, s), 2.37 (3H, s), 7.18–7.30 (2H, m), 7.38 (1H, d, J=7 Hz), 7.52 (1H, dd, J=7 and 8 Hz), 7.55–7.66 (2H, m)

Example 1 (60)

6-(2,6-Dichlorobenzoylamino)-2,3-dimethylbenzo-[b]furan mp: 175°–176° C. NMR (CDCl₃, δ): 2.15 (3H, s), 2.38 (3H, s), 7.20–7.40 (5H, m), 7.48 (1H, s), 7.90 (1H, s)

Example 1 (61)

5-(2,6-Dichlorobenzoyla.mino)-2,3-dimethylbenzo-[b]furan mp: 229°–230° C. NMR (CDCl₃, δ): 2.17 (3H, s), 2.39 (3H, s), 7.10–7.50 (6H, m), 7.89 (1H, s)

Example 1 (62)

3-(2-Acetylaminothiazol-4-yl)-7-(2,6-dichlorobenzoylamino)-2-methylbenzo[b]furan mp: >250° C. NMR (CDCl₃:CD₃OD=1:1, δ): 2.28 (3H, s), 2.68 (3H, s), 7.05 (1H, s), 7.30 (1H, t, J=7 Hz), 7.35–7.50 (3H, m), 7.62 (1H, d, J=7 Hz), 8.16 (1H, d, J=7 Hz)

Example 1 (63)

6-Acetyl-1-(2,6-dichlorobenzoylamino)-6,7,8,9-tetrahydro-5H-10-oxo-6-aza-benzo[b]azulene mp: 252°–255° C. NMR (CDCl₃, δ): 2.00–2.17 (5H, m), 2.97–3.08 (2H, m), 3.72–3.88 (2H m), 4.56 (4/3H, s), 4.77 (2/3H, s), 7.20–7.43 (5H, m), 7.76–7.84 (1H, m), 8.25–8.35 (1H, m)

Example 1 (64)

7-(2-Chloronicotinoylamino)-3-(1-hydroxy-1-methylethyl)-2-methylbenzo[b]furan mp: 92°–94° C. NMR (CDCl₃, δ): 1.71 (6H, s), 1.86 (1H, 5), 2.60 (3H, s), 7.25 (1H, t, J=8 Hz), 7.43 (1H, m), 7.50 (1H, d, J=8 Hz), 8.20 (1H, d, J=8 Hz), 8.29 (1H, d, J=8 Hz), 8.54 (1H, m), 8.70 (1H, br s)

Example 1 (65)

7-(3,5-Dimethyl-2-oxo-2H-pyran-4-yl)carbonylamino-3-(1-hydroxy-1-methylethyl)-2-methylbenzo[b]furan NMR (CDCl₃, δ): 1.72 (6H, s), 1.87 (1H, s), 2.26 (3H, s), 2.42 (3H, s), 2.60 (3H, s), 6.08 (1H, s), 7.21 (1H, t, J=8 Hz), 7.51 (1H, d, J=8 Hz), 7.86 (1H, br s), 8.08 (1H, m)

Example 1 (66)

3-(1-Hydroxy-1-methylethyl)-2-methyl-7-(2-trifluoromethylbenzoylamino)benzo[b]furan mp: 165°–166° C. NMR (CDCl₃, δ): 1.17 (6H, s), 1.80 (1H, s), 2.57 (3H, s), 7.21 (1H, t, J=8 Hz), 7.47 (1H, d, J=8 Hz), 7.60–7.82 (4H, m), 7.90 (1H, br s), 8.22 (1H, d, J=8 Hz)

Example 1 (67)

7-(2-Benzoylbenzoylamino)-2,3-dimethylbenzo[b]furan mp: 219°–221.5° C. NMR (CDCl₃, δ): 2.10 (3H, s), 2.35 (3H, s), 5.38 (1H, br s), 6.26 (1H, d, J=8 Hz), 6.79 (1H, t, J=8 Hz), 6.88 (1H, d, J=8 Hz), 7.30–7.41 (3H, m), 7.55 (1H, m), 7.61–7.68 (2H, m), 7.74 (2H, d, J=8 Hz), 7.91 (1H, d, J=8 Hz)

Example 1 (68)

2,3-Dimethyl-7-(3,5-dimethylisoxazol-4-yl)-carbonylaminobenzo[b]furan NMR (CDCl₃, δ): 2.16 (3H, s), 2.40 (3H, s), 2.59 (3H, s), 2.73 (3H, s), 7.18–7.21 (2H, m), 7.77 (1H, br s), 8.09 (1H, m)

Example 1 (69)

7-(3-Chlorobenzo[b]thiophen-2-yl)carbonylamino-3-(1-hydroxy-1-methylethyl)-2-methylbenzo[b]furan mp: 191°–193° C. NMR (CDCl₃, δ): 1.74 (6H, s), 1.86 (1H, s), 2.65 (3H, s), 7.22 (1H, t, J=8 Hz), 7.48 (1H, d, J=8 Hz), 7.55 (2H, m), 7.89 (1H, dd, J=1.5 and 8 Hz), 7.95 (1H, dd, J=1.5 and 8 Hz), 8.24 (1H, d, J=8 Hz), 9.50 (1H, br s)

Example 1 (70)

7-(3-Bromo-1-methylindol-2-yl)carbonylamino-3-(1-hydroxy-1-methylethyl)-2-methylbenzo[b]furan mp: 154°–155° C. NMR (CDCl₃, δ): 1.73 (6H, s), 1.81 (1H, s), 2.62 (3H, s), 4.11 (3H, s), 7.19–7.30 (2H, m), 7.42 (2H, d, J=5 Hz), 7.48 (1H, d, J=8 Hz), 7.68 (1H, d, J=8 Hz), 8.22 (1H, d, J=8 Hz), 9.03 (1H, br s)

Example 1 (71)

7-(6-Benzyloxy-2-chlorobenzoylamino)-3-(1-hydroxy-1-methylethyl)-2-methylbenzo[b]furan mp: 161°–162° C. NMR (CDCl₃, δ): 1.71 (6H, s), 1.82 (1H, s), 2.52 (3H, s), 5.18 (2H, s), 6.91 (1H, d, J=8 Hz), 7.07 (1H, d, J=8 Hz), 7.19–7.31 (5H, m), 7.33–7.40 (2H, m), 7.43 (1H, d, J=8 Hz), 7.90 (1H, br s), 8.30 (1H, d, J=8 Hz)

Example 1 (72)

7-(2-Chloro-6-phenoxybenzoylamino)-3-(1-hydroxy-1-methylethyl)-2-methylbenzo[b]furan mp: 161°–162° C. NMR (CDCl₃, δ): 1.70 (6H, s), 1.79 (1H, s), 2.54 (3H, s), 6.82 (1H, d, J=8 Hz), 7.06 (2H, d, J=8 Hz), 7.10–7.23 (3H, m), 7.23–7.38 (3H, m), 7.41 (1H, d, J=8 Hz), 7.98 (1H, br s), 8.23 (1H, d, J=8 Hz)

Example 1 (73)

7-(2,6-Dichlorobenzoylamino)-3-ethoxycarbonylmethyl-2-methylbenzo[b]furan mp: 175°–177° C. NMR (CDCl₃, δ): 1.26 (3H, t, J=7 Hz), 2.43 (3H, s), 3.60 (2H, s), 4.16 (2H, q, J=7 Hz), 7.23–7.30 (2H, m), 7.30–7.43 (3H, m), 7.80 (1H, br s), 8.30 (1H, d, J=8 Hz)

Example 1 (74)

3-Bromo-7-(2,6-dichlorobenzoylamino)-2-(2-ethoxycarbonylethyl)benzo[b]furan mp: 168°–170° C. NMR (CDCl₃, δ): 1.23 (3H, t, J=7 Hz), 2.75 (2H, t, J=7 Hz), 3.17 (2H, t, J=7 Hz), 4.13 (2H, q, J=7 Hz), 7.25–7.43 (5H, m), 7.77 (1H, m), 8.34 (1H, d, J=8 Hz)

Example 1 (75)

7-(2,6-Dichlorobenzenesulfonylamino)-3-(1-hydroxy-1-methylethyl)-2-methylbenzo[b]furan mp: 166°–168° C. NMR (CDCl₃, δ): 1.67 (6H, s), 1.73 (1H, s), 2.51 (3H, s), 7.08 (1H, t, J=8 Hz), 7.25 (1H, m), 7.30 (1H, t, J=8 Hz), 7.40 (1H, d, J=8 Hz), 7.73 (1H, br s)

Example 1 (76)

7-(2,6-Dichlorobenzoyloxy)-2,3-dimethylbenzo[b]furan mp: 129°–130° C. NMR (CDCl₃, δ): 2.16 (3H, s), 2.39 (3H, s), 7.10–7.25 (2H, m), 7.30–7.45 (4H, m)

Example 2 (1)

A mixture of 7-carboxy-2,3-dimethylbenzo[b]furan (190 mg) and a catalytic amount of dimethylformamide in thionylchloride (10 ml) was refluxed for 3 hours. After evaporation in vacuo with toluene, it was added to a mixture of 2,6-dichloroaniline (162 mg) and triethylamine (202 mg) in 1,2-dichloroethane (3 ml) at ambient temperature. The mixture was stirred at 60° C. for 3 hours and washed with water and brine. After drying over sodium sulfate, it was evaporated in vacuo. The residue was purified by column chromatography on silica gel eluting with ($CH_2Cl_2$:n-hexane= 2:1) and the obtained oil was crystallized from ethanol to give 7-[N-(2,6-dichlorophenyl)carbamoyl]-2,3-dimethylbenzo[b]furan (124 mg).

mp: 188°–190° C. NMR ($CDCl_3$, δ): 2.22 (3H, s), 2.49 (3H, s), 7.23 (1H, t, J=8 Hz), 7.36 (1H, t, J=8 Hz), 7.45 (1H, d, J=8 Hz), 7.62 (1H, d, J=8 Hz), 8.12 (1H, d, J=8 Hz), 9.11 (1H, br s)

The following compounds [Examples 2 (2) to (12)] were obtained according to a similar manner to that of Example 2 (1).

Example 2 (2)

6-[N-(2,6-Dichlorophenyl)carbamoyl]-1,2,3,4-tetrahydrodibenzofuran mp: 129° C. NMR ($CDCl_3$, δ): 1.80 (2H, m), 2.01 (2H, m), 2.68 (2H, m), 2.83 (2H, m), 7.23 (1H, t, J=7.5 Hz), 7.36 (1H, t, J=7.5 Hz), 7.44 (2H, d, J=7.5 Hz), 7.62 (1H, d, J=7.5 Hz), 8.12 (1H, d, J=7.5 Hz), 9.13 (1H, br s)

Example 2 (3)

7-[N-(2-Chloro-6-methylphenyl)carbamoyl]-2,3-dimethylbenzo[b]furan mp: 157°–158° C. NMR ($CDCl_3$, δ): 2.22 (3H, s), 2.39 (3H, s), 2.49 (3H, s), 7.18 (1H, t, J=7.5 Hz), 7.23 (1H, d, J=7.5 Hz), 7.35 (1H, d, J=7.5 Hz), 7.36 (1H, t, J=7.5 Hz), 7.62 (1H, d, J=7.5 Hz), 8.11 (1H, d, J=7.5 Hz), 9.02 (1H, br s)

Example 2 (4)

7-[N-(2,6-Diisopropylphenyl)carbamoyl]-2,3-dimethylbenzo[b]furan mp: 158°–159° C. NMR ($CDCl_3$, δ): 1.23 (12H, d, J=7.5 Hz), 2.23 (3H, s), 2.45 (3H, s), 3.23 (2H, m), 7.25 (2H, d, J=7.5 Hz), 7.35 (1H, t, J=7.5 Hz), 7.36 (1H, t, J=7.5 Hz), 7.62 (1H, d, J=7.5 Hz), 8.12 (1H, d, J=7.5 Hz), 8.73 (1H, br s)

Example 2 (5)

2,3-Dimethyl-7-[N-(6-methyl-2-nitrophenyl)-carbamoyl]benzo[b]furan mp: 159°–160° C. NMR ($CDCl_3$, δ): 2.23 (3H, s), 2.45 (3H, s), 2.54 (3H, s), 7.30–7.40 (2H, m), 7.58 (1H, d, J=7.5 Hz), 7.63 (1H, d, J=7.5 Hz), 7.87 (1H, d, J=7.5 Hz), 8.06 (1H, d, J=7.5 Hz), 10.28 (1H, br s)

Example 2 (6)

7-[N-(2,6-Dibromophenyl)carbamoyl]-2,3-dimethylbenzo[b]furan mp: 209°–210° C. NMR ($CDCl_3$, δ): 2.22 (3H, s), 2.49 (3H, s), 7.09 (1H, t, J=7.5 Hz), 7.37 (1H, t, J=7.5 Hz), 7.63 (1H, d, J=7.5 Hz), 7.67 (2H, d, J=7.5 Hz), 8.13 (1H, d, J=7.5 Hz), 9.15 (1H, br s)

Example 2 (7)

2,3-Dimethyl-7-[N-(2-methoxy-6-methylphenyl) carbamoyl]benzo[b]furan mp: 143°–144° C. NMR ($CDCl_3$, δ): 2.20 (3H, s), 2.35 (3H, s), 2.46 (3H, s), 3.83 (3H, s), 6.82 (1H, d, J=7.5 Hz), 6.92 (1H, d, J=7.5 Hz), 7.19 (1H, t, J=7.5 Hz), 7.34 (1H, t, J=7.5 Hz), 7.58 (1H, d, J=7.5 Hz), 8.09 (1H, d, J=7.5 Hz), 8.87 (1H, br s)

Example 2 (8)

7-[N-(6-Chloro-2-methoxycarbonyl)carbamoyl]-2,3-dimethylbenzo[b]furan mp: 132°–133° C. NMR ($CDCl_3$, δ): 2.22 (3H, s), 2.51 (3H, s), 3.85 (3H, s), 7.25 (1H, t, J=7.5 Hz), 7.34 (1H, t, J=7.5 Hz), 7.62 (1H, d, J=7.5 Hz), 7.65 (1H, d, J=7.5 Hz), 7.81 (1H, d, J=7.5 Hz), 8.08 (1H, d, J=7.5 Hz)

Example 2 (9)

7-[N-(2,4,6-Trichlorophenyl)carbamoyl]-2,3-dimethylbenzo[b]furan mp: 189°–190° C. NMR ($CDCl_3$, δ): 2.20 (3H, s), 2.48 (3H, s), 7.36 (1H, t, J=7.5 Hz), 7.47 (2H, s), 7.13 (1H, d, J=7.5 Hz), 8.10 (1H, d, J=7.5 Hz), 9.03 (1H, br s)

Example 2 (10)

7-[N-(2,6-Dichloro-3-methylphenyl)carbamoyl]-2,3-dimethylbenzo[b]furan mp: 216°–217° C. NMR ($CDCl_3$, δ): 2.19 (3H, s), 2.40 (3H, s), 2.45 (3H, s), 7.35 (1H, t, J=7.5 Hz), 7.40 (1H, d, J=7.5 Hz), 7.50 (1H, d, J=7.5 Hz), 7.72 (1H, d, J=7.5 Hz), 7.73 (1H, d, J=7.5 Hz)

Example 2 (11)

2,3-Dimethyl-7-[N-(2,4,6-trimethylphenyl)-carbamoyl]benzo[b]furan mp: 149° C. NMR ($CDCl_3$, δ): 2.21 (3H, s), 2.30 (6H, s), 2.32 (3H, s), 2.45 (3H, s), 6.98 (2H, s), 7.35 (1H, t, J=7.5 Hz), 7.60 (1H, d, J=7.5 Hz), 8.10 (1H, d, J=7.5 Hz), 8.74 (1H, br s)

Example 2 (12)

2,3-Dimethyl-7-(N-methoxy-N-methyl)carbamoylbenzo[b]furan NMR ($CDCl_3$, δ): 2.15 (3H, s), 2.40 (3H, s), 3.37 (3H, s), 3.63 (3H, s), 7.21 (1H, t, J=8 Hz), 7.34 (1H, d, J=8 Hz), 7.47 (1H, d, J=8 Hz)

Example 3

Lithium aluminium hydride (38 mg) was added to a solution of 2,3-dimethyl 7-(N-methoxy-N-methyl) carbamoylbenzo[b]furan (189 mg) in diethyl ether at 4° C. The mixture was stirred at 4° C. for 10 minutes, quenched with aqueous 10% tartaric acid and partitioned between diethyl ether and water. The organic layer was separated, washed with water, dried over sodium sulfate and evaporated in vacuo. The residue was dissolved in tetrahydrofuran (5 ml) and added dropwise at 4° C. to a mixture at (2,6-dichlorobenzyl)triphenylphosphonium bromide (407 mg) and potassium tert-butoxide (100 mg) in tetrahydrofuran (5 ml) which was previously stirred at ambient temperature for 30 minutes. The mixture was stirred at ambient temperature for 30 minutes and partitioned between diethyl ether and aqueous saturated sodium bicarbonate. The organic layer was separated, washed with water, dried over sodium sulfate and evaporated in vacuo. The residue was purified by column chromatography on silica gel and the obtained oil was crystallized from a mixture of ethyl acetate and n-hexane to give 7-[2-(2,6-dichlorophenyl)ethenyl]-2,3-dimethylbenzo[b]furan.

mp: 93°–94° C. NMR ($CDCl_3$, δ): 2.18 (3H, s), 2.44 (3H, s), 7.11 (1H, t, J=7.5 Hz), 7.21 (1H, t, J=7.5 Hz), 7.30–7.40 (4H, m), 7.40 (1H, d, J=16 Hz), 7.63 (1H, d, J=16 Hz)

Example 4 (1)

A mixture of 7-amino-2,3-dimethylbenzo[b]furan (100 mg) and 6-chloro-N-methylisatoic anhydride (147 mg) in acetic acid (2 ml) was stirred at 60° C. for 2 hours. The reaction mixture was concentrated in vacuo and the residue was crystallized from a mixture of ethanol and water to give 2,3-dimethyl-7-(2-chloro-6-methylaminobenzoylamino) benzo[b]furan (210 mg)

mp: 175°–178° C. NMR (CDCl$_3$, δ): 2.14 (3H, s), 2.37 (3H, s), 2.83 (3H, d, J=6 Hz), 5.62 (1H, m), 6.59 (1H, d, J=8 Hz), 6.73 (1H d, J=8 Hz), 7.19 (3H, m), 8.16–8.22 (2H, m)

The following compound was obtained according to a similar manner to that of Example 4 (1).

Example 4 (2)

3-Acetyl-7-(6-amino-2-chlorobenzoylamino)-2-methylbenzo[b]furan mp: 174°–175° C. NMR (CDCl$_3$, δ): 2.66 (3H, s), 2.80 (3H, s), 4.60–4.97 (2H, m), 6.67 (1H, d, J=7.5 Hz), 6.83 (1H, d, J=7.5 Hz), 7.15 (1H, t, J=7.5 Hz), 7.37 (1H, t, J=7.5 Hz), 7.71 (1H, d, J=7.5 Hz), 8.25 (1H, br s), 8.30 (1H, d, J=7.5 Hz)

Example 5 (1)

A mixture of 7-amino-2,3-dimethylbenzo[b]furan (161 mg), triethylamine (202 mg) and 3,6-dichlorophthalic anhydride (261 mg) in dichloromethane (5 ml) was stirred at ambient temperature for 1 hour. The reaction mixture was washed with 1N-hydrochloric acid and brine, dried over sodium sulfate and concentrated in vacuo. The residue was dissolved in methanol and treated with diazomethane. The separated solid was collected and washed with methanol to give 7-(3,6-dichlorophthalimido)-2,3-dimethylbenzo[b]furan (250 mg).

mp: 211°–212° C. NMR (CDCl$_3$, δ): 2.18 (3H, s), 2.35 (3H, s), 7.14 (1H, d, J=8 Hz), 7.30 (1H, t, J=8 Hz), 7.49 (1H, d, J=8 Hz), 7.65 (2H, s) FAB-Mass: (m/z)=360 (M$^+$+1)

The following compound was obtained according to a similar manner to that of Example 5 (1).

Example 5 (2)

3-(1-Hydroxy-1-methylethyl)-2-methyl-7-(3-nitrophthalimido)benzo[b]furan mp: 133°–136° C. NMR (CDCl$_3$, δ): 1.72 (6H, s), 1.81 (1H, s), 2.52 (3H, s), 7.17 (1H, d, J=8 Hz), 7.30 (1H, t, J=8 Hz), 7.82 (1H, d, J=8 Hz), 8.00 (1H, t, J=8 Hz), 8.20 (1H, d, J=8 Hz), 8.26 (1H, d, J=8 Hz)

Example 6

A solution of 7-(3,6-dichlorophthalimido)-2,3-dimethylbenzo[b]furan (100 mg) in 2N-amnonia in methanol was stirred at ambient temperature for 3 hours. The separated solid was washed with water and dried to give 7-(2,5-dichloro-6-carbamoylbenzoylamino)-2,3-dimethylbenzo[b]furan (63 mg).

mp: 229°–232° C.; NMR (DMSO-d$_6$, δ): 2.14 (3H, s), 2.29 (3H, s), 7.18 (1H, t, J=8 Hz), 7.27 (1H, d, J=8 Hz), 7.61 (2H, s), 7.75–7.85 (3H, m)

Example 7

A solution of 7-(3,6-dichlorophthalimido)-2,3-dimethylbenzo[b]furan (100 mg) in a mixture of aqueous 1N-sodium hydroxide (2 ml) and methanol (3 ml) was stirred at ambient temperature overnight. The reaction mixture was acidified with 1N-hydrochloric acid. The separated solid was collected, washed with water and dried to give 7-(6-carboxy-2,5-dichlorobenzoylamino)-2,3-dimethylbenzo[b]furan (60 mg).

mp: 186°–188° C.; NMR (DMSO-d$_6$, δ): 2.14 (3H, s), 2.39 (3H, s), 7.19 (1H, t, J=8 Hz), 7.28 (1H, d, J=8 Hz), 7.66 (2H, s), 7.73 (1H, d, J=8 Hz)

Example 8

A mixture of 7-amino-3-(1-hydroxy-l-methylethyl)-2-methylbenzo[b]furan (150 mg), 3-nitrophthalic anhydride (205 mg) and potassium carbonate (202 mg) in N,N-dimethylformamide (2 ml) was stirred at ambient temperature for 2 hours. Then, isopropyl iodide (280 mg) was added to the mixture and the mixture was stirred for 3 hours. The mixture was partitioned between ethyl acetate and brine. The organic layer was separated, dried over sodium sulfate and evaporated in vacuo. The residue was purified by column chromatography on silica gel and the obtained oil was crystallized from a mixture of 2-propanol and water to give 3-(1-hydroxy-1-methylethyl)-7-(6-isopropoxycarbonyl-2-nitrobenzoylamino)-2-methylbenzo[b]furan (136 mg).

mp: 118°–120° C.; NMR (CDCl$_3$, δ): 1.19 (6H, d, J=7 Hz), 1.71 (6H, s), 1.82 (1H, s), 2.54 (3H, s), 5.20 (1H, m), 7.21 (1H, d, J=8 Hz), 7.44 (1H, d, J=8 Hz), 7.72 (1H, t, J=8 Hz), 7.83 (1H, br s), 8.28 (1H, d, J=8 Hz), 8.36 (2H, dd, J=1.5 and 8 Hz)

Example 9

A mixture of 3-(1-hydroxy-1-methylethyl)-2-methyl-7-(3-nitrophthalimido)benzo[b]furan (80 mg) and sodium borohydride (16 mg) in ethanol (2 ml) was stirred at ambient temperature for 3 hours. The mixture was poured into water and extracted with ethyl acetate. The extract was washed with brine, dried over sodium sulfate and evaporated in vacuo. The residue was purified by column chromatography on silica gel and the obtained oil was crystallized from diisopropyl ether to give 3-(1-hydroxy-1-methylethyl)-7-(3-hydroxy-4-nitrophthalimidin-2-yl)-2-methylbenzo[b]furan (39 mg).

mp: 156°–158° C.; NMR (CDCl$_3$, δ): 1.72 (6H, s), 1.84 (1H, s), 2.59 (3H, s), 3.77 (1H, d, J=5 Hz), 7.24–7.33 (2H, m), 7.53 (1H, d, J=8 Hz), 7.71 (1H, d, J=8 Hz), 7.81 (1H, d, J=8 Hz), 8.29 (1H, d, J=8 Hz), 8.44 (1H, d, J=8 Hz)

Example 10 (1)

Methanesulfonyl chloride (0.073 ml) was added to a solution of 2,3-dimethyl-7-hydroxymethylbenzo[b]furan (150 mg) and triethylamine (0.166 ml) in dichloromethane at 4° C. The mixture was stirred at 4° C. for 35 minutes. The mixture was washed with aqueous saturated sodium bicarbonate and brine, dried over sodium sulfate and evaporated in vacuo. The residue was dissolved in N,N-dimethylformamide and to the solution was added potassium carbonate (248 mg) and 2,6-dichlorophenol (97 mg). The mixture was stirred at 60° C. for 2 hours and poured into a mixture of ice and water. The separated oil was extracted with ethyl acetate and the extract was washed with brine, dried over sodium sulfate and evaporated in vacuo. The residue was purified by preparative TLC and the obtained oil was crystallized from petroleum ether to give 7-(2,6-dichlorophenoxy)methyl-2,3-dimethylbenzo[b]furan (69 mg).

mp: 87°–88° C.; NMR (CDCl$_3$, δ): 2.15 (3H, s), 2.37 (3H, s), 5.38 (2H, s), 7.00 (1H, t, J=7.5 Hz), 7.22 (1H, t, J=7.5 Hz), 7.30 (2H, d, J=7.5 Hz), 7.40 (1H, d, J=7.5 Hz), 7.46 (1H, d, J=7.5 Hz)

The following compound was obtained according to a similar manner to that of Example 10 (1).

Example 10 (2)

7-(2,6-Dichlorobenzyloxy)-2,3-dimethylbenzo[b]furan mp: 108°–110° C.; NMR (CDCl$_3$, δ): 2.13 (3H, s), 2.48 (3H, s), 5.50 (2H, s), 6.90 (1H, d, J=7 Hz), 7.05 (1H, d, J=7 Hz), 7.12 (1H, t, J=7 Hz), 7.22 (1H, t, J=7 Hz), 7.35 (2H, d, J=7 Hz)

Example 11 (1)

A mixture of 6-amino-1,2,3,4-tetrahydrodibenzofuran (230 mg), 2,5-hexanedione (145 mg) and conc. hydrochloric acid (1 drop) in ethanol (3 ml) was refluxed for 1 hour and poured into water. The mixture was neutralized with aqueous saturated sodium bicarbonate and extracted with ethyl acetate. The extract was washed with brine, dried over sodium sulfate and evaporated in vacuo. The residue was purified by column chromatography on silica gel and the obtained oil was crystallized from a mixture of ethanol and water to give 6-(2,5-dimethylpyrol-1-yl)-1,2,3,4-tetrahydrodibenzofuran (235 mg).

mp: 86°–880° C.; NMR (CDCl$_3$, δ): 1.80–1.99 (4H, m), 2.02 (6H, s), 2.62–2.75 (4H, m), 5.98 (2H, s), 7.07 (1H, d, J=8 Hz), 7.27 (1H, t, J=8 Hz), 7.45 (1H, d, J=8 Hz)

The following compound was obtained according to a similar manner to that of Example 11 (1).

Example 11 (2)

6-[2,6-Dichloro-3-(2,5-dimethylpyrrol-1-yl) benzoylamino]-1,2,3,4-tetrahydrodibenzofuran mp: 244°–245° C.; NMR (CDCl$_3$, δ): 1.79–2.00 (4H, m), 2.02 (6H, s), 2.59–2.80 (4H, m), 5.96 (2H, s), 7.25 (2H, d, J=5 Hz), 7.34 (1H, d, J=8 Hz), 7.52 (1H, d, J=8 Hz), 7.89 (1H, br s), 8.28 (1H, m)

Example 12 (1)

To a solution of 3-acetyl-7-(2,6-dichlorobenzoylamino)-2-methylbenzo[b]furan (100 mg) in tetrahydrofuran (3 ml) was added a 1M solution of methylmagnesium bromide in tetrahydrofuran (0.7 ml) dropwise with ice cooling. The solution was stirred at ambient temperature for 2 hours and to the solution was added aqueous saturated ammonium chloride. Then, the mixture was poured into water and the separated oil was extracted with ethyl acetate. The extract was washed with brine, dried over sodium sulfate and evaporated in vacuo. The residue was purified by colimn chromatography on silica gel and the obtained oil was crystallized from a mixture of diisopropyl ether and hexane to give 7-(2,6-dichlorobenzoylamino)-3-(1-hydroxy-1-methylethyl)-2-methylbenzo[b]furan (75 mg).

mp: 129°–131° C.; NMR (CDCl$_3$, δ): 1.72 (6H, s), 1.82 (1H, s), 2.59 (3H, s), 7.22 (1H, d, J=7 Hz), 7.30–7.50 (4H, m), 7.82 (1H, br s), 8.29 (1H, d, J=7 Hz)

The following compounds [Examples 12 (2) to (12)] were obtained according to a similar manner to that of Example 12 (1).

Example 12 (2)

7-(2,6-Dichlorobenzoylamino)-3-(1-ethyl-1-hydroxypropyl)-2-methylbenzo[b]furan mp: 139°–141° C.; NMR (CDCl$_3$, δ): 0.86 (6H, t, J=7 Hz), 1.60 (1H, s), 1.86 (2H, m), 2.08 (2H, m), 2.59 (3H, s), 7.20 (1H, t, J=7 Hz), 7.30–7.45 (4H, m), 7.85 (1H, br s), 8.28 (1H, d, J=7 Hz)

Example 12 (3)

7-(2,6-Dichlorobenzoylamino)-5-fluoro-3-(1-hydroxy-1-methylethyl)-2-methylbenzo[b]furan mp: 159°–161° C.; NMR (CDCl$_3$, δ): 1.70 (6H, s), 1.79 (1H, s), 2.57 (3H, s), 7.18 (1H, d, J=8 Hz), 7.30–7.45 (3H, m), 7.83 (1H, br s), 8.13 (1H, d, J=8 Hz)

Example 12 (4)

7-(2-Chloro-6-methylbenzoylamino)-3-(1-hydroxy-1-methylethyl)-2-methylbenzo[b]furan mp: 161°–162° C.; NMR (CDCl$_3$, δ): 1.72 (6H, s), 1.80 (1H, s), 2.46 (3H, s), 2.58 (3H, s), 7.17–7.26 (2H, m), 7.29–7.31 (2H, m), 7.47 (1H, d, J=8 Hz), 7.80 (1H, br s), 8.29 (1H, d, J=8 Hz)

Example 12 (5)

7-(2,6-Dichlorobenzoylamino)-3-(3-hydroxy-3-methylbutyl)-2-methylbenzo[b]furan mp: 171°–173° C.; NMR (CDCl$_3$, δ): 1.33 (6H, s), 1.78 (2H, m), 2.39 (3H, s), 2.70 (2H, m), 7.20–7.30 (2H, m), 7.30–7.45 (3H, m), 7.83 (1H, br s), 8.29 (1H, d, J=7 Hz)

Example 12 (6)

5-Chloro-7-(2,6-dichlorobenzoylamino)-3-(1-hydroxy-1-methylethyl)-2-methylbenzo[b]furan mp: 181°–184° C.; NMR (CDCl$_3$, δ): 1.69 (6H, s), 1.80 (1H, s), 2.57 (3H, s), 7.30–7.45 (3H, m), 7.48 (1H, s), 7.80 (1H, br s), 8.35 (1H, s)

Example 12 (7)

7-(3-Acetylamino-2,6-dichlorobenzoylamino)-3-(1-hydroxy-1-methylethyl)-2-methylbenzo[b]furan mp: 136°–140° C.; NMR (CDCl$_3$:CD$_3$OD=19:1, δ): 1.70 (6H, s), 2.27 (3H, s), 2.58 (3H, s), 7.22 (1H, t, J=8 Hz), 7.39 (1H, d, J=8 Hz), 7.50 (1H, d, J=8 Hz), 8.11 (2H, d, J=8 Hz)

Example 12 (8)

7-(2,6-Dichloro-3-dimethylaminoacetylamino-benzoylamino)-3-(1-hydroxy-1-methylethyl)-2-methylbenzo[b]furan mp: 201°–203° C.; NMR (CDCl$_3$, δ): 1.72 (6H, s), 1.82 (1H, s), 2.42 (6H, s), 2.59 (3H, s), 3.14 (2H, s), 7.15–7.30 (2H, m), 7.39 (1H, d, J=8 Hz), 7.48 (1H, d, J=8 Hz), 7.86 (1H, s), 8.27 (1H, d, J=8 Hz), 8.50 (1H, d, J=8 Hz)

Example 12 (9)

7-(2-Bromo-6-methylbenzoylamino)-3-(1-hydroxy-1-metethylethyl)-2-methylbenzo[b]furan mp: 173°–175° C.; NMR (CDCl$_3$, δ): 1.71 (6H, s), 2.47 (3H, s), 2.57 (3H, s), 7.1–7.3 (3H, m), 7.4–7.5 (2H, m), 7.77 (1H, br s), 8.27 (1H, d, J=7.5 Hz)

Example 12 (10)

6-(2,6-Dichlorobenzoylamino)-1-hydroxy-1-methyl-1,2,3,4-tetrahydrodibenzofuran mp: 180°–182° C.; NMR (CDCl$_3$, δ): 1.72 (3H, s), 1.83 (1H, s), 1.90–2.00 (3H, m), 2.02–2.10 (1H, m), 2.63–2.83 (2H, m), 7.24–7.32 (2H, m), 7.32–7.43 (2H, m), 7.52 (1H, d, J=8 Hz), 7.83 (1H, br s), 8.31 (1H, d, J=8 Hz)

Example 12 (11)

6-(2,6-Dichlorobenzoylamino)-9-(1-hydroxy-1-methylethyl)-1,2,3,4-tetrahydrodibenzofuran mp: 192°–194° C.; NMR (CDCl$_3$, δ): 1.72 (6H, s), 1.80–2.00 (4H, m), 2.75 (2H, m), 2.98 (2H, m), 7.21 (1H, d, J=7 Hz), 7.30–7.45 (3H, m), 7.90 (1H, br s), 8.21 (1H, d, J=7 Hz)

Example 12 (12) 7-(6-Acetylamino-2-chlorobenzoylamino)-3-(1-hydroxy-1-methylethyl)-2-methylbenzo[b]furan mp: 219°–220° C.; NMR (CDCl$_3$, δ): 1.72 (6H, s), 1.84 (1H, s), 2.17 (3H, s), 2.58 (3H, s), 7.20–7.28 (2H, m), 7.41 (1H, t, J=8 Hz), 7.53 (1H, d, J=8 Hz), 8.13 (1H, d, J=8 Hz), 8.22–8.29 (2H, m), 9.02 (1H, br s)

Example 13 (1)

Sodium borohydride (7 mg) was added to a solution of 7-(2,6-dichlorobenzoylamino)-3-(1-ethoxycarbonyl) hydroxymethyl-2-methylbenzo[b]furan (76 mg) in methanol (3 ml) at 4° C. The mixture was stirred at ambient temperature for 3 hours and poured into cold water. The separated oil was extracted with ethyl acetate and the extract was washed with brine, dried over sodium sulfate and concentrated in vacuo. The residue was purified by colum chromatography on silica gel and the obtained oil was crystallized from diethyl ether to give 7-(2,6-dichlorobenzoylamino)-3-(1,2-dihydroxyethyl)-2-methylbenzo[b]furan (35 mg).

mp: 167°–168° C.; NMR (CDCl$_3$:CD$_3$OD=9:1, δ): 2.47 (3H, s), 3.71 (1H, dd, J=4 and 11 Hz), 3.90 (1H, dd, J=8 and 11 Hz), 4.96 (1H, dd, J=4 and 8 Hz), 7.22 (1H, t, J=8 Hz), 7.30–7.50 (4H, m), 8.15 (1H, d, J=8 Hz)

The following compounds [Examples 13 (2) to (7)] were obtained according to a similar manner to that of Example 13 (1).

Example 13 (2)
7-(2,6-Dichlorobenzoylamino)-3-(1-hydroxyethyl)-2-methylbenzo[b]furan
mp: 209°–211° C.; NMR (CDCl$_3$:CD$_3$OD=9:1, δ): 1.62 (3H, d, J=6 Hz), 2.46 (3H, s), 5.11 (1H, q, J=6 Hz), 7.25 (1H, t, J=7 Hz), 7.30–7.45 (3H, m), 7.52 (1H, d, J=7 Hz), 8.23 (1H, d, J=7 Hz)

Example 13 (3)
7-(2,6-Dichlorobenzoylamino)-3-(1-hydroxybutyl)-2-methylbenzo[b]furan
mp: 165°–166.5° C.; NMR (CDCl$_3$, δ): 0.95 (3H, t, J=7 Hz), 1.20–1.48 (2H, m), 1.80 (1H, d, J=2 Hz), 1.82–2.09 (2H, m), 2.43 (3H, s), 4.89 (1H, m), 7.25 (1H, m), 7.30–7.43 (3H, m), 7.48 (1H, d, J=8 Hz), 7.80 (1H, br s), 8.29 (1H, d, J=8 Hz)

Example 13 (4)
7-(2,6-Dichlorobenzoylamino)-3-(1-hydroxy)phenylmaethyl-2-methylbenzo[b]furan
mp: 90°–100° C.; NMR (CDCl$_3$, δ): 2.24 (1H, d, J=3 Hz), 2.48 (3H, s), 6.08 (1H, d, J=3 Hz), 7.10–7.20 (2H, m), 7.25–7.50 (8H, m), 7.81 (1H, br s), 8.25 (1H, dd, J=2 and 8 Hz)

Example 13 (5)
6-(2,6-Dichlorobenzoylamino)-1,2-dihydro-1-hydroxy-4H-thiopyrano[3,4-b]benzo[b]furan
mp: 214°–216° C.; NMR (CDCl$_3$, δ): 2.44 (1H, d, J=10 Hz), 2.96 (1H, dd, J=4 and 14 Hz), 3.15 (1H, dd, J=4 and 14 Hz), 3.56 (1H, d, J=16 Hz), 3.88 (1H, d, J=16 Hz), 5.09 (1H, td, J=4 and 10 Hz), 7.30–7.45 (4H, m), 7.47 (1H, d, J=8 Hz), 7.78 (1H, br s), 8.32 (1H, d, J=8 Hz)

Example 13 (6)
3-(1-Cyclohexyl)hydroxymethyl-7-(2,6-dichlorobenzoylamino)-2-methvlbenzo[b]furan
mp: 214°–216° C.; NMR (CDCl$_3$, δ): 0.80–2.20 (12H, m), 2.40 (3H, s), 4.54 (1H, d, J=8 Hz), 7.23 (1H, t, J=8 Hz), 7.30 (1H, t, J=8 Hz), 7.30–7.50 (4H, m), 7.80 (1H, br s), 8.28 (1H, d, J=8 Hz)

Example 13 (7)
6-(2,6-Dichlorobenzoylamino)-1-hydroxy-1,2,3,4-tetrahydrodibenzofuran
mp: 163°–165° C.; NMR (CDCl$_3$, δ): 1.70 (1H, d, J=7 Hz), 1.88–1.99 (2H, m), 1.99–2.14 (2H, m), 2.62–2.84 (2H, m), 5.03 (1H, m), 7.23–7.32 (2H, m), 7.32–7.47 (3H, m), 7.82 (1H, br s), 8.30 (1H, d, J=8 Hz)

Example 14 (1)
A mixture of 7-(2,6-dichlorobenzoylamino)-3-hydroxymethyl-2-methylbenzo[b]furan (123 mg), acetic anhydride (43 mg) and pyridine (48 mg) in dichloromethane (5 ml) was refluxed for 2 hours. The reaction mixture was washed with 1N-hydrochloric acid, brine and aqueous saturated sodium bicarbonate, dried over sodium sulfate and evaporated in vacuo. The residue was crystallized from diethyl ether to give 3-acetoxymethyl-7-(2,6-dichlorobenzoylamino)-2-methylbenzo[b]furan (115 mg).
mp: 196°–197° C.; NMR (CDCl$_3$, δ): 2.07 (3H, s), 2.50 (3H, s), 5.20 (2H, s), 7.27–7.45 (5H, m), 7.81 (1H, br s), 8.32 (1H, d, J=7 Hz)

The following compounds [Examples 14 (2) to (7)] were obtained according to a similar manner to that of Example 14 (1).

Example 14 (2)
3-(1-Acetoxyethyl)-7-(2,6-dichlorobenzoylamino)-2-methylbenzo[b]furan
mp: 180°–181° C.; NMR (CDCl$_3$, δ): 1.17 (3H, d, J=7 Hz), 2.04 (3H, s), 2.48 (3H, s), 6.03 (1H, q, J=7 Hz), 7.20–7.43 (4H, m), 7.47 (1H, d, J=8 Hz), 7.80 (1H, br s), 8.30 (1H, d, J=8 Hz)

Example 14 (3)
7-(2,6-Dichlorobenzoylamino)-3-ethoxycarbonyloxymethyl-2-methylbenzo[b]furan
mp: 178°–179° C.; NMR (CDCl$_3$, δ): 1.39 (3H, t, J=7 Hz), 2.50 (3H, s), 4.19 (2H, q, J=7 Hz), 5.25 (2H, s), 7.25–7.45 (5H, m), 7.80 (1H, br s), 8.30 (1H, d, J=8 Hz)

Example 14 (4)
7-(2,6-Dichlorobenzoylamino)-3-diethoxyphosphoryloxymethyl-2-methylbenzo[b]furan
mp: 149°–152° C.; NMR (CDCl$_3$, δ): 1.28 (6H, t, J=7 Hz), 2.50 (3H, s), 4.06 (4H, quint., J=7 Hz), 5.17 (2H, d, J=8 Hz), 7.25–7.45 (5H, m), 7.80 (1H, br s), 8.31 (1H, d, J=8 Hz)

Example 14 (5)
3-Benzoyloxymethyl-7-(2,6-dichlorobenzoylamino)-2-methylbenzo[b]furan
mp: 191°–192° C.; NMR (CDCl$_3$, δ): 2.55 (3H, s), 5.45 (2H, s), 7.25–7.45 (7H, m), 7.55 (1H, t, J=8 Hz), 7.82 (1H, br s), 8.01 (2H, d, J=8 Hz), 8.32 (1H, d, J=8 Hz)

Example 14 (6)
3-Cyclohexylcarbonyloxymethyl-7-(2,6-dichlorobenzoylamino)-2-methylbenzo[b]furan
mp: 207°–209° C.; NMR (CDCl$_3$, δ): 1.10–1.95 (10H, m), 2.30 (1H, m), 2.50 (3H, s), 5.19 (2H, s), 7.25–7.45 (5H, m), 7.81 (1H, br s), 8.30 (1H, d, J=8 Hz)

Example 14 (7)
3-(4-Carboxybutyryl)oxymethyl-7-(2,6-dichlorobenzoylamino)-2-methylbenzo[b]furan
mp: 150°–152° C.; NMR (CDCl$_3$:CD$_3$OD=9:1, δ): 1.93 (2H, quint., J=7 Hz), 2.33 (2H, t, J=7 Hz), 2.40 (2H, t, J=7 Hz), 2.50 (3H, s), 5.21 (2H, s), 7.25–7.45 (5H, m), 8.23 (1H, d, J=8 Hz)

Example 15
A mixture of 3-(4-carboxybutyryl)oxymethyl-7-(2,6-dichlorobenzoylamino)-2-methylbenzo[b]furan (2.27 g), disuccinimidyl carbonate (2.51 g) and pyridine (1.16 g) in acetonitrile (100 ml) was stirred at ambient temperature for 2 days. The reaction mixture was concentrated in vacuo and the residue was crystallized from a mixture of ethyl acetate and hexane to give 7-(2,6-dichlorobenzoylamino)-2-methyl-3-(4-succinimidyloxy-carbonylbutyryl)oxymethylbenzo[b]furan (2.6 g).
mp: 117°–121° C.; NMR (CDCl$_3$, δ): 2.05 (2H, quint., J=7 Hz), 2.48 (2H, t, J=7 Hz), 2.50 (3H, s), 2.68 (2H, t, J=7 Hz), 2.81 (4H, s), 5.22 (2H, s), 7.29 (1H, t, J=8 Hz), 7.32–7.45 (4H, m), 7.89 (1H, br s), 8.30 (1H, d, J=8 Hz)

The following compounds [Examples 16 (1) to (6)] were obtained according to a similar manner to that of Preparation 10.

Example 16 (1)
3-(Benzimidazol-2-ylthiomethyl)-7-(2,6-dichlorobenzoylamino)-2-methylbenzo[b]furan
mp: 155° C.; NMR (CDCl$_3$, δ): 2.38 (3H, s), 4.60 (2H, s), 7.18–7.40 (8H, m), 7.70 (1H, d, J=8 Hz), 7.80 (1H, br s), 8.28 (1H, d, J=8 Hz), 9.18 (1H, br s)

Example 16 (2)
7-(2,6-Dichlorobenzoylamino)-3-ethoxycarbonylmethylthiomethyl-2-methylbenzo[b]furan
mp: 118°–122° C.; NMR (CDCl$_3$, δ): 1.28 (3H, t, J=8 Hz), 2.44 (3H, s), 3.08 (2H, s), 3.92 (2H, s), 4.16 (2H, q, J=8 Hz), 7.20–7.45 (5H, m), 7.79 (1H, br s), 8.30 (1H, d, J=8 Hz)

Example 16 (3)
7-(2,6-Dichlorobenzoylamino)-3-(2-hydroxyethyl)thiomethyl-2-methylbenzo[b]furan
mp: 164°–167° C.; NMR (CDCl$_3$:CD$_3$OD=9:1, δ): 2.43 (3H, s), 2.62 (2H, t, J=7 Hz), 3.70 (2H, t, J=7 Hz), 3.82 (2H, s), 7.27 (1H, t, J=8 Hz), 7.30–7.45 (4H, m), 8.12 (1H, d, J=8 Hz)

Example 16 (4)

7-(2,6-Dichlorobenzoylamino)-3-[(imidazol-1-yl)thiomethyl]-2-methylbenzo[b]furan hydrochloride mp: 218°–221° C.; NMR (DMSO-d$_6$, δ): 2.23 (3H, s), 4.62 (2H, s), 7.25 (1H, t, J=8 Hz), 7.41 (1H, d, J=8 Hz), 7.47–7.60 (3H, m), 7.72 (2H, s), 7.82 (1H, d, J=8 Hz)

Example 16 (5)

7-(2,6-Dichlorobenzoylamino)-3-(dimethoxyphosphorylmethyl)-2-methylbenzo[b]furan mp: 215°–218° C.; NMR (CDCl$_3$, δ): 2.43 (3H, d, J=4 Hz), 3.12 (2H, d, J=20 Hz), 3.68 (6H, d, J=9 Hz), 7.20–7.45 (5H, m), 7.82 (1H, br s), 8.29 (1H, d, J=8 Hz)

Example 16 (6)

7-(2,6-Dichlorobenzoylamino)-3-methoxymethyl-2-methylbenzo[b]furan mp: 199°–200° C.; NMR (CDCl$_3$, δ): 2.45 (3H, s), 3.37 (3H, s), 4.54 (2H, s), 7.2–7.5 (5H, m), 7.81 (1H, br s), 8.30 (1H, d, J=7.5 Hz)

Example 17

A mixture of 3-chloromethyl-7-(2,6-dichlorobenzoylamino)-2-methylbenzo[b]furan (150 mg), imidazole (33 mg) and triethylamine (62 mg) in 1,2-dichloroethane (1.5 ml) was refluxed for 3 hours. The reaction mixture was evaporated in vacuo and the residue was purified by column chromatography on silica gel. The obtained oil was crystallized from a mixture of ethyl acetate and diisopropyl ether and the crystalline was treated with ethanolic hydrogen chloride. The separated solid was collected and washed with ethanol to give 7-(2,6-dichlorobenzoylamino)-3-(imidazol-1-yl)methyl-2-methylbenzo[b]furan hydrochloride (62 mg).

mp: >250° C.; NMR (DMSO-d$_6$, δ): 2.61 (3H, s), 5.61 (2H, s), 7.23 (1H, t, J=8 Hz), 7.37 (1H, d, J=8 Hz), 7.48–7.60 (3H, m), 7.70 (1H, d, J=3 Hz), 7.80 (1H, d, J=3 Hz), 7.83 (1H, d, J=8 Hz), 9.30 (1H, s)

Example 18

A mixture of 3-bromo-7-(2,6-dichlorobenzoylamino)-2-methylbenzo[b]furan (165 mg), 2-(tributylstannyl)pyridine (213 mg) and tetrakis(triphenylphosphine)palladium (10 mg) in 1,2-dimethoxyethane (3 ml) was refluxed for 18 hours. The reaction mixture was evaporated in vacuo and the residue was purified by column chromatography on silica gel. The obtained oil was dissolved in methanolic hydrogen chloride and to the solution was evaporated in vacuo. The residue was crystallized from ethyl acetate to give 7-(2,6-dichlorobenzoylamino)-2-methyl-3-(pyridin-2-yl)benzo[b]furan hydrochloride (45 mg).

mp: 240°–243° C.; NMR (DMSO-d$_6$, δ): 2.71 (3H, s), 7.32 (1H, t, J=8 Hz), 7.49–7.61 (4H, m), 7.71 (1H, d, J=8 Hz), 7.85–7.91 (2H, m), 8.15 (1H, m), 8.81 (1H, d, J=5 Hz)

Example 19

A solution of 5-(tert-butoxycarbonylamino)-7-(2,6-dichlorobenzoylamino)-2,3-dimethylbenzo[b]furan (1.56 g) in 4N-hydrogen chloride in ethyl acetate (10 ml) was stirred at ambient temperature for 1 hour and to the reaction mixture was added diethyl ether. The separated solid was collected, washed with diethyl ether and dried to give 5-amino-7-(2,6-dichlorobenzoylamino)-2,3-dimethylbenzo[b]furan hydrochloride (1.23 g).

mp: >250° C.; NMR (CDCl$_3$:CD$_3$OD=9:1, δ): 2.16 (3H, S), 2.40 (3H, s), 7.30–7.50 (4H, m), 8.12 (1H, s)

Example 20

A solution of 3-tert-butoxycarbonylaminomethyl-7-(2,6-dichlorobenzoylamino)-2-methylbenzo[b]furan (312 mg) in trifluoroacetic acid (2 ml) was stirred at ambient temperature for 10 minutes. The reaction mixture was concentrated in vacuo and to the residue was added aqueous saturated sodium bicarbonate. The separated solid was collected, washed with water and dried to give 3-aminomethyl-7-(2,6-dichlorobenzoylamino)-2-methylbenzo[b]furan (210 mg).

mp: 200°–203° C.; NMR (CDCl$_3$:CD$_3$OD=9:1, δ): 2.45 (3H, s), 3.89 (2H, s), 7.18–7.48 (5H, m), 8.22 (1H, d, J=7 Hz)

Example 21 (1)

A mixture of 5-amino-7-(2,6-dichlorobenzoylamino)-2,3-dimethylbenzo[b]furan hydrochloride (116 mg) and acetic anhydride (74 mg) in acetic acid (1 ml) was stirred at 80° C. for 1.5 hours. The reaction mixture was cooled and to the mixture was added water. The separated solid was collected, washed with water and dried to give 5-acetylamino-7-(2,6-dichlorobenzoylamino)-2,3-dimethylbenzo[b]furan (97 mg).

mp: >250° C.; NMR (DMSO-d$_6$, δ): 2.05 (3H, s), 2.11 (3H, s), 2.38 (3H, s), 7.40–7.60 (3H, m), 7.79 (1H, s), 7.89 (1H, s), 10.00 (1H, s), 10.89 (1H, s)

The following compounds [Examples 21 (2) to (5)] were obtained according to a similar manner to that of Example 21 (1)

Example 21 (2)

3-Acetylaminomethyl-7-(2,6-dichlorobenzoylamino)-2-methylbenzo[b]furan mp: >250° C.; NMR (CDCl$_3$:CD$_3$OD=9:1, δ): 1.98 (3H, s), 2.47 (3H, s), 4.43 (2H, s), 7.20–7.50 (5H, m), 8.15 (1H, d, J=7 Hz)

Example 21 (3)

6-(3-Acetylamino-2,6-dichlorobenzoylamino)-1,2,3,4-tetrahydrodibenzofuran mp: >250° C.; NMR (CDCl$_3$, δ): 1.79–2.00 (4H, m), 2.28 (3H, s), 2.58–2.77 (4H, m), 7.20–7.28 (2H, m), 7.39 (1H, d, J=8 Hz), 7.66 (1H, br s), 7.88 (1H, br s), 8.28 (1H, dd, J=6 and 6 Hz), 8.42 (1H, d, J=8 Hz)

Example 21 (4)

3-Acetyl-7-(3-acetylamino-2,6-dichlorobenzoylamino)-2-methylbenzo[b]furan mp: >250° C.; NMR (DMSO-d$_6$, δ): 2.13 (3H, s), 2.12 (3H, s), 2.79 (3H, s), 7.35 (1H, t, J=8 Hz), 7.53 (1H, d, J=8 Hz), 7.75–7.90 (3H, m), 9.72 (1H, s)

Example 21 (5)

3-Acetyl-7-(6-acetylamino-2-chlorobenzoylamino)-2-methylbenzo[b]furan mp: 250°–252.5° C.; NMR (CDCl$_3$:CD$_3$OD=20:1, δ): 2.17 (3H, s), 2.67 (3H, s), 2.80 (3H, s), 7.29 (1H, d, J=8 Hz), 7.38 (1H, t, J=8 Hz), 7.42 (1H, t, J=8 Hz), 7.78 (1H, d, J=8 Hz), 8.08 (1H, d, J=8 Hz), 8.15 (1H, d, J=8 Hz)

The following compounds [Examples 22 (1) to (4)] were obtained according to a similar manner to that of Preparation 11 (1).

Example 22 (1)

3-(2-Carboxyethyl)-7-(2,6-dichlorobenzoylamino)-2-methylbenzo[b]furan mp: 211°–213° C.; NMR (CDCl$_3$:CD$_3$OD=9:1, δ): 2.42 (3H, s), 2.67 (2H, t, J=7.5 Hz), 2.95 (2H, t, J=7.5 Hz), 7.23–7.29 (2H, m), 7.32–7.43 (3H, m), 8.28 (1H, m)

Example 22 (2)

5-Carboxy-7-(2,6-dichlorobenzoylamino)-2,3-dimethylbenzo[b]furan mp: >250° C.; NMR (CDCl$_3$:CD$_3$OD=1:1, δ): 2.20 (3H, s), 2.41 (3H, s), 7.30–7.50 (3H, m), 8.03 (1H, s), 8.68 (1H, s)

Example 22 (3)

7-[N-(6-Carboxy-2-chlorophenyl)carbamoyl]-2,3-dimethylbenzo[b]furan mp: 194°–195° C.; NMR (CDCl$_3$, δ): 2.18 (3H, s), 2.43 (3H, s), 7.27 (1H, t, J=7.5 Hz), 7.30 (1H, t, J=7.5 Hz), 7.59 (1H, d, J=7.5 Hz), 7.67 (1H, d, J=7.5 Hz), 7.87 (1H, d, J=7.5 Hz), 8.07 (1H, d, J=7.5 Hz)

Example 22 (4)

3-Carboxymethyl-7-(2,6-dichlorobenzoylamino)-2-methylbenzo[b]furan mp: >250° C.; NMR (DMSO-d$_6$, δ): 2.40 (3H, s), 3.63 (2H, s), 7.20 (1H, t, J=8 Hz), 7.30 (1H, d, J=8 Hz), 7.49 (1H, m), 7.54–7.60 (2H, m), 7.78 (1H, d, J=8 Hz)

The following compound was obtained according to a similar manner to that of Preparation 33.

Example 23

3-Chloromethyl-7-(2,6-dichlorobenzoylamino)-2-methylbenzo[b]furan mp: 216°–217° C.; NMR (CDCl$_3$, δ): 2.49 (3H, s), 4.70 (2H, s), 7.30 (1H, t, J=8 Hz), 7.35–7.43 (4H, m), 7.80 (1H, br s), 8.33 (1H, d, J=8 Hz)

Example 24 (1)

A mixture of 3-(2-carboxyethyl)-7-(2,6-dichlorobenzoylamino)-2-methylbenzo[b]furan (90 mg), 3-(3-dimethylaminopropyl)-1-ethylcarbodiimide (43 mg) and 1-hydroxybenzotriazole (37 mg) in N,N-dimethylformamide (1 ml) was stirred at ambient temperature for 30 minutes. To the mixture was added dimethylamine hydrochloride (22 mg) and the mixture was stirred for 5 hours. The reaction mixture was poured into cold water and the separated oil was extracted with ethyl acetate. The extract was washed with brine, dried over sodium sulfate and concentrated in vacuo. The residue was purified by column chromatography on silica gel and the obtained oil was crystallized from diisopropyl ether to give 7-(2,6-dichlorobenzoylamino)-3-(2-N,N-dimethylcarbamoylethyl)-2-methylbenzo[b]furan (67 mg).

mp: 163°–169° C.; NMR (CDCl$_3$, δ): 2.42 (3H, s), 2.62 (2H, t, J=7 Hz), 2.91 (3H, s), 2.95 (3H, s), 2.98 (2H, t, J=7 Hz), 7.23–7.28 (2H, m), 7.31–7.44 (3H, m), 7.83 (1H, br s), 8.30 (1H, m)

The following compounds [Examples 24 (2) to (11)] were obtained according to a similar manner to that of Example 24 (1).

Example 24 (2)

3-[(N-Cyclopentyl)carbamovlmethyl]-7-(2,6-dichlorobenzoylamino)-2-methylbenzo[b]furan mp: 247°–248° C.; NMR (DMSO-d$_6$, δ): 1.32–1.58 (4H, m), 1.58–1.85 (4H, m), 2.41 (3H, s), 3.41 (2H, s), 3.99 (1H, m), 7.20 (1H, t, J=8 Hz), 7.37 (1H, d, J=8 Hz), 7.48 (1H, m), 7.58 (2H, d, J=8 Hz), 7.77 (1H, d, J=8 Hz), 8.10 (1H, d, J=8 Hz)

Example 24 (3) 7-(2,6-Dichlorobenzoylamino)-2-methyl-3-{[N-(pyridin-2-yl)methyl]carbamoylmethyl}benzo[b]furan hydrochloride mp: 221°–224° C.; NMR (DMSO-d$_6$, δ): 2.44 (3H, s), 3.63 (2H, s), 4.55 (2H, d, J=6 Hz), 7.20 (1H, t, J=8 Hz), 7.37 (1H, d, J=8 Hz), 7.49 (1H, m), 7.58 (2H, d, J=8 Hz), 7.68 (1H, d, J=7 Hz), 7.72 (1H, m), 7.79 (1H, d, J=8 Hz), 8.28 (1H, t, J=7 Hz), 8.73 (1H, d, J=7 Hz), 8,90 (1H, m)

Example 24 (4)

7-(2,6-Dichlorobenzoylamino)-3-{[N-(2-methoxyethyl)]carbamoylmethyl}-2-methylbenzo[b]furan mp: 215°–216° C.; NMR (DMSO-d$_6$, δ): 3.18–3.25 (5H, m), 3.35 (2H, t, J=7 Hz), 3.47 (2H, s), 7.20 (1H, t, J=8 Hz), 7.38 (1H, d, J=8 Hz), 7.45–7.60 (3H, m), 7.78 (1H, d, J=8 Hz), 8.20 (1H, br t, J=8 Hz)

Example 24 (5)

7-(2,6-Dichlorobenzoylamino)-3-{[N-(2-hydroxyethyl)]carbamoylmethyl}-2-methylbenzo[b]furan mp: 175°–178° C.; NMR (DMSO-d$_6$, δ): 2.42 (3H, m), 3.13 (2H, t, J=7 Hz), 3.40 (2H, t, J=7 Hz), 3.47 (2H, s), 4.69 (1H, t, J=7 Hz), 7.19 (1H, t, J=8 Hz), 7.36 (1H, t, J=8 Hz), 7.46–7.60 (3H, m), 7.74–7.80 (1H, m)

Example 24 (6)

7-(2,6-Dichlorobenzoylamino)-2-methyl-3-[(morpholin-4-yl)carbonylmethyl]benzo[b]furan mp: 260°–261° C.; NMR (DMSO-d$_6$, δ): 2.39 (3H, s), 3.40–3.60 (8H, m), 3.75 (2H, s), 7.18 (1H, t, J=8 Hz), 7.29 (1H, d, J=8 Hz), 7.40–7.60 (3H, m), 7.77 (1H, d, J=8 Hz)

Example 24 (7)

7-(2,6-Dichlorobenzoylamino)-2-methyl-3-{[N-(5-trifluoromethyl-1,3,4-thiadiazol-2-yl)]carbamoylmethyl}-benzo[b]furan mp: >260° C.; NMR (DMSO-d$_6$, δ): 2.47 (3H, s), 4.00 (2H, s), 7.21 (1H, t, J=8 Hz), 7.38 (1H, d, J=8 Hz), 7.40–7.60 (3H, m), 7.79 (1H, d, J=8 Hz)

Example 24 (8)

7-(2,6-Dichlorobenzoylamino)-2,3-dimethyl-5-(4-methylpiperazin-1-yl)carbonylbenzo[b]furan mp: 128°–138° C.; NMR (CDCl$_3$, δ): 2.15 (3H, s), 2.34 (3H, s), 2.38 (3H, s), 2.40–2.60 (4H, m), 3.50–3.70 (2H, m), 3.70–3.90 (2H, m), 7.30–7.45 (3H, m), 7.93 (1H, s), 8.31 (1H, s)

Example 24 (9)

7-(2,6-Dichlorobenzoylamino)-2,3-dimethyl-5-(morpholin-4-yl)carbonylbenzo[b]furan mp: 219°–221° C.; NMR (CDCl$_3$, δ): 2.16 (3H, s), 2.39 (3H, s), 3.60–3.90 (8H, m), 7.30–7.45 (3H, m), 7.90 (1H, s) 8.31 (1H, s)

Example 24 (10)

7-(2,6-Dichlorobenzoylamino)-5-(dimethylamino)acetylamino-2,3-dimethylbenzo[b]furan mp: 115°–119° C.; NMR (DMSO-d$_6$, δ): 2.11 (3H, s), 2.30 (6H, s), 2.38 (3H, s), 3.08 (2H, s), 7.42–7.62 (3H, m), 7.78 (1H, s), 7.99 (1H, s), 9.80 (1H, s)

Example 24 (11)

5-(Acetylamino)acetylamino-7-(2,6-dichlorobenzoylamino)-2,3-dimethylbenzo[b]furan mp: >250° C.; NMR (DMSO-d$_6$, δ): 1.89 (3H, s), 2.10 (3H, s), 2.38 (3H, s), 3.88 (2H, d, J=6 Hz), 7.43–7.62 (3H, m), 7.75 (1H, s), 7.95 (1H, s), 8.20 (1H, t, J=6 Hz), 10.03 (1H, s)

Example 25

A solution of 7-(2,6-dichlorobenzoylamino)-3-(1-hydroxy-1-methylethyl)-2-methylbenzo[b]furan (150 mg) in 4N-hydrogenchloride in ethyl acetate was refluxed for 2 hours. The reaction mixture was concentrated in vacuo and the residue was purified by column chromatography on silica gel. The obtained oil was crystallized from a mixture of diethyl ether and hexane to give 7-(2,6-dichlorobenzoylamino)-2-methyl-3-(1-methylvinyl)benzo[b]furan (72 mg).

mp: 147°–148° C.; NMR (CDCl$_3$, δ): 2.18 (3H, s), 2.49 (3H, s), 5.10 (1H, s), 5.30 (1H, s), 7.20–7.45 (5H, m), 7.82 (1H, br s), 8.30 (1H, d, J=8 Hz)

Example 26

A solution of 7-(2,6-dichlorobenzoylamino)-3-hydroxymethyl-2-methylbenzo[b]furan (140 mg), triethylamine (61 mg) and ethyl isocyanate (35 mg) in dichloromethane was stirred at ambient temperature for 5 hours. The raction mixture was concentrated in vacuo and the residue was purified by column chromatography on silica gel. The obtained oil was crystallized from diethyl ether to give 7-(2,6-dichlorobenzoylamino)-3-(N-ethylcarbamoyloxymethyl)-2-methylbenzo[b]furan (125 mg).

mp: 225°–226° C.; NMR (CDCl$_3$, δ): 1.12 (3H, t, J=8 Hz), 2.49 (3H, s), 3.21 (2H, m), 4.65 (1H, m), 5.18 (2H, s), 7.25–7.45 (5H, m), 7.82 (1H, br s), 8.31 (1H, d, J=8 Hz)

The following compound was obtained according to a similar manner to that of Preparation 39 (1).

Example 27

7-(2,6-Dichlorobenzoylamino)-3-(1-hydroxyiminoethyl)-2-methylbenzo[b]furan mp: 237°–238° C.; NMR (CDCl$_3$:CD$_3$OD=9:1, δ): 2.35 (3H, s), 2.57 (3H, s), 7.27 (1H, t, J=8 Hz), 7.30–7.45 (3H, m), 7.49 (1H, d, J=8 Hz), 8.22 (1H, d, J=8 Hz)

Example 28

A mixture of 3-(1-cyclohexyl)hydroxymethyl-7-(2,6-dichlorobenzoylamino)-2-methylbenzo[b]furan (65 mg) and triethylsilane (87 mg) in trifluoroacetic acid (3 ml) was stirred at ambient temperature for overnight. The reaction mixture was concentrated in vacuo. To the residue was added aqueous saturated sodium bicarbonate and the separated oil was extracted with ethyl acetate. The extract was washed with brine, dried over sodium sulfate and concentrated in vacuo. The residue was purified by column chromatography on silica gel and the obtained oil was crystallized from hexane to give 3-cyclohexylmethyl-7-(2,6-dichlorobenzoylamino)-2-methylbenzo[b]furan (42 mg).

mp: 189°–190° C.; NMR (CDCl$_3$, δ): 0.85–1.10 (2H, m), 1.10–1.30 (3H, m), 1.50–1.80 (6H, m), 2.37 (3H, s), 2.47 (2H, d, J=8 Hz), 7.20–7.30 (2H, m), 7.30–7.45 (3H, m), 7.82 (1H, br s), 8.38 (1H, m)

Example 29

A mixture of 7-(2,6-dichlorobenzoylamino)-2-methyl-3-(4-succinimidyloxycarbonvlbutyryl)oxymethyl, benzo[b]furan (112 mg), aminomethylenebis(phosphonic acid) (77 mg) and triethylamine (162 mg) in N,N-dimethylformamide (2 ml) and water (0.5 ml) was stirred at ambient temperature for 3 hours. Then, the reaction mixture was poured into cold water. The aqueous solution was washed with ethyl acetate and the pH of the solution was adjusted to 2 with 2N-hydrochloric acid. The separated solid was collected, washed with ethyl acetate and water and dried to give 4-{[7-(2,6-dichlorobenzoylamino)-2-methylbenzo[b]furan-3-yl]methyloxycarbonyl}butyrylaminomethylenebis(phosphonic acid) (50 mg).

mp: 190°–195° C.; NMR (DMSO-d$_6$, δ): 1.73 (2H, quint., J=7 Hz), 2.20 (2H, t, J=7 Hz), 2.32 (2H, t, J=7 Hz), 4.43 (1H, dt, J=9 and 20 Hz), 5.22 (2H, s), 7.25 (1H, t, J=8 Hz), 7.41 (1H, d, J=8 Hz), 7.45–7.60 (3H, m), 7.80 (1H, d, J=8 Hz)

Example 30

Nitric acid (d; 1.5, 0.033 ml) was added to a solution of 6-(2,6-dichlorobenzoylamino)-1,2,3,4-tetrahydrodibenzofuran (200 mg) in acetic acid at 4° C. The mixture was stirred at ambient temperature for 5 hours and poured into cold water. The separated solid was collected and washed with isopropyl alcohol to give 6-(2,6-dichlorobenzoylamino)-7-nitro-1,2,3,4-tetrahydrodibenzofuran (17 mg).

mp: 246°–248° C.; NMR (CDCl$_3$, δ): 1.81–2.06 (4H, m), 2.61–2.72 (2H, m), 2.80–2.90 (2H, m), 7.29–7.46 (4H, m), 8.06 (1H, d, J=8 Hz), 9.21 (1H, br s)

Example 31

A solution of 5-carboxy-7-(2,6-dichlorobenzoylamino)-2,3-dimethylbenzo[b]furan (152 mg) and triethylamine (61 mg) in dichloromethane (3 ml) was stirred at –20° C. and to the solution was added isobutyl chloroformate (66 mg). The mixture was stirred at –20° C. for 3 hours and added to cold (–20° C.) solution of 10% ammonia in methanol (3 ml). The reaction mixture was stirred at ambient temperature for 10 minutes and partitioned between dichloromethane and water. The organic layer was washed with brine, dried over sodium sulfate and concentrated in vacuo. The residue was purified by column chromatography on silica gel and the obtained oil was crystallized from ethyl acetate to give 5-carbamoyl-7-(2,6-dichlorobenzoylamino)-2,3-dimethylbenzo[b]furan (70 mg).

mp: >250° C.; NMR (CDCl$_3$:CD$_3$OD=1:1, δ): 2.19 (3H, s), 2.40 (3H, s), 7.30–7.50 (3H, m), 7.90 (1H, s), 8.45 (1H, s)

Example 32

A mixture of 5-amino-7-(2,6-dichlorobenzoylamino)-2,3-dimethylbenzo[b]furan hydrochloride (155 mg), triethylamine (61 mg) and trichloroacetyl isocyanate (115 mg) was stirred at ambient temperature for 1 hour. Then, the mixture was concentrated in vacuo and to the residue was added methanol (3 ml) and aqueous 1N-sodium hydroxide (2 ml). The mixture was stirred at 60° C. for 15 minutes and the methanol was evaporated in vacuo. The separated solid was collected, washed with water and dried to give 7-(2,6-dichlorobenzoylamino)-2,3-dimethyl-5-ureidobenzo[b]furan (130 mg).

mp: >250° C.; NMR (DMSO-d$_6$, δ): 2.10 (3H, s), 2.37 (3H, s), 5.75 (2H, s), 7.40–7.63 (4H, m), 7.67 (1H, s), 8.63 (1H, s)

Example 33

A mixture of 3-chloromethyl-7-(2,6-dichlorobenzoylamino)-2-methylbenzo[b]furan (20 mg) and potassium carbonate (7.5 mg) in methanol was refluxed for 1 hour. The mixture was cooled and poured into water. The separated oil was extracted with ethyl acetate and the extract was washed with water, dried over sodium sulfate and evaporated in vacuo. The residue was purified by preparative TLC to give 7-(2,6-dichlorobenzoylamino)-2,3-dihydro-2-methoxy-2-methyl-3-methylenebenzo[b]furan (5 mg).

mp: 208°–210° C.; NMR (CDCl$_3$, δ): 1.64 (3H, s), 3.16 (3H, s), 5.20 (1H, s), 5.71 (1H, s), 7.00 (1H, t, J=7.5 Hz), 7.22 (1H, d, J=7.5 Hz), 7.30–7.50 (3H, m), 7.61 (1H, br s), 8.38 (1H, d, J=7.5 Hz)

Example 34

A mixture of 6-(2,6-dichlorobenzoylamino)- 1-hydroxy-1,2,3,4-tetrahydrodibenzofuran (500 mg), methanesulfonyl chloride (880 mg) and triethylamine (1.19 g) in dichloromethane was refluxed for 4 hours. The mixture was washed with brine, dried over sodium sulfate and evaporated in vacuo. The residue was purified by column chromatography on silica gel and the obtained oil was crystallized from a mixture of 2-propanol and water to give 6-(2,6-dichlorobenzoylamino)-3,4-dihydrodibenzofuran (173 mg).

mp: 165°–167° C.; NMR (CDCl$_3$, δ): 2.58–2.68 (2H, m), 2.95 (2H, t, J=9 Hz), 5.77 (1H, m), 6.50 (1H, d, J=9 Hz), 7.23–7.42 (5H, m), 7.82 (1H, br s), 8.29 (1H, d, J=8 Hz)

Example 35

A mixture of 6-(2,6-dichlorobenzoylamino)-3,4-dihydrodibenzofuran (100 mg), 4-methylmorpholine N-oxide (39 mg) and osmium tetroxide (10% solution in tert-butanol, 1 drop) in a mixture of acetone (2 ml) and water (0.5 ml) was stirred at ambient temperature for 6 hours. The mixture was partitioned between 1% aqueous sodium bisulfite and ethyl acetate. The organic layer was separated, washed with aqueous saturated sodium bicarbonate and brine, dried over sodium sulfate and evaporated in vacuo. The residue was purified by column chromatography on silica gel and the obtained oil was crystallized from diisopropyl ether to give 7-(2,6-dichlorobenzoylamino)-1,2-dihydroxy-1,2,3,4-tetrahydrodibenzofuran (74 mg).

mp: 206°–209° C.; NMR (DMSO-d$_6$, δ): 1.80 (1H, m), 2.07 (1H, m), 2.69–2.84 (2H, m), 3.83 (1H, m), 4.63 (1H, d, J=6 Hz), 4.71 (1H, m), 5.94 (1H, d, J=6 Hz), 7.22 (1H, t, J=8 Hz), 7.40 (1H, d, J=8 Hz), 7.49 (1H, t, J=8 Hz), 7.57 (2H, d, JS=8 Hz), 7.80 (1H, d, J=8 Hz)

Example 36

A solution of hydrogen peroxide in trifluoroacetic acid (1M, 0.32 ml) wa s added to a solution of 6-(2,6-dichlorobenzoylamino)-3,4-dihydro-1H-thiopyrano-[4,3-b]benzofuran (120 mg) in trifluoroacetic acid (2.5 ml) at 4° C. The mixture was stirred at ambient temperature for 30 minutes and to the mixture was added water. The separated solid was collected and dried. The obtained solid was suspended in hot ethanol and to the mixture was added water. The mixture was cooled and the separated solid was collected to give 6-(2,6-dichlorobenzoylamino)-3,4-dihydro-1H-thiopyrano[4, 3-b]-benzofuran 2-oxide (70 mg).

mp: >250° C.; NMR (DMSO-d$_6$, δ): 3.10–3.20 (2H, m), 3.30–3.50 (2H, m), 4.03–4.12 (2H, m), 7.28 (1H, t, J=8SHz), 7.40 (1H, d, J=8 Hz), 7.46–7.61 (3H, m), 8.85 (1H, d, J=8 Hz)

The following compounds [Examples 37 (1) to (3)] were obtained according to a similar manner to that of Preiaration 42 (1).

Example 37 (1)

6-(3-Amino-2,6-dichlorobenzoylamino)-1,2,3,4-tetrahydrodibenzofuran mp: 197°–200° C.; NMR (CDCl$_3$, δ): 1.80–2.00 (4H, m), 2.60–2.78 (4H, m), 4.26 (2H, br s), 6.80 (1H, d, J=8 Hz), 7.18 (1H, d, J=8 Hz),7.20–7.30 (2H, m) 7.88 (1H, br s), 8.32 (1H, m)

Example 37 (2)

3-Acetyl-7-(3-amino-2,6-dichlorobenzoylamino)-2-methylbenzo[b]furan mp: >250° C.; NMR (DMSO-d$_6$, δ): 2.61 (3H, s), 2.79 (3H, s), 5.72 (2H, s), 6.87 (1H, d, J=8 Hz), 7.19 (1H, d, J=8 Hz), 7.33 (1H, t, J=8 Hz), 7.78 (1H, d, J=8 Hz), 7.82 (1H, d, J=8 Hz)

Example 37 (3)

7-(3-Amino-2,6-dichlorobenzoylamino)-2,3-dimethylbenzo[b]furan mp: 245°–246.5° C.; NMR (DMSO-d$_6$, δ): 2.15 (3H, s), 2.39 (3H, s), 5.68 (2H, br s), 6.83 (1H, d, J=8 Hz), 7.19 (2H, m), 7.30 (1H, d, J=8 Hz), 7.72 (1H, d, J=8 Hz)

Example 38 (1)

To a mixture of 6-(3-amino-2,6-dichlorobenzoylamino)-1,2,3,4-tetrahydrodibenzofuran (100 mg) and triethylamine (54 mg) in chloroform (3 ml) was added chloroacetyl chloride (36 mg) under ice cooling. The mixture was stirred at ambient temperature for 2 hours, and then dimethyl amine hydrochloride (65 mg) was added to the mixture and additionally the mixture was stirred for 12 hours. The mixture was washed with water and brine, dried over magnesium sulfate, and evaporated in vacuo. The residue was purified by column chromatography on silica gel eluting with (ethyl acetate: n-hexane=1:1) and the obtained oil was crystallized from ethanol to give 6-[2,6-dichloro-3-(2-dimethylaminoacetylamino)benzoylamino]-1,2,3,4-tetrahydrodibenzofuran (62 mg).

mp: 207° C.; NMR (CDCl$_3$, δ): 1.79–2.00 (4H, m), 2.42 (6H, s), 2.59–2.77 (4H, m), 3.15 (2H, s), 7.24 (2H, m), 7.40 (1H, d, J=8 Hz), 7.89 (1H, br s), 8.29 (1H, dd, J=1 and 8 Hz), 8.51 (1H, d, J=8 Hz), 9.99 (1H, br s)

The following compounds [Examples 38 (2) to (6)] were obtained according to a similar manner to that of Example 38 (1).

Example 38 (2)

7-(2,6-Dichloro-3-dimethylaminoacetylaminobenzoyl-amino)-2,3-dimethylbenzo[b]furan mp: 211.5°–213° C.; NMR (CDCl$_3$, δ): 2.15 (3H, s), 2.37 (3H, s), 2.41 (6H, s), 3.13 (2H, s), 7.22 (2H, m), 7.40 (1H, d, J=8 Hz), 7.83 (1H, br s), 8.28 (1H, d, J=8 Hz), 8.51 (1H, d, J=8 Hz)

Example 38 (3)

6-[2,6-Dichloro-3-(morpholin-4-yl)-acetylaminobenzoylamino]-1,2,3,4-tetrahydrodibenzofuran mp: 252°–254° C.; NMR (CDCl$_3$, δ): 1.79–2.02 (4H, m), 2.60–2.78 (8H, m), 3.23 (2H, s), 3.72–3.82 (4H, m), 7.25 (2H, d, J=6 Hz), 7.40 (1H, d, J=8 Hz), 7.89 (1H, br s), 8.28 (1H, dd, J=6 and 6 Hz), 8.56 (1H, d, J=8 Hz), 10.07 (1H, br s)

Example 38 (4)

3-Acetyl-7-(2,6-dichloro-3-dimethylaminoacetylamino-benzoylamino)-2-methylbenzo[b]furan mp: 235°–236° C.; NMR (CDCl$_3$, δ): 2.42 (6H, s), 2.66 (3H, s), 2.79 (3H, s), 3.15 (2H, s), 7.35–7.40 (2H, m), 7.72 (1H, d, J=8 Hz), 7.90 (1H, s), 8.32 (1H, d, J=8 Hz), 8.51 (1H, d, J=8 Hz)

Example 38 (5)

6-[2,6-Dichloro-3-[bis(2-methoxyethyl)aminoacetyl-amino]benzoylamino]-1,2,3,4-tetrahydrodibenzofuran mp: 168.5°–170.0° C.; NMR (CDCl$_3$, δ): 1.80–1.99 (4H, m), 2.60–2.68 (2H, m), 2.68–2.77 (2H, m), 2.88 (4H, t, J=5 Hz), 3.28 (6H, s), 3.44 (2H, s), 3.50 (4H, t, J=5 Hz), 7.22–7.28 (2H, m), 7.38 (1H, d, J=8 Hz), 7.87 (1H, br s), 8.30 (1H, dd, J=1.5 and 7 Hz), 8.58 (1H, d, J=8 Hz)

Example 38 (6)

6-(2,6-Dichloro-3-ureidobenzoylamino)-1,2,3,4-tetrahydrodibenzofuran mp: 242°–244° C.; NMR (DMSO-d$_6$, δ): 1.71–1.98 (4H, m), 2.53–2.79 (4H, m), 6.51 (2H, br s), 7.20 (1H, t, J=8 Hz), 7.30 (1H, d, J=8 Hz), 7.43 (1H, d, J=8 Hz), 7.82 (1H, d, J=8 Hz), 8.20–8.30 (2H, m)

Example 39 (1)

A mixture of 6-(3-amino-2,6-dichlorobenzoylamino)-1,2,3,4-tetrahydrodibenzofuran (100 mg), methanesulfonyl chloride (120 mg) and triethylamine (162 mg) in dichloromethane (3 ml) was stirred at ambient temperature for 2 hours. The reaction mixture was diluted with dichloromethane and washed with 1N-hydrochloric acid, aqueous saturated sodium bicarbonate and brine. The solution was dried over sodium sulfate and concentrated in vacuo. The residual oil was crystallized from ethanol to give 6-[2,6-dichloro-3-bis(methanesulfonyl)aminobenzoyl-amino]-1,2,3,4-tetrahydrodibenzofuran (87 mg).

mp: 237°–238.5° C.; NMR (CDCl$_3$, δ): 1.78–2.01 (4H, m), 2.57–2.80 (4H, m), 3.50 (6H, s), 7.23 (2H, d, J=6 Hz), 7.43 (1H, d, J=8 Hz), 7.50 (1H, d, J=8 Hz), 7.98 (1H, br s), 8.25 (1H, t, J=6 Hz)

The following compounds [Examples 39 (2) to (5)] were obtained according to a similar manner to that of Example 39 (1).

Example 39 (2)

6-(3-Acetoxyacetylamino-2,6-dichlorobenzoylamino)-1,2,3,4-tetrahydrodibenzofuran mp: 225°–227° C.; NMR (CDCl$_3$, δ): 1.78–2.00 (4H, m), 2.24 (3H, s), 2.58–2.77 (4H, m), 4.75 (2H, s), 7.20–7.29 (2H, m), 7.41 (1H, d, J=8 Hz), 7.88 (1H, br s), 8.27 (1H, dd, J=6 and 6 Hz), 8.46–8.55 (2H, m)

Example 39 (3)

6-(2,6-Dichloro-3-methoxyacetylaminobenzoylamino)-1,2,3,4-tetrahydrodibenzofuran mp: 217° C.; NMR (CDCl$_3$, δ): 1.79–2.01 (4H, m), 2.60–2.78 (4H, m), 3.55 (3H, s), 4.09 (2H, s), 7.24 (2H, d, J=6 Hz), 7.40 (1H, d, J=8 Hz), 7.90 (1H, br s), 8.29 (1H, m), 8.52 (1H, d, J=8 Hz), 8.98 (1H, br s)

Example 39 (4)

7-(2,6-Dichlorobenzoylamino)-2,3-dimethyl-5-(morpholin-4-yl)carbonylaminobenzo[b]furan mp: >250° C.; NMR (DMSO-d$_6$, δ): 2.10 (3H, s), 2.37 (3H, s), 3.38–3.50 (4H, m), 3.57–3.60 (4H, m), 7.40–7.60 (4H, m), 7.87 (1H, s), 8.61 (1H, s)

Example 39 (5)

7-(2,6-Dichlorobenzoylamino)-2-methyl-3-(morpholin-4-yl)carbonylaminomethylbenzo[b]furan mp: >250° C.; NMR (CDCl$_3$:CD$_3$OD=9:1, δ): 2.48 (3H, s), 3.33 (4H, t, J=5 Hz), 3.68 (4H, t, J=5 Hz), 4.45 (2H, d, J=6 Hz), 5.25 (1H, t, J=6 Hz), 7.25 (1H, t, J=7 Hz), 7.30–7.45 (4H, m), 8.17 (1H, d, J=7 Hz)

Example 40 (1)

A mixture of 6-(3-amino-2,6-dichlorobenzoylamino)-1,2,3,4-tetrahydrodibenzofuran (100 mg), aqueous 37% formaldehyde, sodium cyanoborohydride (70 mg) and acetic acid (5 drops) in acetonitrile (2 ml) was stirred at ambient temperature for 3 hours. The reaction mixture was partitioned between dichloromethane and aqueous saturated sodium bicarbonte. The organic layer was separated, washed with brine, dried over sodium sulfate and concentrated in vacuo. The residue was purified by preparative TLC on silica gel and the obtained oil was crystallized from diisopropyl ether to give 6-(2,6-dichloro-3-methylaminobenzoylamino)-1,2,3,4-tetrahydrodibenzofuran (21 mg).

mp: 160°–162° C.; NMR (CDCl$_3$, δ): 1.78–2.00 (4H, m), 2.58–2.78 (4H, m), 2.93 (3H, d, J=6 Hz), 4.52 (1H, m), 6.64 (1H, d, J=8 Hz), 7.18–7.30 (3H, m), 7.83 (1H, br s), 8.31 (1H, dd, J=1 and 8 Hz)

The following comopund was obtained according to a similar manner to that of Example 40 (1).

Example 40 (2)

7-(2-Chloro-6-dimethylaminobenzoylamino)-2,3-dimethylbenzo[b]furan mp: 118°–119° C.; NMR (CDCl$_3$, δ): 2.15 (3H, s), 2.37 (3H, s), 2.87 (6H, s), 6.94 (1H, d, J=8 Hz), 7.04 (1H, d, J=8 Hz), 7.17–7.30 (3H, m), 8.26–8.31 (2H, m)

Example 41

A solution of tetrabutylammonium fluoride in tetrahydrofuran (1M solution, 0.58 ml) was added to a solution of 7-(2,6-dichloro-3-triisopropylsilyloxybenzoylamino)-2,3-dimethylbenzo[b]furan (221 mg) in tetrahydrofuran (2 ml) at 4° C. The solution was stirred at 4° C. for 1 hour and concentrated in vacuo. The residue was purified by column chromatography on silica gel and the obtained oil was crystallized from diisopropyl ether to give 7-(2,6-dichloro-3-hydroxybenzoylamino)-2,3-dimethylbenzo[b]furan (152 mg).

mp: 191.5°–193.5° C.; NMR (CDCl$_3$, δ): 2.14 (3H, s), 2.36 (3H, s), 5.78 (1H, br s), 7.05 (1H, d, J=8 Hz), 7.20–7.31 (3H, m), 7.80 (1H, br s), 8.26 (1H, d, J=8 Hz)

Example 42

A solution of 7-[2,6-dichloro-3-(2-methoxyethyl)oxymethoxymethylbenzoylamino]-2,3-dimethylbenzo[b]furan (305 mg) in 10% methanolic hydrogen chloride (4.5 m.l) was refluxed for 1 hour. The reaction mixture was cooled and the separated solid was collected to give 7-(2,6-dichloro-3-hydroxymethylbenzoylamino)-2,3-dimethylbenzo[b]furan (217 mg).

mp: 258°–261° C.; NMR (DMSO-d$_6$, δ): 2.15 (3H, s), 2.39 (3H, s), 4.60 (2H, d, J=5 Hz), 5.61 (1H, t, J=5 Hz), 7.21 (1H, t, J=8 Hz), 7.31 (1H, d, J=8 Hz), 7.57 (1H, d, J=8 Hz), 7.62 (1h, d, J=8 Hz), 7.80 (1H, d, J=8 Hz)

Example 43

Aqueous saturated ammonium chloride (1 ml) was added dropwise to a suspension of 6-(2,6-dichloro-3-nitrobenzoylamino)-1,2,314-tetrahydrodibenzofuran (150 mg) and zinc (120 mg) in a mixture of tetrahydrofuran (1.5 ml) and ethanol (1 ml). The mixture was diluted with chloroform and the insoluble matter was filtered off. The organic layer of the filtrate was separated, washed with brine, dried over sodium sulfate and concentrated in vacuo. The residue was crystallized from ethyl acetate to give 6-(2,6-dichloro-3-hydroxyaminobenzoylamino)-1,2,3,4-tetrahydrodibenzofuran (40 mg).

mp: 175° C. (dec.); NMR (DMSO-d$_6$, δ): 1.73–1.96 (4H, m), 2.54–2.68 (2H, m), 2.68–2.78 (2H, m), 7.15–7.25 (2H, m), 7.30 (1H, d, J=8 Hz), 7.40 (1H, d, J=8 Hz), 7.78 (1H, d, J=8 Hz), 8.56 (1H, br s), 8.78 (1H, m)

The following compound was obtained according to a similar manner to that of Prenaration 2 (1).

Example 44

7-(2,6-Dichloro-3-ethoxycarbonylmethoxybenzoylamino)-2,3-dimethylbenzo[b]furan mp: 131°–133° C.; NMR (CDCl$_3$, δ): 1.32 (3H, t, J=7 Hz), 2.16 (3H, s), 2.38 (3H, s), 4.29 (2H, q, J=7 Hz), 4.73 (2H, s), 6.88 (1H, d, J=8 Hz), 7.20–7.27 (2H, m), 7.31 (1H, d, J=8 Hz), 7.80 (1H, br s), 8.28 (1H, d, J=8 Hz)

Example 45 (1)

A mixture of 6-(3-acetoxyacetylamino-2,6-dichlorobenzoylamino)-1,2,3,4-tetrahydrodibenzofuran (67 mg) and aqueous 1N-sodium hydroxide (0.5 ml) in a mixture of dichloromethane (1 ml) and methanol (1 ml) was stirred at ambient temperature for 1 hour. The mixture was partitioned between a mixture of dichloromethane and ethanol (8:2) and water. The organic layer was separated, washed with brine, dried over sodium sulfate and concentrated in vacuo. The residue was crystallized from ethanol to give 6-(2,6-dichloro-3-hydroxyacetylamino-benzoylamino)-1,2,3,4-tetrahydrodibenzofuran (30 mg).

mp: 245°–249° C.; NMR (CDCl$_3$:CD$_3$OD=9:1, δ): 1.80–2.00 (4H, m), 2.58–2.80 (4H, m), 4.20 (2H, s), 7.24 (2H, d, J=5 Hz), 7.41 (1H, d, J=8 Hz), 8.20 (1H, t, J=5 Hz), 8.47 (1H, d, J=8 Hz)

The following compound was obtained according to a similar manner to that of Example 45 (1).

Example 45 (2)

6-(2,6-Dichloro-3-methanesulfonylaminobenzoylamino)-1,2,3,4-tetrahydrodibenzofuran.

mp: 202°–204° C.; NMR (CDCl$_3$, δ): 1.79–2.01 (4H, m), 2.59–2.78 (4H, m), 3.08 (3H, s), 6.89 (1H, br s), 7.25 (2H, d, J=5 Hz), 7.43 (1H, d, J=8 Hz), 7.73 (1H, d, J=8 Hz), 7.87 (1H, br s), 8.26 (1H, t, J=5 Hz)

The following compound was obtained according to a similar manner to that of Preparation 43 (1).

Example 46

7-(2-Amino-6-methylbenzoylamino)-3-(1-hydroxy-1-methylethyl)-2-methylbenzo[b]furan mp: 127°–128° C.; NMR (CDCl$_3$, δ): 1.71 (6H, s), 1.80 (1H, s), 2.45 (3H, s), 2.56 (3H, s), 4.28 (2H, br s), 6.60 (1H, d, J=8 Hz), 6.66 (1H, d, J=8 Hz), 7.12 (1H, t, J=8 Hz), 7.20 (1H, t, J=8 Hz), 7.45 (1H, d, J=8 Hz), 7.91 (1H, br s), 8.23 (1H, d, J=8 Hz)

The following compound was obtained according to a similar manner to that of Preparation 18 (1).

Example 47

9-Acetyl-6-(2,6-dichlorobenzoylamino)-1,2,3,4-tetrahydrodibenzofuran mp: 212°–214° C.; NMR (CDCl$_3$, δ): 1.75–1.95 (4H, m), 2.67 (3H, s), 2.73 (2H, m), 2.90 (2H, m), 7.30–7.45 (3H, m), 7.72 (1H, d, J=7 Hz), 8.02 (1H, br s), 8.38 (1H, d, J=7 Hz)

The following compound was obtained according to a similar manner to that of Preparation 14.

Example 48

7-(2,6-Dichlorobenzoyl)-2,3,5-trimethylbenzo[b]furan mp: 143°–146° C.; MNR (CDCl$_3$, δ): 2.13 (3H, s), 2.29 (3H, s), 2.45 (3H, s), 7.30–7.50 (5H, m)

We claim:

1. A compound of the formula:

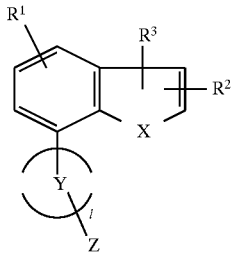

wherein $R^1$ is hydrogen, lower alkyl, an acyl group, amino, acylamino, nitro, halogen or hydroxy(lower)alkyl which may have one or more suitable substituent(s), $R^2$ is lower alkyl or acyl(lower)alkyl, $R^3$ is hydrogen, lower alkyl, lower alkenyl, cyclo(lower)alkyl(lower)alkyl, halogen, an acyl group, acyl(lower)alkyl, acylamino, acylamino(lower)alkyl, acyl(lower)alkenyl, acyloxy(lower)alkyl, acyl(lower)alkylthio(lower)alkyl, amino(lower)alkyl, mono- (or di-)lower alkylamino, lower alkylthio(lower)alkyl, mono-(or di)loweralkoxy(lower)alkyl which may have one or more suitable substituent(s), hydroxyimino(lower)alkyl which may have one or more suitable substituent(s), hydroxy(lower)alkyl which may have one or more suitable substituent(s), hydroxy(lower)alkylthio(lower)alkyl, lower alkyl substituted with heterocyclic group which may have one or more suitable substituent(s), heterocyclic group which may have one or more suitable substiutuents(s), or heterocyclicthio(lower)alkyl, in which $R^2$ and $R^3$ may be linked together to form
(1) lower alkylene which may have one or more suitable substituent(s),
(2) lower alkenylene which may have one or more suitable substituent(s), or
(3) a group of the formula:

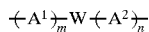

wherein $A^1$ and $A^2$ are each lower alkylene which may have one or more suitable substituent(s), and

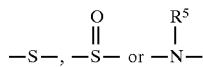

W is wherein $R^5$ is hydrogen, or an acyl group, and m and n are each an integer of 0 or 1, X is O Y is a group of the formula: —NHCO—, Z is aryl which may have one or more suitable substituent(s), l is an integer of 1, and a pharmaceutically acceptable salt thereof.

2. The compound of claim 1, wherein Z is naphthyl which may have one or more suitable substituent(s), or a group of the formula:

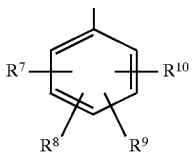

wherein $R^7$, $R^8$, $R^9$ and $R^{10}$ are each hydrogen, halogen, lower alkyl, nitro, lower alkoxy, an acyl group, cyclo(lower)alkyl, mono-(or di- or tri)halo(lower)alkyl, acylamino, aryl, amino, hydroxyamino, mono-(or di-)lower alkylamino, aryloxy, aryl(lower)alkoxy, hydroxy, hydroxy(lower)alkyl which may have one or more suitable substituent(s), heterocyclic group which may have one or more suitable substituent(s), mono-(or di-)lower alkylamino(lower)alkyl or acyl(lower)alkoxy.

3. The compound of claim 1, wherein $R^2$ is lower alkyl, carboxy(lower)alkyl or protected carboxyl(lower)alkyl, $R^3$ is hydrogen, lower alkyl, lower alkenyl, cyclo(lower)alkyl(lower)alkyl, cyclo(lower)alkylcarbonyloxy(lower)alkyl, halogen, lower alkanoyl, heterocyclic carbonyl(lower)alkyl, lower alkanoylamino, lower alkoxycarbonylamino(lower)alkyl, lower alkanoylamino(lower)alkyl, heterocyclic carbonylamino(lower)alkyl, carboxy(lower)alkenyl, protected carboxy(lower)alkenyl, lower alkanoyloxy(lower)alkyl, aroyloxy(lower)alkyl, protected carboxyoxy(lower)alkyl, protected carboxy(lower)alkylthio(lower)alkyl, amino(lower)alkyl, di-lower alkylamino, di-lower alkylaminocarbonyl(lower)alkyl, lower alkylaminocarbonyloxy(lower)alkyl, cyclo(lower)alkylaminocarbonyl(lower)alkyl, carboxy(lower)alkyl, protected carboxy(lower)alkyl, lower alkylthio(lower)alkyl, di-lower alkoxyphosphoryl(lower)alkyl, di-lower alkoxyphosphoryloxy(lower)alkyl, hydroxyimino(lower)alkyl, hydroxy(lower)alkyl which may have 1 to 3 suitable substituent(s), hydroxy(lower)alkylthio(lower )alkyl, di-lower alkylaminocarbonyl(lower)alkyl, carboxy(lower)alkanoyloxy(lower)alkyl, lower alkoxy(lower)alkyl, hydroxy(lower)alkylaminocarbonyl(lower)alkyl, lower alkoxy(lower)alkylaminocarbonyl(lower)alkyl, aminocarbonyl(lower)alkyl substituted with heterocyclic group which may have 1 to 3 suitable substituent(s), heterocyclic(lower)alkyl, heterocyclic(lower)-alkylaminocarbonyl(lower)alkyl, heterocyclic group which may have 1 to 3 suitable substituent(s) heterocyclicthio(lower)alkyl, or a group of the formula:

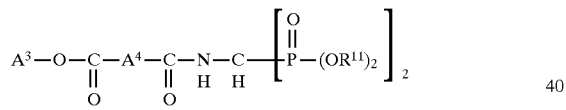

wherein $A^3$ is lower alkylene which may have 1 to 3 suitable substituent(s),
$R^{11}$ is hydrogen or lower alkyl, and
$A^4$ is lower alkylene or a group of the formula:

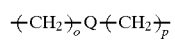

wherein Q is phenylene which may have 1 to 3 suitable substituent(s) or
cyclo(lower)alkylene which may have 1 to 3 suitable substituent(s), and o and are each an integer of 0 or 1, in which $R^2$ and $R^3$ may be linked together to form
(1) lower alkylene which may have 1 to 3 suitable substituent(s),
(2) lower alkenylene which may have 1 to 3 suitable substituent(s), or
(3) a group of the formula:

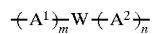

wherein $A^1$ and $A^2$ are each lower alkylene which may have 1 to 3 suitable substituent(s),

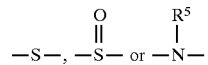

W is
wherein $R^5$ is hydrogen, or an acyl group and m and n are each an integer of 0 or 1,
Z is aryl which may have 1 or more suitable substituent(s).

4. The compound of claim 3, wherein $R^3$ is hydrogen, lower alkyl, lower alkenyl, cyclo(lower)alkyl(lower)allkyl, cyclo(lower)alkylcarbonyloxy(lower)altlo , halogen, lower alkanoyl, morpholinocarbonyl(lower)alkyl, lower alkanoylamino, lower alkoxycarbonylamino(lower)alkyl, lower alkanoylamino(lower)alkyl, morpholinocarbonylamino(lower)allkyl, carboxy(lower)alkenyl, protected carboxy(lower)alkenyl, lower alkanoyloxy(lower)alkyl, benzoyloxy(lower)alkyl, protected carboxyoxy(lower)alkyl, protected carboxy(lower)alkylthio(lower)alkyl, amino(lower)alkyl, di-lower alkylamino, di-lower alkylaminocarbonyl(lower)alkyl, lower alkylaminocarbonyl(lower)alkyl, carboxy(lower)alkyl, protected carboxy(lower )alkyl, lower alkylthio(lower)alkyl, di-lower alkoxyphosphoryl(lower)alkyl, di-lower alkoxyphosphoryloxy(lower)alkyl, hydroxyimino(lower)alkyl, hydroxy(lower) alkyl which may have 1 to 3 substituent(s) selected from the group consisting of protected carboxy, tri-halo(lower)alkyl, cyclo(lower)alkyl and phenyl, hydroxy(lower)alkylthio(lower)alkyl, di-lower alkylaminocarbonyl(lower)alkyl, carboxy(lower)alkanoyloxy(lower)alkyl, lower alkoxy(lower)alkyl, hydroxy(lower)alkylaminocarbonyl(lower)alkyl, lower alkoxy(lower)alkylaminocarbonyl(lower)alkyl, aminocarbonyl(lower)alkyl substituted with thiadiazolyl having tri-halo(lower)alkyl, imidazolyl(lower)alkyl, pyridyl(lower)alkylaminocarbonyl(lower)alkyl, thiazolyl having lower alkanoylamino, imidazolylthio(lower)alkyl, or a group of the formula:

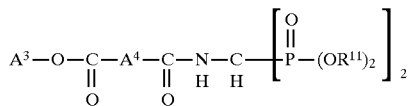

wherein $A^3$ is lower alkylene which may have 1 to 3 substituent(s) selected from the group consisting of protected carboxy, tri-halo(lower)alkyl, cyclo(lower)alkyl and phenyl,
$R^{11}$ is hydrogen or lower alkyl, and
$A^4$ is lower alkylene or a group of the formula:

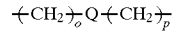

(wherein Q is phenylene which may have 1 to 3 substituent(s) selected from the group consisting of lower alkyl and lower alkoxy, or cyclo(lower)alkyl which may have 1 to 3 substituent(s) selected from the group consisting of lower alkyl and lower alkoxy, and o and p are each an integer of 0 to 1, in which $R^2$ and $R^3$ may be linked together to form
(1) lower alkylene which may have 1 to 3 substituent (s), selected from the group consisting of lower alkyl, hydroxy and oxo,
(2) lower alkenylene, or
(3) a group of the formula:

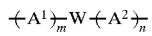

wherein $A^1$ and $A^2$ are each lower alkylene which may have 1 to 3 substituent(s) selected from the group consisting of hydroxy and oxo,

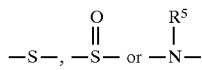

W is
wherein $R^5$ is hydrogen or an acyl group, and m and n are each an integer of 0 or 1,
Z is naphthyl which may have 1 to 3 substituent(s) selected from the group consisting of lower alkyl, oxo, hydroxy, lower alkoxy, nitro and halogen, or a group of the formula:

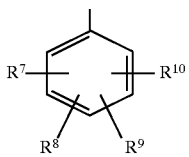

wherein
$R^7$, $R^8$, $R^9$ and $R^{10}$ are each hydrogen, halogen, lower alkayl, nitro, lower, lower aloxy, carbamoyl, protected carboxy, carboxy, benzoyl, cyclo(lower)alkoyl, tri-halo(lower)alkyl, lower alkanoylamino, ureido, phenyl, amino, mono- or di-lower alkylamino, hydroxyamino, phenoxy, phenyl(lower)alkoxy, hydroxy, hydroxy(lower)alkyl, pyrroyl which may have 1 to 3 lower alkyl, lower alkanoyloxy(lower)alkanoylamino, morpholino (lower)alkanoylamino, lower alkoxy(lower)alkanoylamino, hydroxy(lower)alkanoylamiino, di-(lower)alkylamino(lower)allkyl, protected carboxy(lower)alkoxy, di-(lower)alkylamino(lower)alkanoylamino, lower alkysulfonyamino, or bis(lower alkoxy(lower)alkyl)amino(lower) alkanoylamino.

5. The compound of claim 3, wherein Z is a group of the formula:

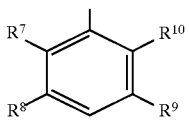

wherein
$R^7$ is halogen, lower alkyl, nitro lower alkoxy, carbamoyl, carboxy, protected carboxy, lower alkoxy, amino, phenoxy or phenyl(lower) alkoxy,
$R^8$ is hydrogen, halogen or lower alkyl,
$R^9$ is hydrogen, halogen, lower alkyl, lower alkoxy, hydroxy, hydroxy(lower)alkyl, nitro, amino, lower alkanoylamino, hydroxyamino, lower alkylamino, lower alkanoyloxy(lower)alkanoylamino, morpholino (lower)alkanoylamino, lower alkoxy(lower) alkanoylamino, pyrroyl which may have 1 to 3 lower alkyl, hydroxy(lower)alkanoylamino, di-lower alkylamino(lower)alkyl, protected carboxy(lower) alkoxy, lower alkysulfonylamino, or di-lower alkoxy (lower)alkylamino(lower)alkanoylamino, $R^{10}$ is hydrogen, halogen, lower alkyl, nitro, lower alkoxy, benzoyl, cyclo(lower)alkyl or tri-halo(lower)alkyl.

6. The compound of claim 5, wherein
$R^2$ is lower alkyl,
$R^3$ is hydroxy(lower)alkyl, cyclo(lower) alkylaminocarbonyl(lower)alkyl, protected carboxy (lower)alkyl, hydroxy(lower)alkylaminocarbonyl (lower)alkyl, lower alkoxy(lower)alkylaminocarbonyl (lower)alkyl, carbonyl(lower)alkyl which may have one or more suitable substituent(s), lower alkylaminocarbonyl(lower)alkyl which may have one or more suitable substituent(s) or a group of the formula:

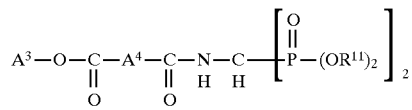

wherein $A^3$ is lower alkylene,
$R^{11}$ is hydrogen and
$A^4$ is lower alkylene, and
Z is a group of the formula:

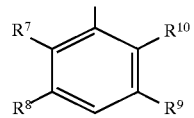

wherein $R^7$ is halogen or lower alkyl,
$R^8$ is hydrogen,
$R^9$ is hydrogen, di-lower alkylamino(lower) alkanoylamino, lower alkanoylamino, amino, lower alkoxy(lower)alkanoylaamino, hydroxy(lower) alkanoylamino, hydroxyamino, lower alkoxy or hydroxy, and
$R^{10}$ is halogen or lower alkyl.

7. The compound of claim 1, wherein $R^3$ is hydroxy (lower)alkyl, or a group of the formula:

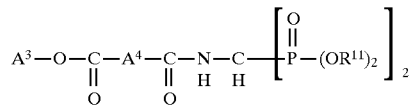

(wherein $A^3$ is lower alkylene, $R^{11}$ is hydrogen, and $A^4$ is lower alkylene) and Z is a group of the formula:

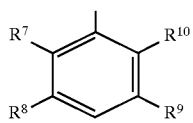

(wherein $R^7$ is halogen or lower alkyl,
$R^8$ and $R^9$ are each hydrogen, and
$R^{10}$ is halogen or lower alkyl).

8. The compound of claim 1, wherein
$R^3$ is protected carboxy(lower)alkyl, and
Z is a group of the formula:

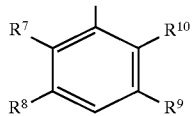

(wherein $R^7$ is halogen or lower alkyl,
$R^8$ and $R^9$ are each hydrogen, and
$R^{10}$ is halogen or lower alkyl).

9. The compound of claim 1, wherein
$R^3$ is cyclo(lower)alkylaminocarbonyl(lower)alkyl, and
Z is a group of the formula:

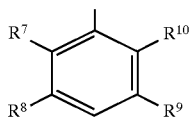

(wherein $R^7$ is halogen or lower alkyl,
$R^8$ and $R^9$ are each hydrogen, and
$R^{11}$ is halogen or lower alkyl).

10. A pharmaceutical composition which comprises, as an active ingredient, a compound of claim 1 or a pharmaceutically acceptable salt thereof in admixture with pharmaceutically acceptable carriers or excipients.

11. A method for the prophylactic and/or the therapeutic treatment of diseases caused by abnormal bone metabolism which comprises administering a compound of claim 1 or a pharmaceutically acceptable salt thereof to a human being or an animal.

* * * * *